United States Patent
Tsai et al.

(10) Patent No.: US 9,978,961 B2
(45) Date of Patent: May 22, 2018

(54) ORGANIC ELECTROLUMINESCENT MATERIALS AND DEVICES

(71) Applicant: Universal Display Corporation, Ewing, NJ (US)

(72) Inventors: Jui-Yi Tsai, Newtown, PA (US); Gregg Kottas, Ewing, NJ (US); Walter Yeager, Yardley, PA (US); Zeinab Elshenawy, Holland, PA (US); Chuanjun Xia, Lawrenceville, NJ (US); Geza Szigethy, Ewing, NJ (US); Jason Brooks, Philadelphia, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 809 days.

(21) Appl. No.: 14/310,598

(22) Filed: Jun. 20, 2014

(65) Prior Publication Data

US 2015/0194612 A1 Jul. 9, 2015

Related U.S. Application Data

(60) Provisional application No. 61/924,752, filed on Jan. 8, 2014.

(51) Int. Cl.
| | |
|---|---|
| H01L 51/54 | (2006.01) |
| C09K 11/06 | (2006.01) |
| H01L 51/00 | (2006.01) |
| C07F 15/00 | (2006.01) |
| H01L 51/50 | (2006.01) |

(52) U.S. Cl.
CPC ...... *H01L 51/0085* (2013.01); *C07F 15/0033* (2013.01); *C09K 11/06* (2013.01); *C09K 2211/1029* (2013.01); *C09K 2211/185* (2013.01); *H01L 51/5016* (2013.01); *H01L 2251/5384* (2013.01)

(58) Field of Classification Search
None
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Left., 78(11)1622-1624 (2011).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).

(Continued)

Primary Examiner — Marie R. Yamnitzky
(74) Attorney, Agent, or Firm — Duane Morris LLP

(57) ABSTRACT

A compound comprising a ligand $L_A$ of Formula I:

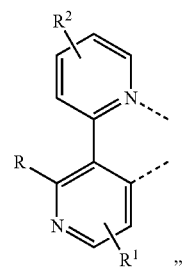

Formula I as well as, devices and formulations containing the compound of Formula 1 are disclosed. In the compounds, having a ligand La of Formula I: wherein $R^1$ represents mono, or di-substitution, or no substitution; wherein $R^2$ represents mono, di, tri, or tetra-substitution, or no substitution; wherein R is selected from hydrogen, deuterium, alkyl, cycloalkyl, and combinations thereof; wherein $R^1$ and $R^2$ are each independently selected from hydrogen, deuterium, alkyl, cycloalkyl, aryl, and combinations thereof; wherein any adjacent substituents of $R^2$ are optionally joined to form a fused ring; wherein the ligand $L_A$ is coordinated to a metal M; and wherein the ligand $L_A$ is optionally linked with other ligands to comprise a tridentate, tetradentate, pentadentate or hexadentate ligand.

14 Claims, 10 Drawing Sheets

(56) References Cited

U.S. PATENT DOCUMENTS

| | | | |
|---|---|---|---|
| 6,528,187 B1 | 3/2003 | Okada | |
| 6,687,266 B1 | 2/2004 | Ma et al. | |
| 6,835,469 B2 | 12/2004 | Kwong et al. | |
| 6,893,743 B2 * | 5/2005 | Sato et al. | H01L 51/0059 257/102 |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 * | 2/2008 | Ma et al. | C07F 15/0033 257/E51.044 |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0170209 A1 * | 8/2005 | Lee et al. | C07F 15/0033 428/690 |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2009/0261721 A1 * | 10/2009 | Murakami et al. | C09K 11/06 313/504 |
| 2011/0049496 A1 * | 3/2011 | Fukuzaki | C07F 15/0033 257/40 |
| 2015/0322102 A1 * | 11/2015 | Noh et al. | C07F 15/0033 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| KR | 10-2013-0042865 | 4/2013 |
| WO | 01/39234 | 5/2001 |
| WO | 02/027414 | 1/2002 |
| WO | 02/15645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009130 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011028479 | 3/2011 |
| WO | 2011059722 | 5/2011 |
| WO | 2011059724 | 5/2011 |
| WO | 2011059726 | 5/2011 |
| WO | 2011059787 | 5/2011 |
| WO | 2011059789 | 5/2011 |
| WO | 2011059814 | 5/2011 |
| WO | 2011059816 | 5/2011 |
| WO | 2011059825 | 5/2011 |
| WO | 2012069170 | 5/2012 |

OTHER PUBLICATIONS

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

(56) References Cited

OTHER PUBLICATIONS

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) riphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes containing N^C^N-Coordinating Tridentate Ligand," Appl. Phys. Lett., 86:153505-1-153505-3 (2005).
38 Sun, Yiru and Forrest, Stephen R, "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical characteristics Related to Structure," Synthetic Metals, 88:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. And VanSLYKE, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S.A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

Formula I

ORGANIC ELECTROLUMINESCENT MATERIALS AND DEVICES

CROSS-REFERENCE TO RELATED APPLICATIONS

This application is a non-provisional of U.S. Patent Application Ser. No. 61/924,752, filed Jan. 8, 2014, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

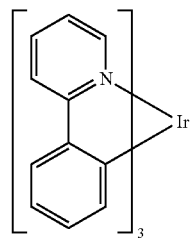

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than"

or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound comprising a ligand $L_A$ of Formula I:

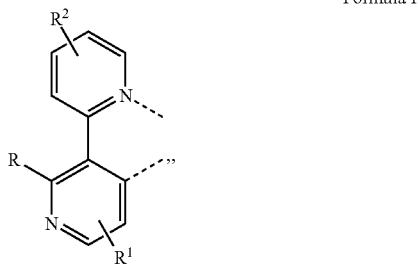

Formula I as well as, devices and formulations containing the compound of Formula 1 are disclosed. In the compounds, having a ligand $L_A$ of Formula I:
wherein $R^1$ represents mono, or di-substitution, or no substitution;
wherein $R^2$ represents mono, di, tri, or tetra-substitution, or no substitution;
wherein R is selected from the group consisting of hydrogen, deuterium, alkyl, cycloalkyl, and combinations thereof;
wherein $R^1$ and $R^2$ are each independently selected from the group consisting of hydrogen, deuterium, alkyl, cycloalkyl, aryl, and combinations thereof;
wherein any adjacent substituents of $R^2$ are optionally joined to form a fused ring;
wherein the ligand $L_A$ is coordinated to a metal M; and
wherein the ligand $L_A$ is optionally linked with other ligands to comprise a tridentate, tetradentate, pentadentate or hexadentate ligand.

According to another embodiment, a first device comprising a first organic light emitting device is also provided. The first organic light emitting device can include an anode, a cathode, and an organic layer, disposed between the anode and the cathode. The organic layer can include a compound having a ligand $L_A$ having a structure of Formula I. The first device can be a consumer product, an organic light-emitting device, and/or a lighting panel.

Formulations containing a compound having a ligand $L_A$ having a structure of Formula I are also described.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
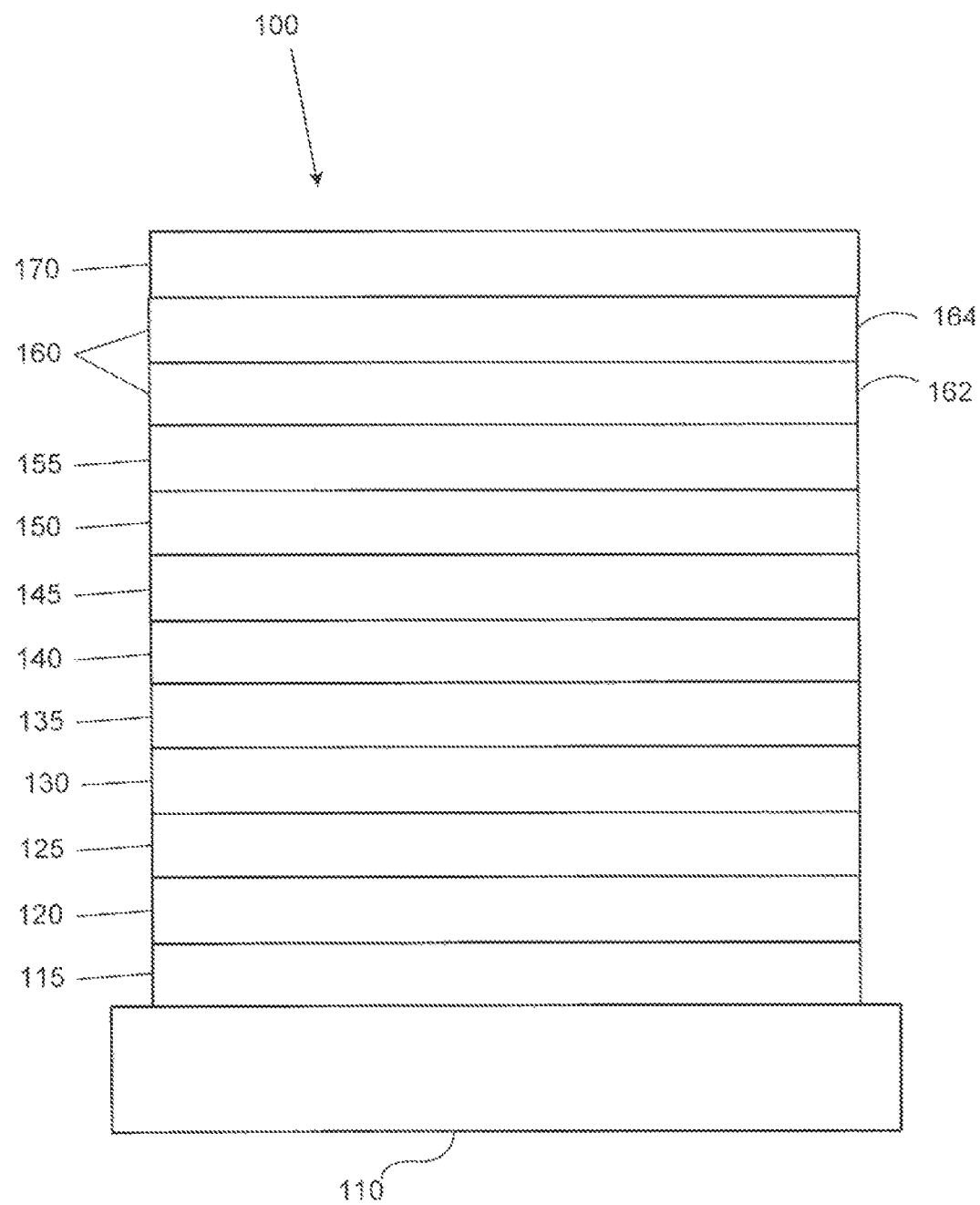
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
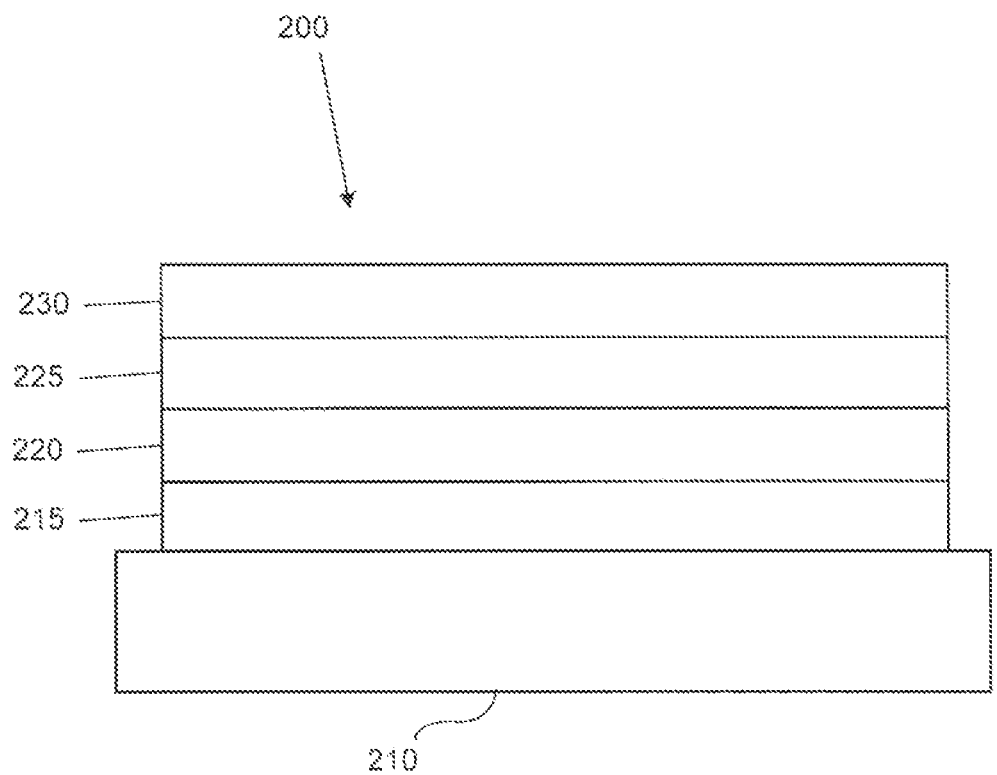
FIG. 2 shows an inverted organic light emitting device that does not have a separate electron transport layer.
Figure 3:
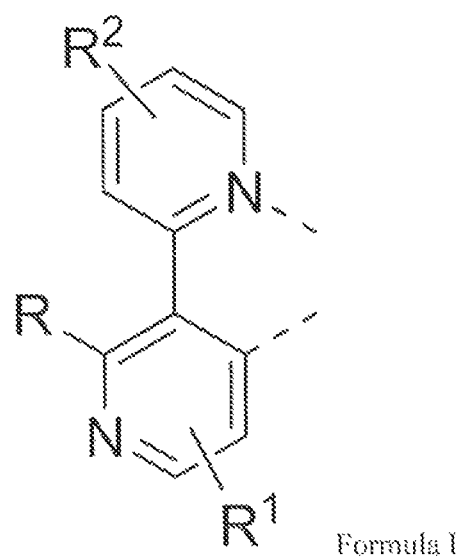
FIG. 3 shows a ligand $L_A$ of Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

According to one embodiment, a compound including a ligand $L_A$ of Formula I:

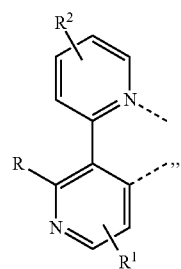

Formula I is disclosed.

In the ligand $L_A$ of Formula I:

$R^1$ represents mono, or di-substitution, or no substitution;

$R^2$ represents mono, di, tri, or tetra-substitution, or no substitution;

R is selected from the group consisting of hydrogen, deuterium, alkyl, cycloalkyl, and combinations thereof;

$R^1$ and $R^2$ are each independently selected from the group consisting of hydrogen, deuterium, alkyl, cycloalkyl, aryl, and combinations thereof;

where any adjacent substituents of $R^2$ are optionally joined to form a fused ring;

the ligand $L_A$ is coordinated to a metal M; and the ligand $L_A$ is optionally linked with other ligands to comprise a tridentate, tetradentate, pentadentate or hexadentate ligand.

In some embodiments, at least one of $R^1$ and $R^2$ is aryl, which can be further substituted by alkyl. In some embodiments, $R^1$ includes at least one aryl, which can be further substituted with alkyl. In some embodiments, $R^1$ includes exactly one aryl, which can be further substituted with alkyl. In some embodiments, $R^2$ includes at least one aryl, which can be further substituted with alkyl. In some embodiments, $R^2$ includes exactly one aryl, which can be further substituted with alkyl.

In some embodiments, R is hydrogen. In some embodiments, R is alkyl.

In some embodiments, M is selected from the group consisting of Ir, Rh, Re, Ru, Os, Pt, Au, and Cu. In some embodiments, M is Ir.

In some embodiments, $L_A$ is bidentate. In other words, $L_A$ is exactly bidentate and is not linked to other ligands to form a tridentate or higher ligand.

In some embodiments, $L_A$ is selected from the group consisting of:

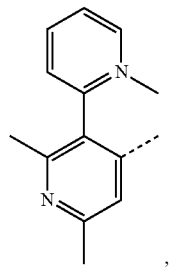

$L_{A1}$

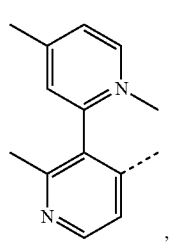

$L_{A2}$

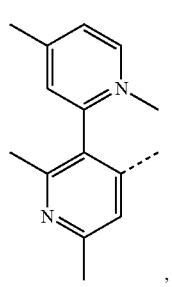

$L_{A3}$

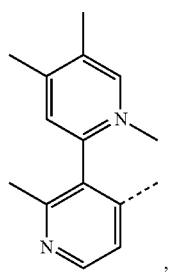

$L_{A4}$

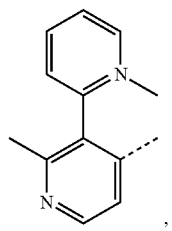

$L_{A5}$

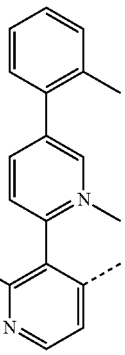

$L_{A6}$

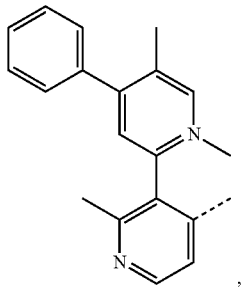

$L_{A7}$

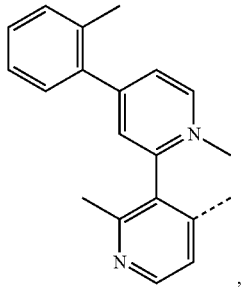

$L_{A8}$

L_{A9}
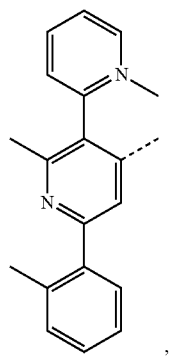
L_{A10}
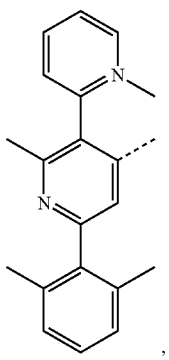
L_{A11}
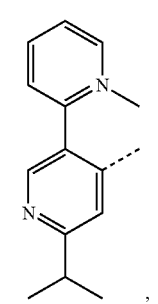
L_{A12}
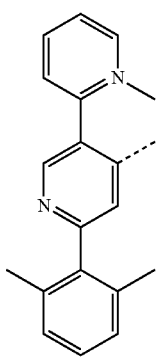
L_{A13}
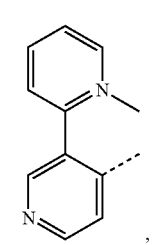
L_{A14}
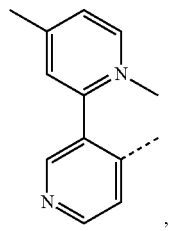
L_{A15}
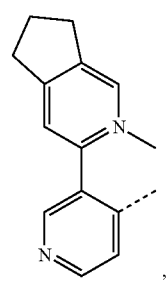
L_{A16}
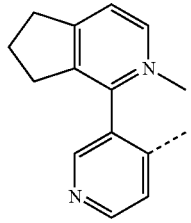
L_{A17}
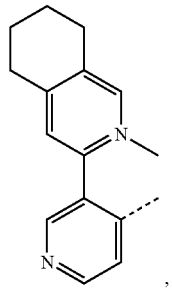
L_{A18}
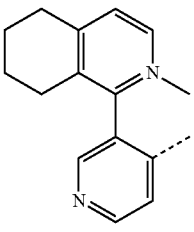

L_{A19}
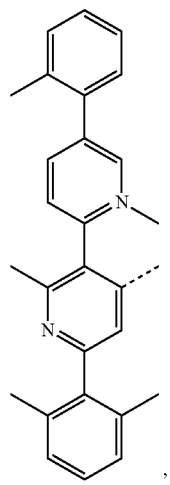

L_{A20}
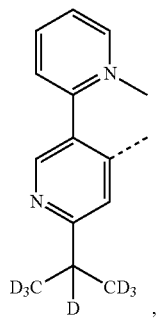

L_{A21}
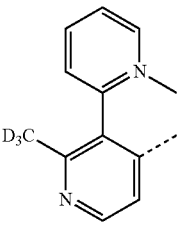

L_{A22}
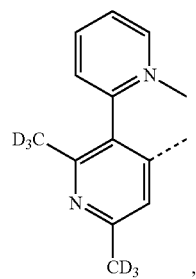

L_{A23}
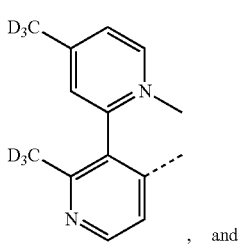, and

L_{A24}
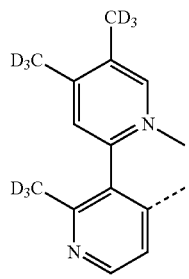

In some embodiments, the compound has the formula $M(L_A)_m(L)_n$, having the structure:

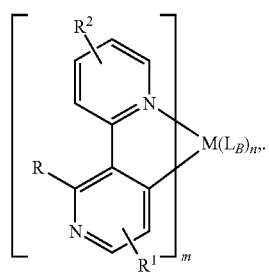

Formula II

In the compound of Formula II:

$L_B$ is a different ligand from $L_A$;

m is an integer from 1 to the maximum number of ligands that may be coordinated to the metal M; and m+n is the maximum number of ligands that may be coordinated to the metal M.

In some embodiments having a structure of Formula II, m is 1 or 2; and $L_B$ is selected from the group consisting of:

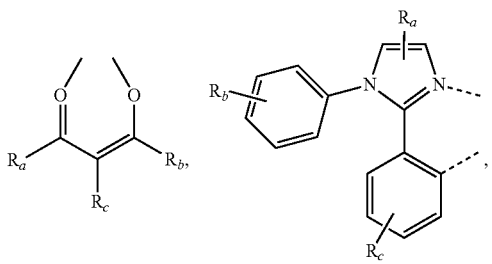

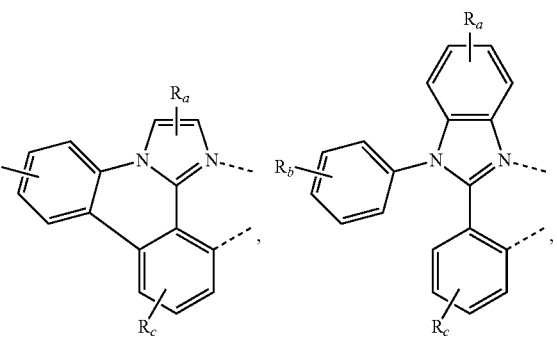

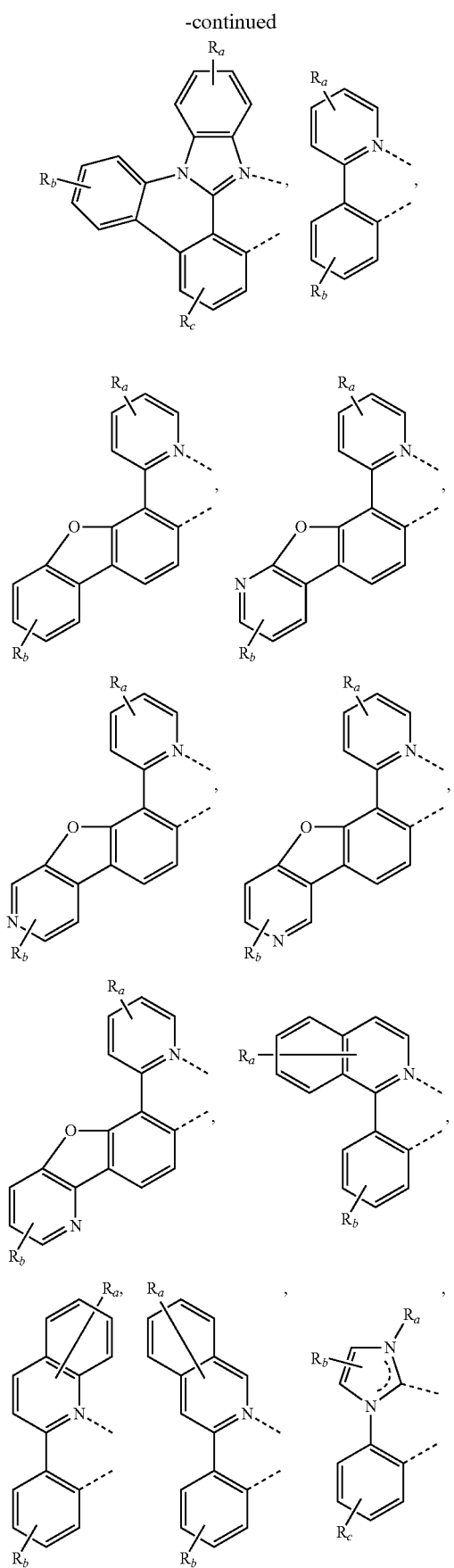
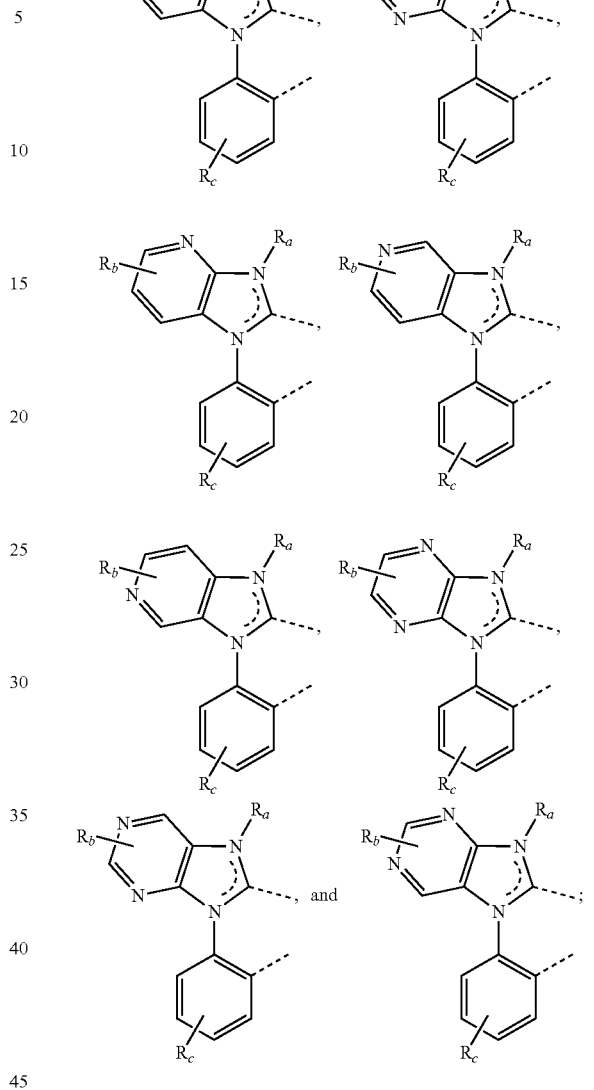

where $R_a$, $R_b$, $R_c$, and $R_d$ may represent mono, di, tri, or tetra substitution, or no substitution;

where $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and where two adjacent substituents of $R_a$, $R_b$, $R_c$, and $R_d$ are optionally joined to form a fused ring or form a multidentate ligand.

In some embodiments, the compound is heteroleptic. In some embodiments, the compound is homoleptic. In some embodiments, the compound has a facial configuration. In some embodiments, the compound has a meridional configuration.

In some embodiments, the compound has the structure of Formula III:

Formula III
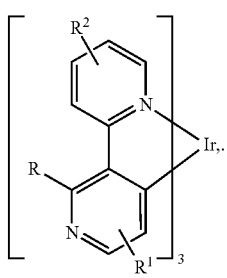
In some more specific embodiments, the compound is selected from the group consisting of:
Compound 1
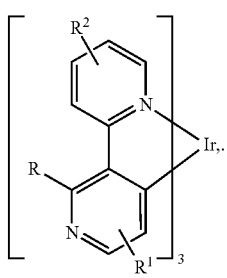
Compound 2
Compound 3
Compound 4
-continued
Compound 5
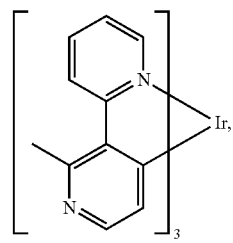
Compound 6
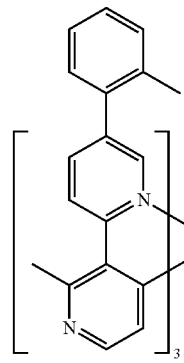
Compound 7
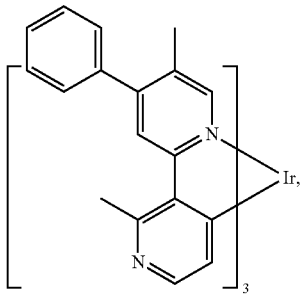
Compound 8
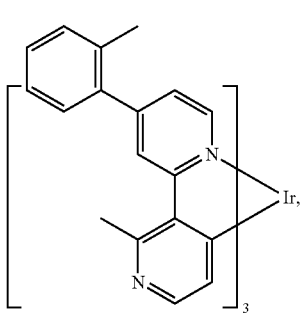
Compound 9
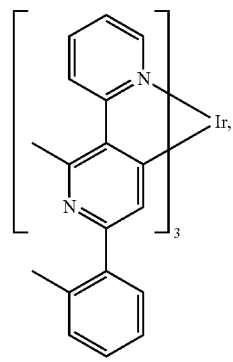

Compound 10
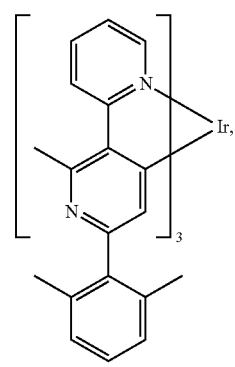
Compound 11
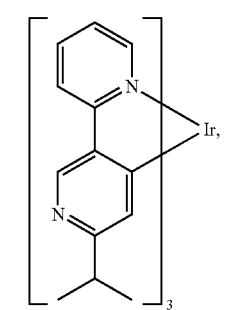
Compound 12
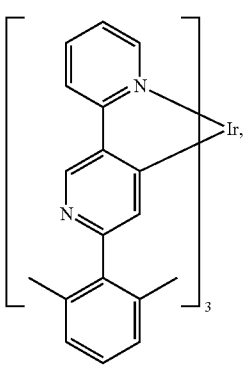
Compound 13
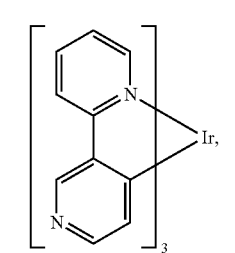
Compound 14
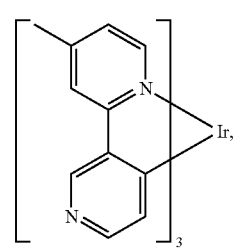
Compound 15
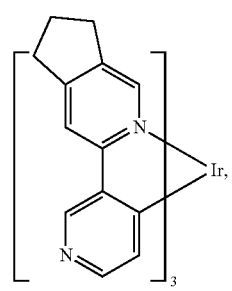
Compound 16
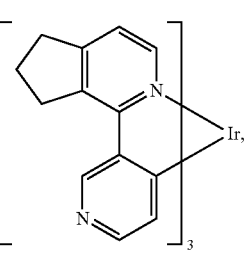
Compound 17
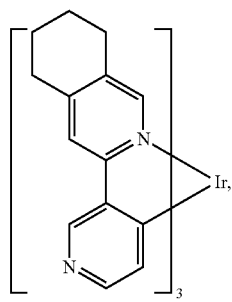
Compound 18
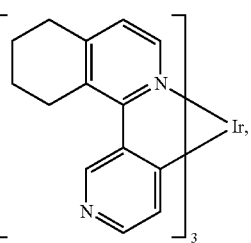
Compound 19
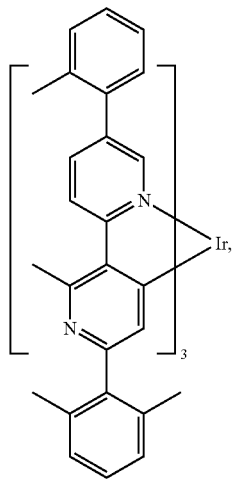

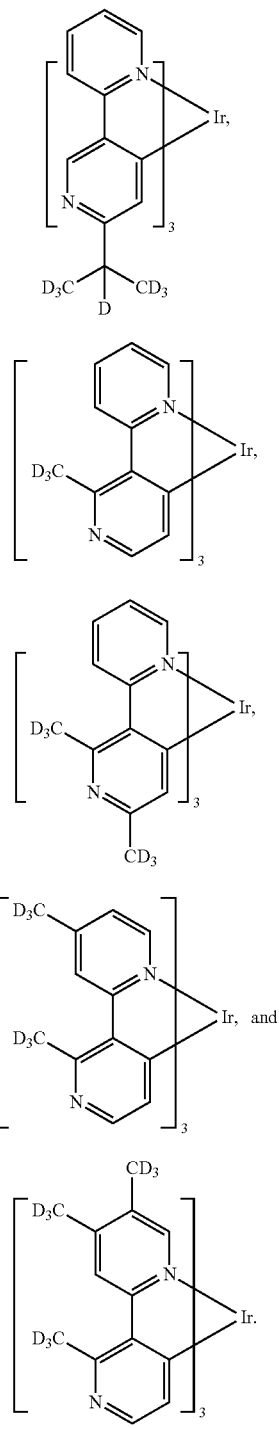

Compound 20

Compound 21

Compound 22

Compound 23

Compound 24

According to another aspect of the present disclosure, a first device is also provided. The first device includes a first organic light emitting device, that includes an anode, a cathode, and an organic layer disposed between the anode and the cathode. The organic layer may include a host and a phosphorescent dopant. The emissive layer can include a compound comprising a ligand $L_A$ affording to Formula I, and variations of the compound as described herein.

The first device can be one or more of a consumer product, an organic light-emitting device and a lighting panel. The organic layer can be an emissive layer and the compound can be an emissive dopant in some embodiments, while the compound can be a non-emissive dopant in other embodiments.

The organic layer can also include a host. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1$-$Ar_2$, $C_nH_{2n}$—$Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound selected from the group consisting of carbazole, dibenzothiophene, dibenzofuran, dibenzoselenophene, azacarbazole, aza-dibenzothiophene, aza-dibenzofuran, and aza-dibenzoselenophene. The host can include a metal complex. The host can be a specific compound selected from the group consisting of:

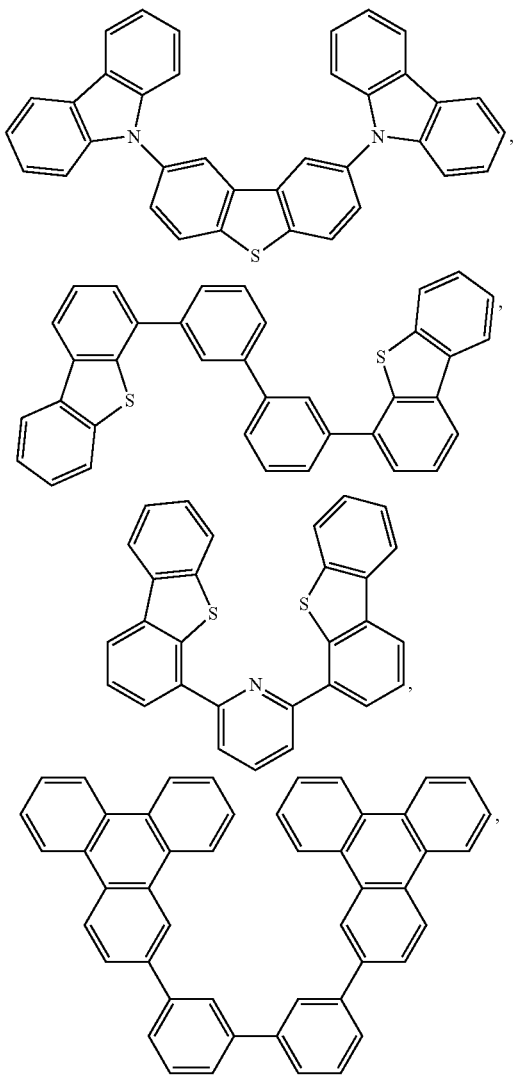

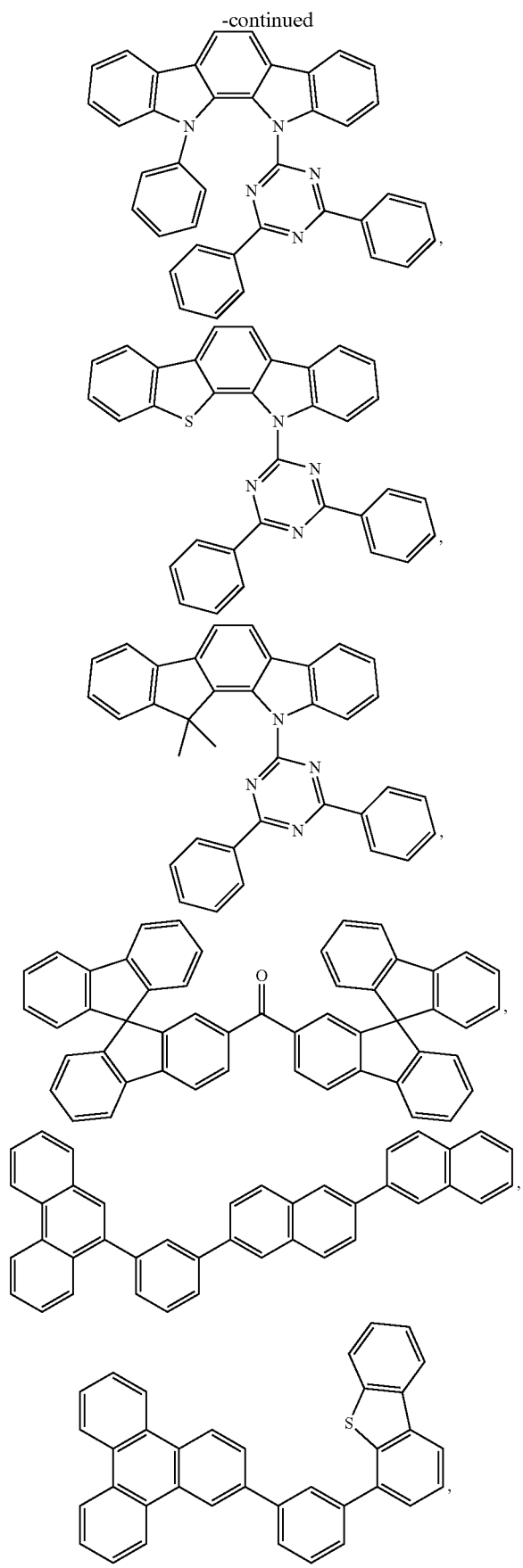

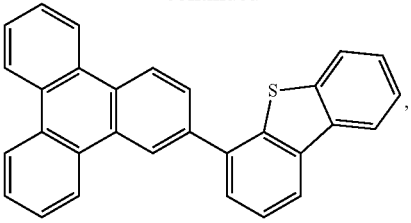

and combinations thereof.

In yet another aspect of the present disclosure, a formulation that comprises a compound comprising a ligand $L_A$ affording to Formula I, and variations of the compound as described herein. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

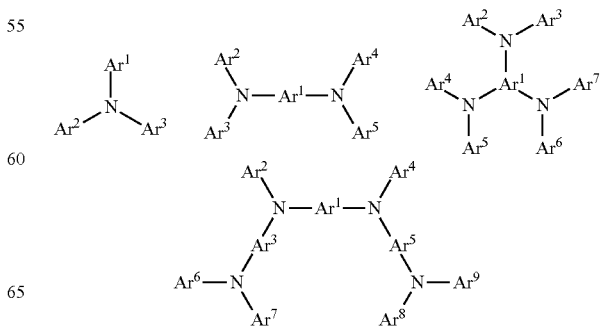

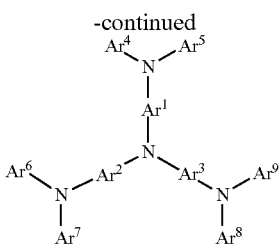

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

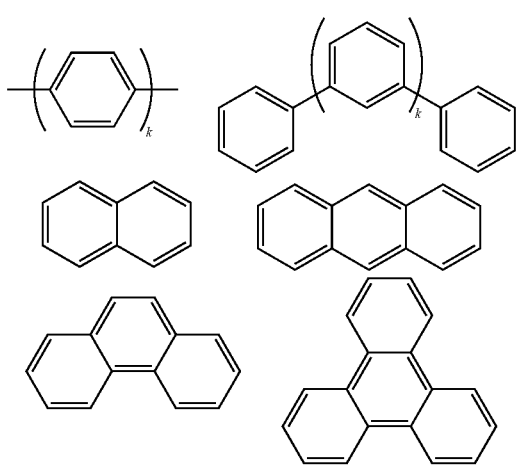

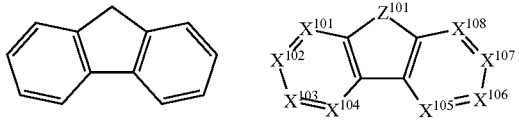

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

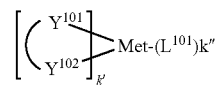

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

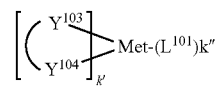

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

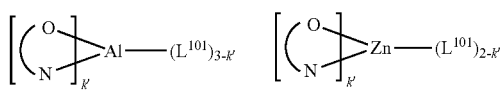

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

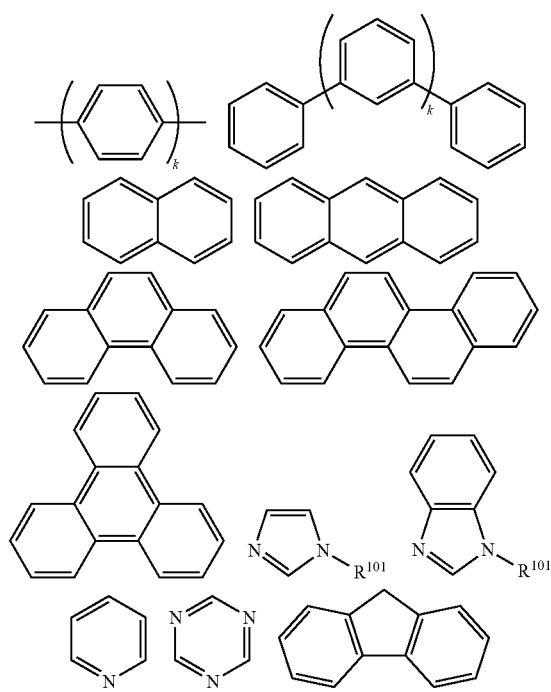

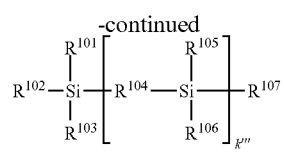

-continued

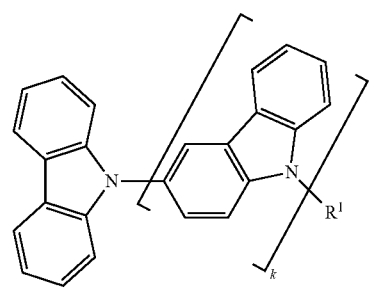

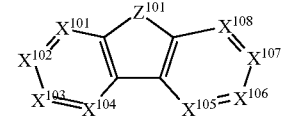

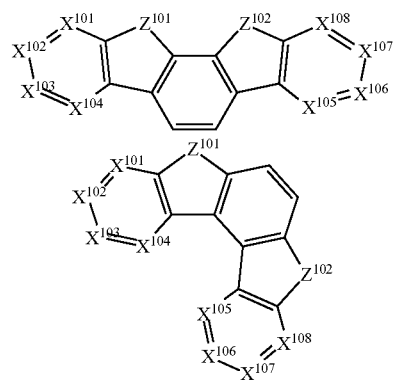

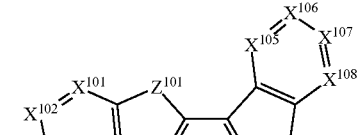

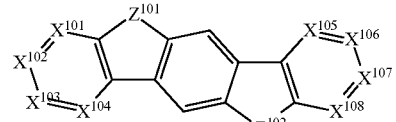

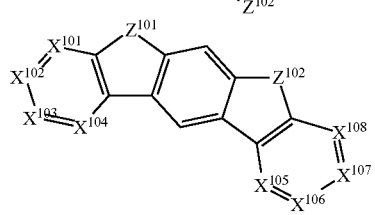

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N.

$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

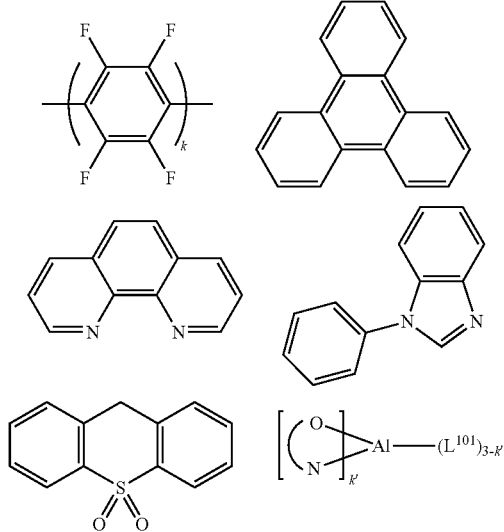

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

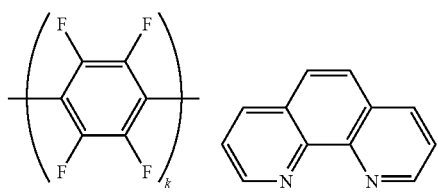

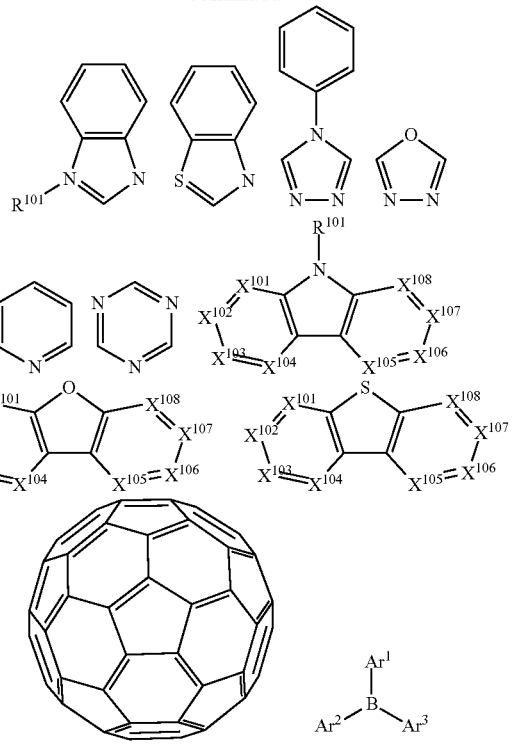

wherein $R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

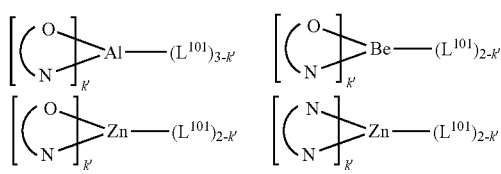

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
|---|---|---|
| Hole injection materials | | |
| Phthalocyanine and porphryln compounds | | Appl. Phys. Lett. 6, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | | Synth. Met. 87, 171 (1997) WO2007002683 |
| Phosphonic acid and silane SAMs | | US20030162053 |

TABLE A-continued
| MATERIAL | EXAMPLES OF MATERIAL | PUBLICATIONS |
|---|---|---|
| Triarylamine or polythiophene polymers with conductivity dopants | 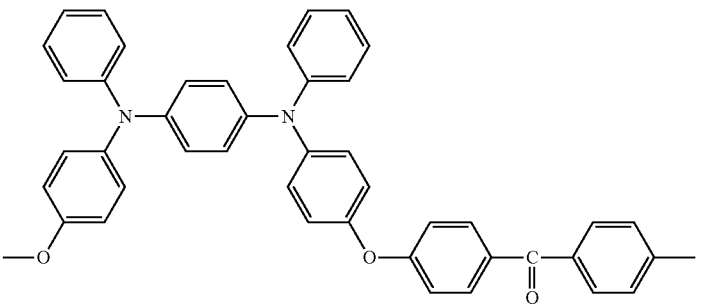 and 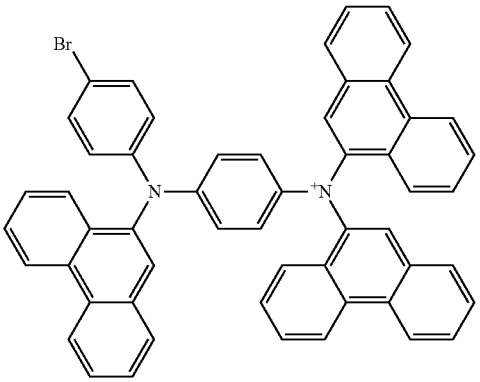 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 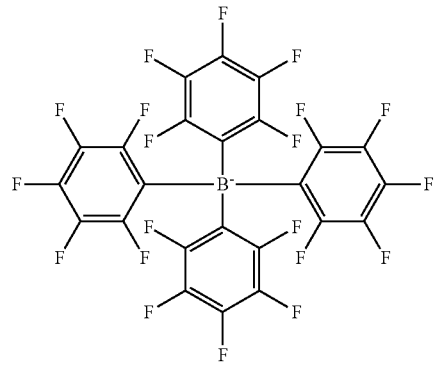 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 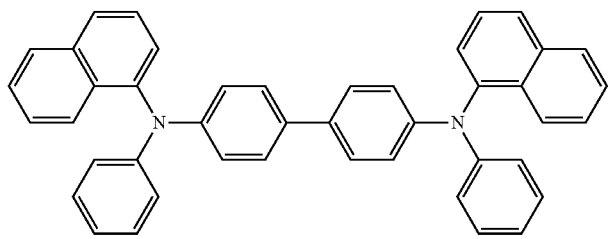 + $MoO_x$ | US20050123751 SID Symposium Digest, 37, 923 (2006) WO2009018009 |
| n-type semiconducting organic complexes | 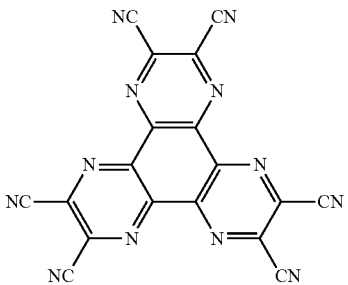 [SMILES: N#Cc1nc2c3nc(C#N)c(C#N)nc3c3nc(C#N)c(C#N)nc3c2nc1C#N] | US20020158242 |

TABLE A-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |
| Polythiophene based polymers and copolymers | | WO 2011075644<br>EP2350216 |

Hole transporting materials

| | | |
| --- | --- | --- |
| Triarylamines (e.g., TPD, α-NPD) | | Appl. Phys. Lett. 51, 913 (1987) |

TABLE A-continued

| MATERIAL | EXAMPLES OF MATERIAL | PUBLICATIONS |
|---|---|---|
| | | U.S. Pat. No. 5,061,569 |
| | | EP650955 |
| | | J. Mater. Chem. 3, 319 (1993) |

TABLE A-continued
| MATERIAL | EXAMPLES OF MATERIAL | PUBLICATIONS |
|---|---|---|
| | 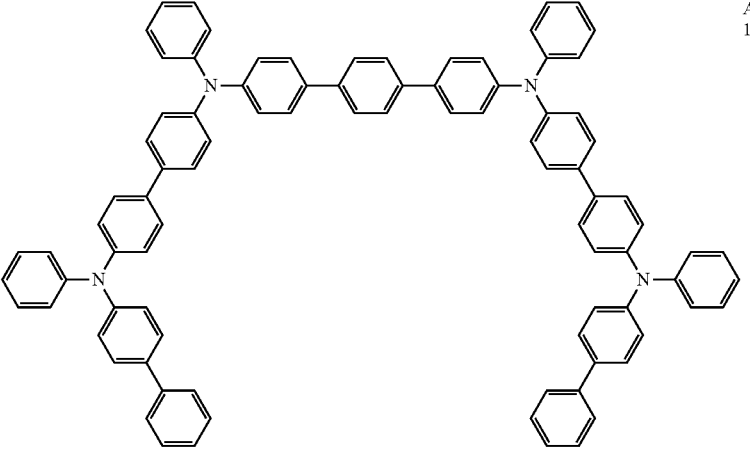 | Appl. Phys. Lett. 90, 183503 (2007) |
| | 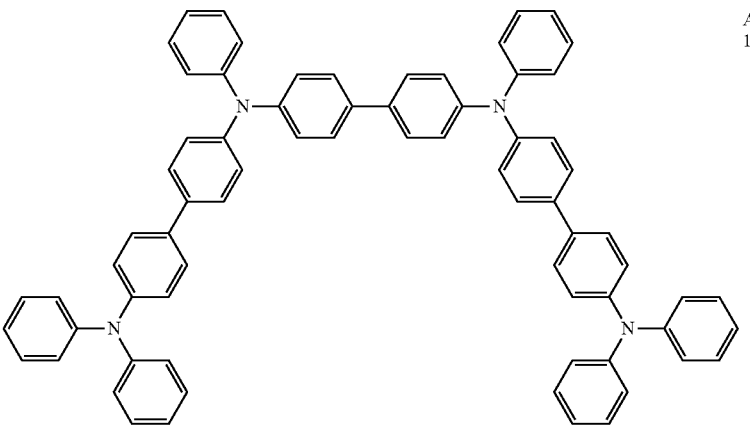 | Appl. Phys. Lett. 90, 183503 (2007) |
| Triarylamine on spirofluorene core | 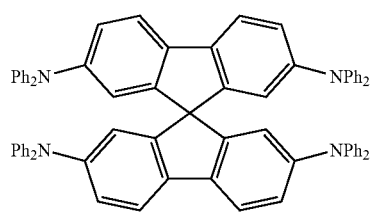 | Synth. Met. 91, 209 (1997) |
| Arylamine carbazole compounds | 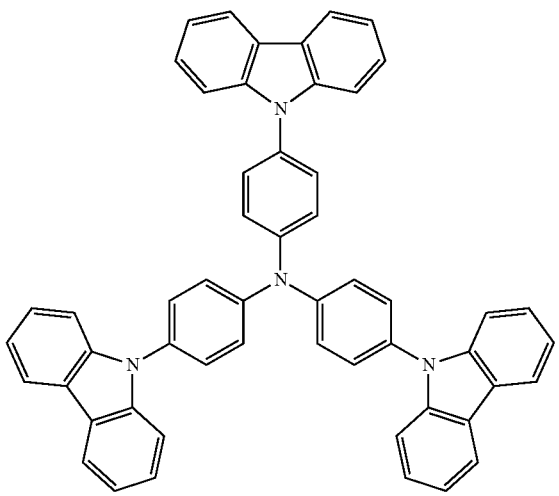 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE A-continued
| MATERIAL | EXAMPLES OF MATERIAL | PUBLICATIONS |
|---|---|---|
| Triarylamine with (di)benzothlophene/ (di)benzofuran | 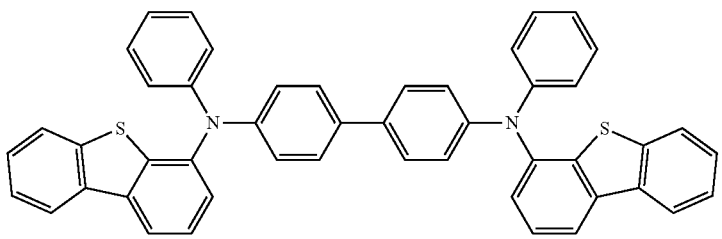 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 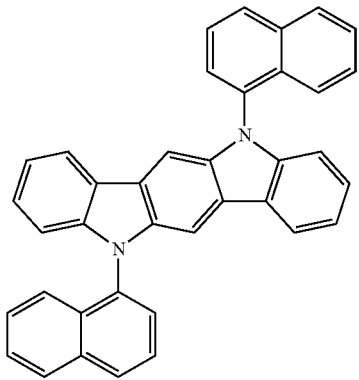 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 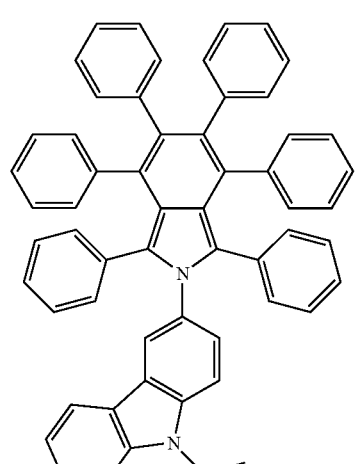 | Chem. Mater. 15, 3148 (2003) |

TABLE A-continued

| MATERIAL | EXAMPLES OF MATERIAL | PUBLICATIONS |
|---|---|---|
| Metal carbene complexes | | US20080018221 |

Phosphorescent OLED host materials
Red hosts

| | | |
|---|---|---|
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |

TABLE A-continued

| MATERIAL | EXAMPLES OF MATERIAL | PUBLICATIONS |
| --- | --- | --- |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
| --- | --- | --- |
| Arylcarbazoles | | Appl. Phys. Lett. 78, 1622 (2001) |

TABLE A-continued
| MATERIAL | EXAMPLES OF MATERIAL | PUBLICATIONS |
|---|---|---|
| | 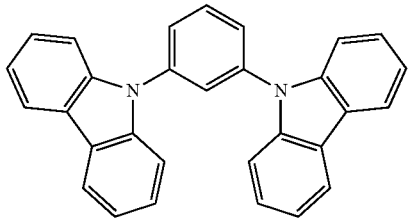 [SMILES: c1cc(-n2c3ccccc3c3ccccc32)cc(-n2c3ccccc3c3ccccc32)c1] | US20030175553 |
| | 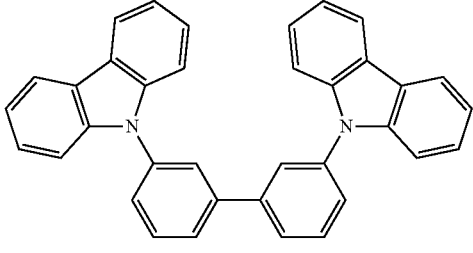 [SMILES: c1cc(-c2cccc(-n3c4ccccc4c4ccccc43)c2)cc(-n2c3ccccc3c3ccccc32)c1] | WO2001039234 |
| Aryltriphenylene compounds | 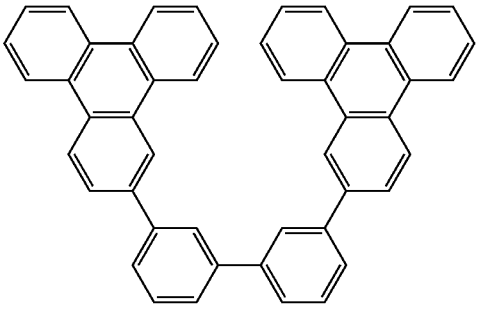 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 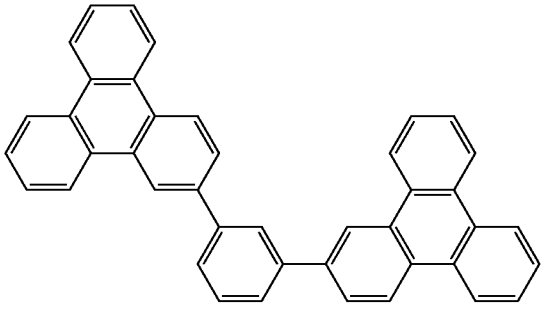 [SMILES: c1cc(-c2ccc3c4ccccc4c4ccccc4c3c2)cc(-c2ccc3c4ccccc4c4ccccc4c3c2)c1] | US20060280965 |
| | 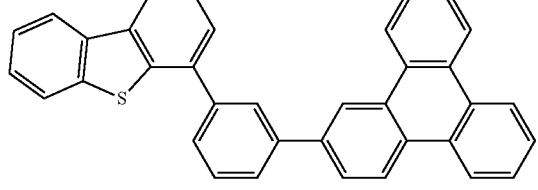 | WO2009021126 |

TABLE A-continued
| MATERIAL | EXAMPLES OF MATERIAL | PUBLICATIONS |
|---|---|---|
| Poly-fused heteroaryl compounds | 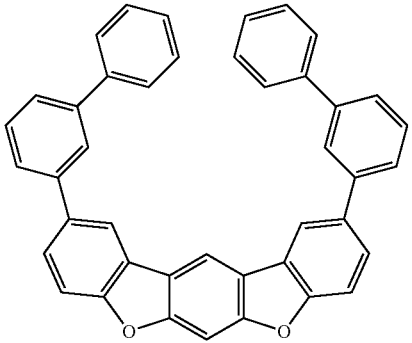 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 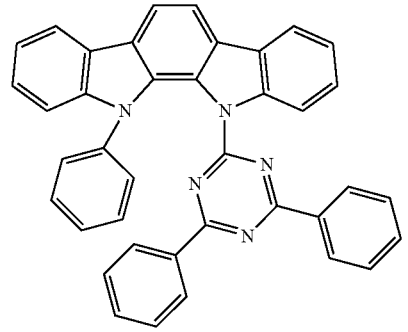 [SMILES: c1ccc(-c2nc(-c3ccccc3)nc(-n3c4ccccc4c4ccc5c6ccccc6n(-c6ccccc6)c5c43)n2)cc1] | WO2008056746 |
|  | 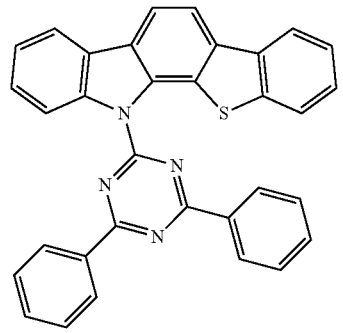 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 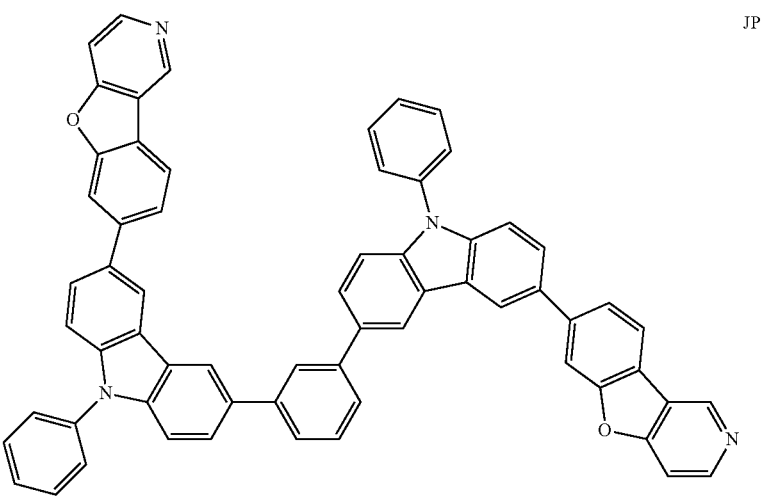 | JP2008074939 |

TABLE A-continued
| MATERIAL | EXAMPLES OF MATERIAL | PUBLICATIONS |
|---|---|---|
|  | 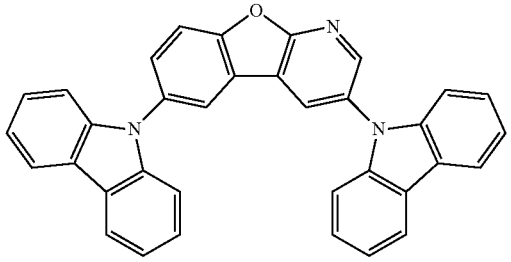 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 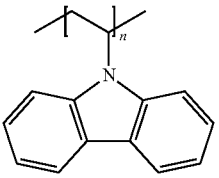 | Appl. Phys. Lett. 77, 2280 (2000) |
| Spirofluorene compounds | 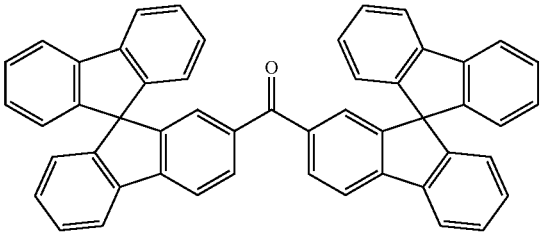 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 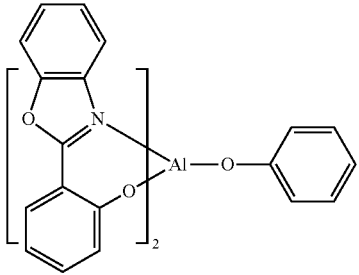 | WO2005089025 |
|  | 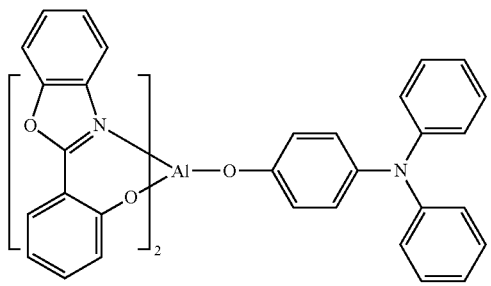 | WO2006132173 |
|  | 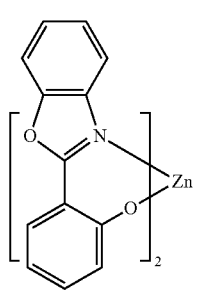 | JP200511610 |

TABLE A-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |

TABLE A-continued

| MATERIAL | EXAMPLES OF MATERIAL | PUBLICATIONS |
| --- | --- | --- |
| | [oxadiazole-phenyl-triazole structure] | WO2004107822 |
| Tetraphenylene complexes | [tetraphenylene-diphenylamine structure] | US20050112407 |
| Metal phenoxypyridine compounds | [Zn phenoxypyridine complex] | WO2005030900 |
| Metal coordination complexes (e.g., Zn, Al with N^N ligands) | [Zn pyrazole-pyridine complex] | US20040137268, US20040137267 |

Blue hosts

| | | |
| --- | --- | --- |
| Arylcarbazoles | [bis-carbazole phenyl structure] | Appl. Phys. Lett, 82, 2422 (2003) |

TABLE A-continued
| MATERIAL | EXAMPLES OF MATERIAL | PUBLICATIONS |
|---|---|---|
| | 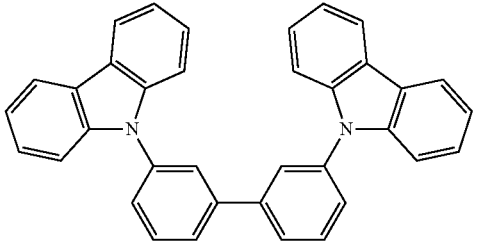 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran-carbazole compounds | 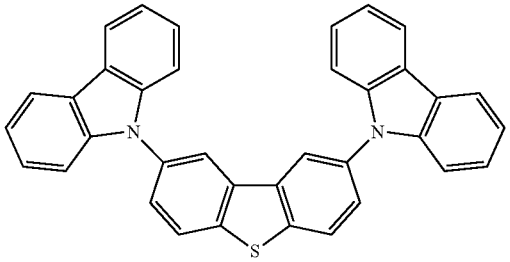 [SMILES: c1ccc2c(c1)c1ccccc1n2-c1ccc2sc3ccc(-n4c5ccccc5c5ccccc54)cc3c2c1] | WO2006114966, US20090167162 |
| | 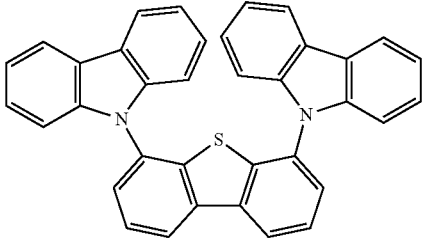 [SMILES: c1cc(-n2c3ccccc3c3ccccc32)c2sc3c(-n4c5ccccc5c5ccccc54)cccc3c2c1] | US20090167162 |
| | 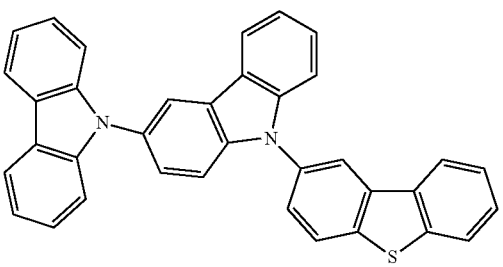 [SMILES: c1ccc2c(c1)sc1ccc(-n3c4ccccc4c4cc(-n5c6ccccc6c6ccccc65)ccc43)cc12] | WO2009086028 |
| | 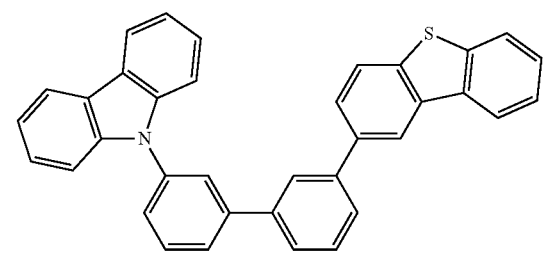 [SMILES: c1cc(-c2cccc(-n3c4ccccc4c4ccccc43)c2)cc(-c2ccc3sc4ccccc4c3c2)c1] | US20090030202, US20090017330 |
| | 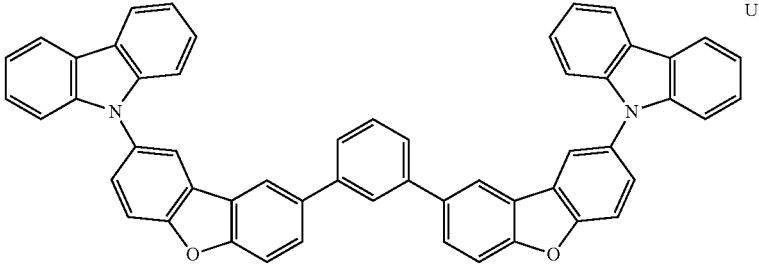 | US20100084966 |

TABLE A-continued

| MATERIAL | EXAMPLES OF MATERIAL | PUBLICATIONS |
| --- | --- | --- |
| Silicon aryl compounds | | US20050238919 |
| | | WO2009003898 |
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |

TABLE A-continued

| MATERIAL | EXAMPLES OF MATERIAL | PUBLICATIONS |
| --- | --- | --- |
| High triplet metal organometallic complex | | U.S. Pat. No. 7,154,114 |

Phosphorescent dopants
Red dopants

| MATERIAL | EXAMPLES OF MATERIAL | PUBLICATIONS |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |
| | | US20030072964 |
| | | US20030072964 |

TABLE A-continued

| MATERIAL | EXAMPLES OF MATERIAL | PUBLICATIONS |
|---|---|---|
| | | US20060202194 |
| | | US20060202194 |
| | | US20070087321 |
| | | US20080261076<br>US20100090591 |
| | | US20070087321 |

TABLE A-continued

| MATERIAL | EXAMPLES OF MATERIAL | PUBLICATIONS |
| --- | --- | --- |
| | | Adv. Mater. 19, 739 (2007) |
| | | WO2009100991 |
| | | WO2008101842 |
| | | U.S. Pat. No. 7,232,618 |
| Platinum(II) organometallic complexes | | WO2003040257 |

TABLE A-continued
| MATERIAL | EXAMPLES OF MATERIAL | PUBLICATIONS |
|---|---|---|
| | 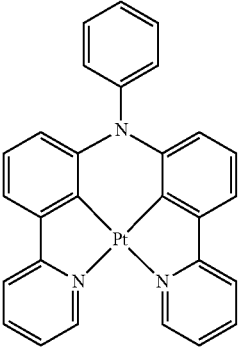 | US20070103060 |
| Osminum(III) complexes | 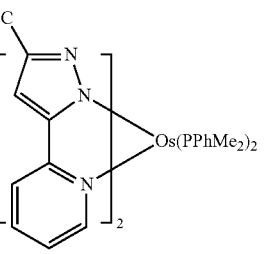 | Chem. Mater. 17, 3532 (2005) |
| Ruthenium(II) complexes | 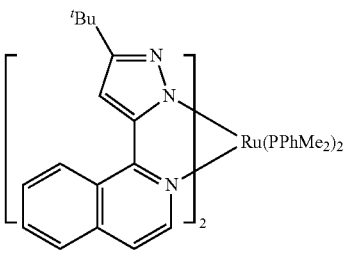 | Adv. Mater. 17, 1059 (2005) |
| Rhenium (I), (II), and (III) complexes | 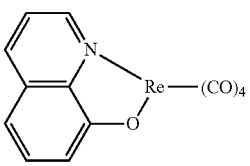 | US20050244673 |
| Green dopants | | |
| Iridium (III) organometallic complexes | 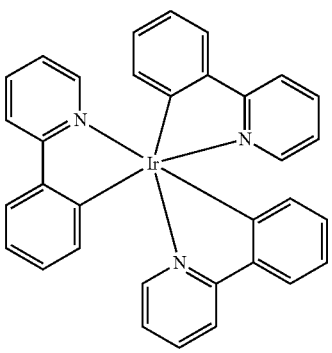 and its derivatives | Inorg. Chem. 40, 1704 (2001) |

TABLE A-continued
| MATERIAL | EXAMPLES OF MATERIAL | PUBLICATIONS |
|---|---|---|
| | 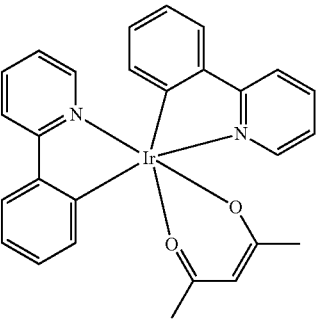 | US20020034656 |
| | 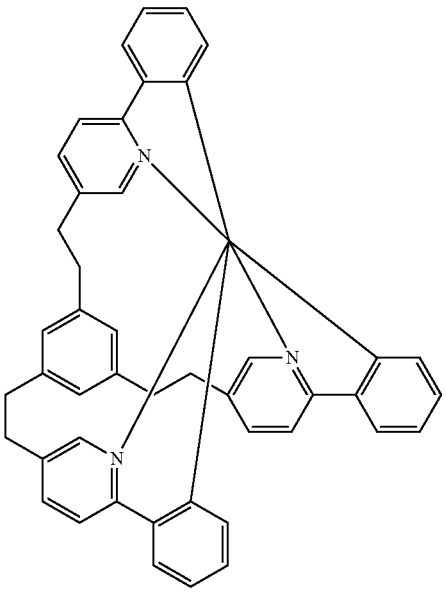 | U.S. Pat. No. 7,337,232 |
| | 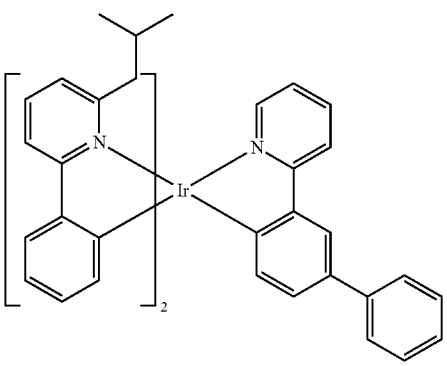 | US20090108737 |

TABLE A-continued

| MATERIAL | EXAMPLES OF MATERIAL | PUBLICATIONS |
|---|---|---|
| | | WO2010028151 |
| | | EP1841834B |
| | | US20060127696 |
| | | US20090039776 |
| | | U.S. Pat. No. 6,921,915 |

TABLE A-continued

| MATERIAL | EXAMPLES OF MATERIAL | PUBLICATIONS |
|---|---|---|
| | | US20100244004 |
| | | U.S. Pat. No. 6,687,266 |
| | | Chem. Mater. 16, 2480 (2004) |
| | | US20070190359 |
| | | US 20060008670<br>JP2007123392 |
| | | WO2010086089,<br>WO2011044988 |

TABLE A-continued
| MATERIAL | EXAMPLES OF MATERIAL | PUBLICATIONS |
|---|---|---|
| | 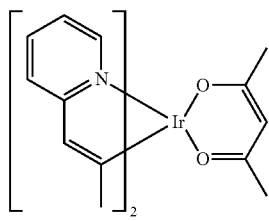 | Adv. Mater. 16, 2003 (2004) |
| | 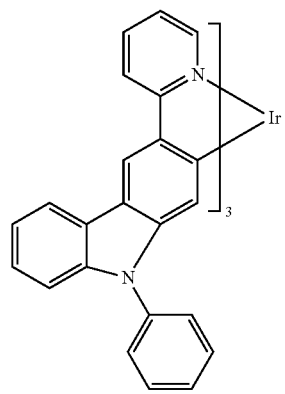 | Angew. Chem. Int. Ed. 2006, 45, 7800 |
| | 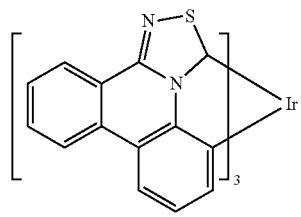 | WO2009050290 |
| | 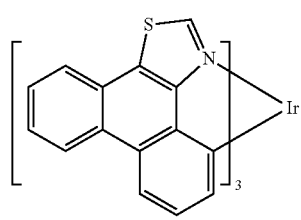 | US20090165846 |
| | 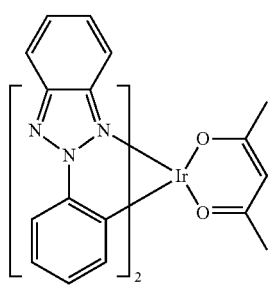 | US20080015355 |
| | 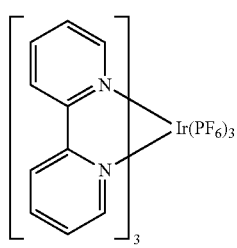 | US20010015432 |

TABLE A-continued

| MATERIAL | EXAMPLES OF MATERIAL | PUBLICATIONS |
|---|---|---|
| | (structure) | US20100295032 |
| Monomer for polymeric metal organometallic compounds | (structure) | U.S. Pat. No. 7,250,226, U.S. Pat. No. 7,396,598 |
| Pt(II) organometallic complexes, including polydentated ligands | (structure) | Appl. Phys. Lett. 86, 153505 (2005) |
| | (structure) | Appl. Phys. Lett. 86, 153505 (2005) |
| | (structure) | Chem. Lett. 34, 592 (2005) |

TABLE A-continued

| MATERIAL | EXAMPLES OF MATERIAL | PUBLICATIONS |
|---|---|---|
| | | WO2002015645 |
| | | US20060263635 |
| | | US20060182992<br>US20070103060 |
| Cu complexes | | WO2009000673 |

TABLE A-continued
| MATERIAL | EXAMPLES OF MATERIAL | PUBLICATIONS |
|---|---|---|
| | 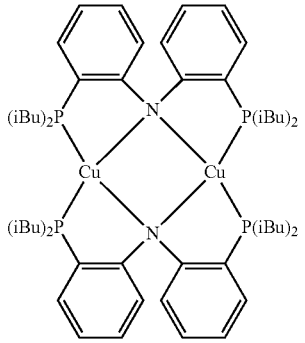 | US20070111026 |
| Gold complexes | 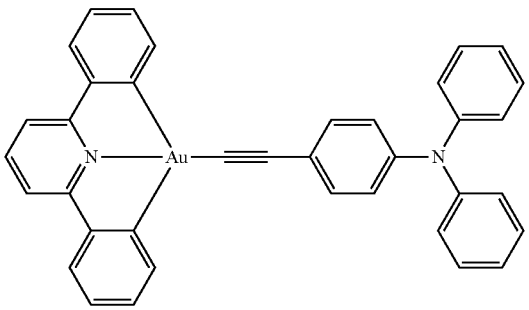 | Chem. Commun. 2906 (2005) |
| Rhenium(III) complexes | 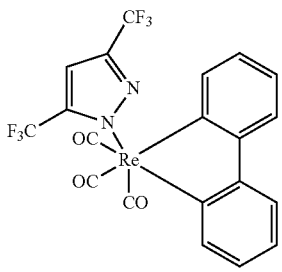 | Inorg. Chem. 42, 1248 (2003) |
| Osmium(II) complexes | 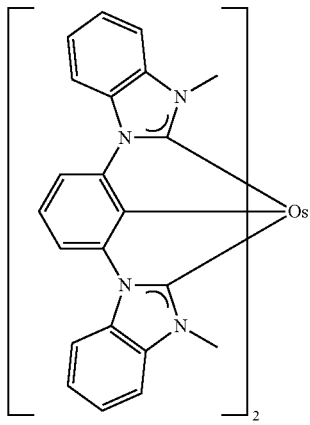 | U.S. Pat. No. 7,279,704 |

TABLE A-continued

| MATERIAL | EXAMPLES OF MATERIAL | PUBLICATIONS |
| --- | --- | --- |
| Deuterated organometallic complexes | | US20030138657 |
| Organometallic complexes with two or more metal centers | | US20030152802 |
| | | U.S. Pat. No. 7,090,928 |

Blue dopants

| | | |
| --- | --- | --- |
| Iridium(III) organometallic complexes | | WO2002002714 |

TABLE A-continued
| MATERIAL | EXAMPLES OF MATERIAL | PUBLICATIONS |
|---|---|---|
| | 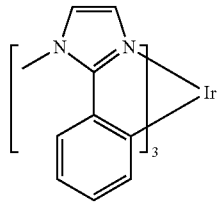 | WO2006009024 |
| | 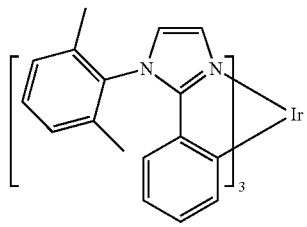 | US20060251923<br>US20110057559<br>US20110204333 |
| | 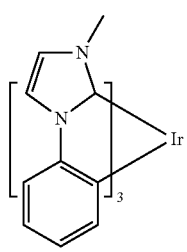 | U.S. Pat. No. 7,393,599,<br>WO2006056418,<br>US20050260441,<br>WO2005019373 |
| | 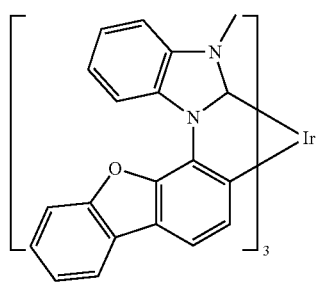 | U.S. Pat. No. 7,534,505 |
| | 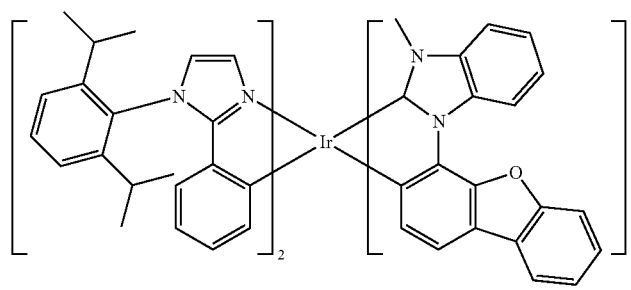 | WO2011051404 |
| | 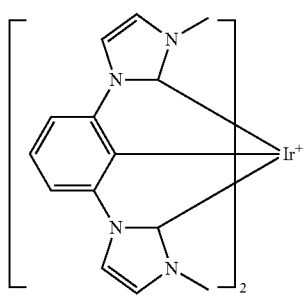 | U.S. Pat. No. 7,445,855 |

TABLE A-continued
| MATERIAL | EXAMPLES OF MATERIAL | PUBLICATIONS |
|---|---|---|
| | 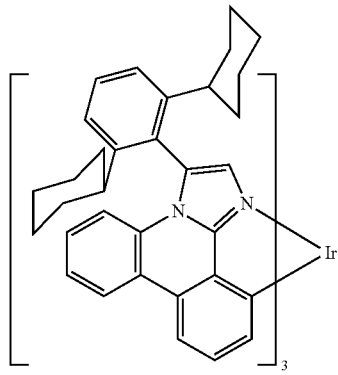 | US20070190359, US20080297033 US20100148663 |
| | 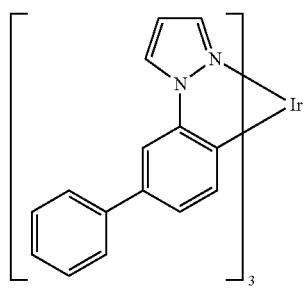 | U.S. Pat. No. 7,338,722 |
| | 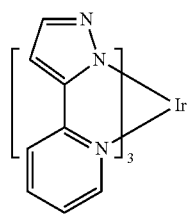 | US20020134984 |
| | 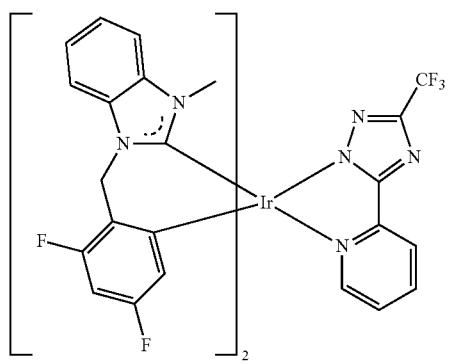 | Angew. Chem. Int. Ed. 47, 4542 (2008) |
| | 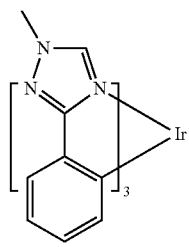 | Chem. Mater. 18, 5119 (2006) |

TABLE A-continued

| MATERIAL | EXAMPLES OF MATERIAL | PUBLICATIONS |
|---|---|---|
| | | Inorg. Chem. 46, 4308 (2007) |
| | | WO2005123873 |
| | | WO2005123873 |
| | | WO2007004380 |
| | | WO2006082742 |

TABLE A-continued
| MATERIAL | EXAMPLES OF MATERIAL | PUBLICATIONS |
| --- | --- | --- |
| Osmium(II) complexes | 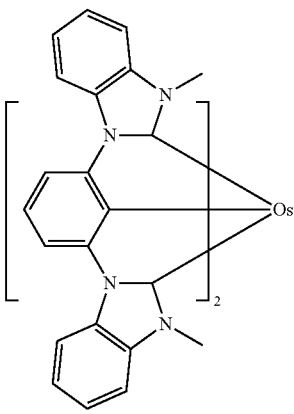 | U.S. Pat. No. 7,279,704 |
| | 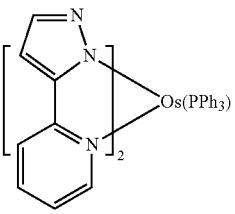 | Organometallics 23, 3745 (2004) |
| Gold complexes | 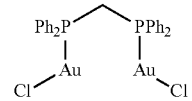 | Appl. Phys. Lett. 74, 1361 (1999) |
| Platinum(II) complexes | 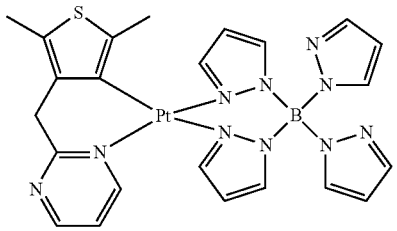 | WO2006098120, WO2006103874 |
| Pt tetradentate complexes with at least one metal-carbene bond | 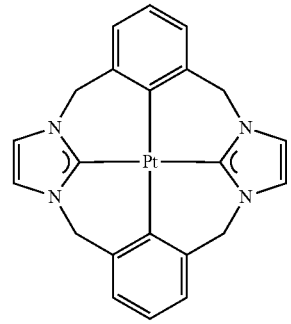 | U.S. Pat. No. 7,655,323 |
| Exciton/hole blocking layer materials | | |
| Bathocuprine compounds (e.g., BCP, BPhen) | 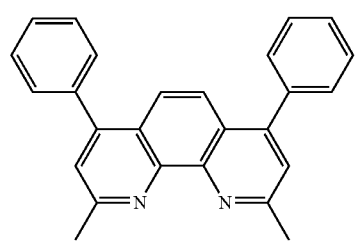 [SMILES: Cc1cc(-c2ccccc2)c2ccc3c(-c4ccccc4)cc(C)nc3c2n1] | Appl. Phys. Lett. 75, 4 (1999) |

| MATERIAL | EXAMPLES OF MATERIAL | PUBLICATIONS |
|---|---|---|
| | 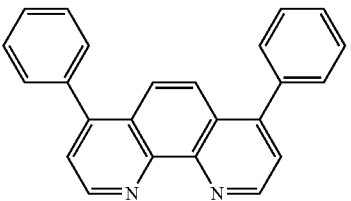 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 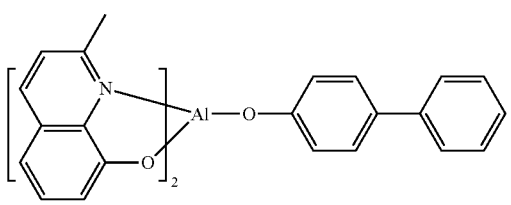 | Appl. Phys. Lett. 81, 162 (2002) |
| 5-member ring electron deficient heterocycles such as triazole, oxadiazole, imidazole, benzoimidazole | 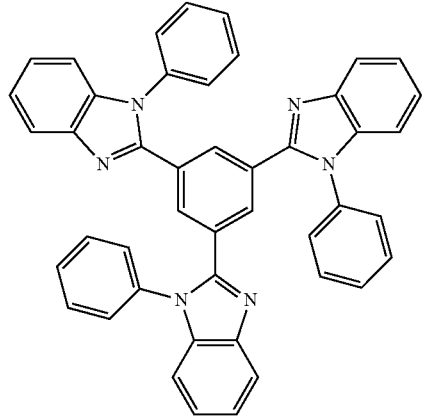 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 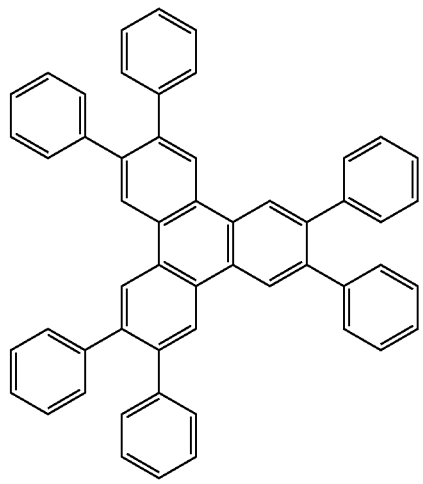 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE A-continued

| MATERIAL | EXAMPLES OF MATERIAL | PUBLICATIONS |
|---|---|---|
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |

TABLE A-continued

| MATERIAL | EXAMPLES OF MATERIAL | PUBLICATIONS |
|---|---|---|
| | Electron transporting materials | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |

TABLE A-continued

| MATERIAL | EXAMPLES OF MATERIAL | PUBLICATIONS |
| --- | --- | --- |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE A-continued
| MATERIAL | EXAMPLES OF MATERIAL | PUBLICATIONS |
|---|---|---|
| Silole compounds | 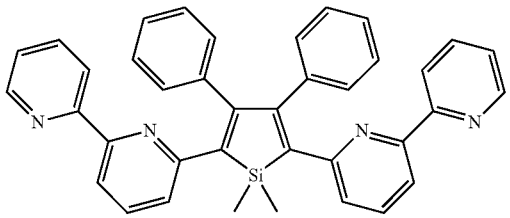 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 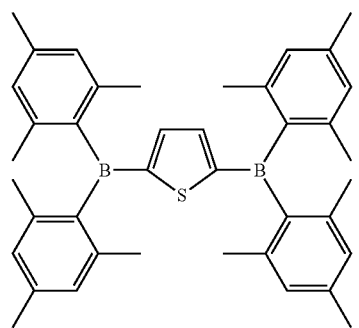 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 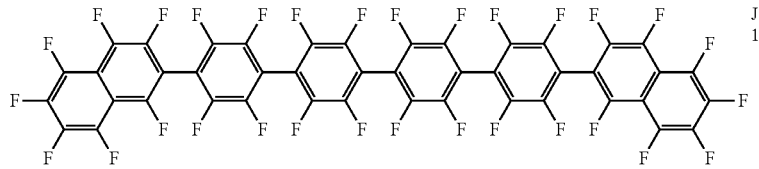 | J. Am. Chem. Soc. 122, 1832 (2000) |
| Fullerene (e.g., C60) | 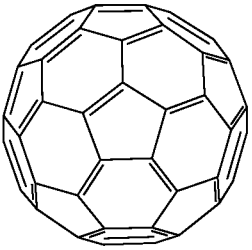 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 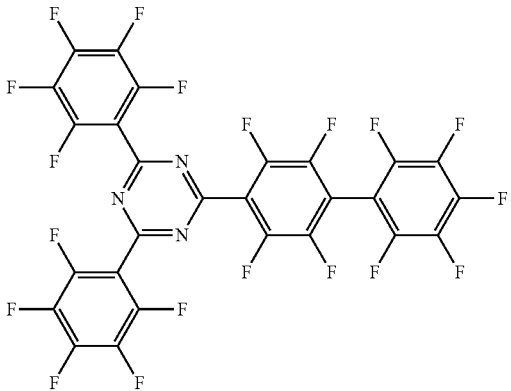 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE A-continued

| MATERIAL | EXAMPLES OF MATERIAL | PUBLICATIONS |
|---|---|---|
| Zn (N^N) complexes | 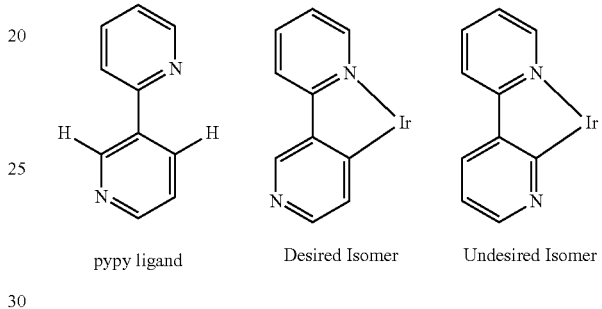 | U.S. Pat. No. 6,528,187 |

EXPERIMENTAL

Blue phosphorescent compounds with fluorine substituents, like bis[2-(4,6-difluorophenyl)pyridinato-$C^2$,N](picolinato)iridium(III) (FIrpic) or tris[2-(4,6-difluorophenyl)pyridinato-$C^2$,N]iridium(III), are known to be unstable in electroluminescent devices. Therefore, fluorine substitution is an undesirable feature on a blue emitter. Furthermore, the research leading to the compounds described herein show that non-blocked tris(pyridylpyridine) iridium compounds are desirably blue-shifted in room temperature solution and solid state thin film when compared to alkyl blocked analogues. Thus, it is believed the blue shift may be due to less steric twisting of the pyridyl-pyridine ligand resulting in less distortion in the excited state.

It has been learned that the iridium tris facial isomer with the cyclometalated pyridyl-pyridine (pypy) ligand, where the uncoordinated nitrogen is substituted para to the metal has highly desirable blue phosphorescent emission with high photoluminescent quantum yield and short excited state lifetime. The synthesis of this isomer is complicated by two factors, coordination of the free pyridine in synthesis and non-selectivity of the metalation site. Because three metalation events have to occur in the correct configuration to get the desired blue emitting isomer, finding a way to improve the synthetic yield is important.

Calculations used to develop the compounds described herein show the triplet of the undesired isomer, where the uncoordinated nitrogen is ortho to the metal, is significantly redshifted from the desired isomer. This effect is shown in Table 1 with Comparative Example 2.

The compounds described herein include blue phosphorescent emitting tris facial complexes that can employ an alkyl substitution to block metalation at the undesired site on the pyridyl pyridine ligand. Density functional calculations (DF) calculations performed using the B3LYP/cep-31g functional and basis set using a Gaussian software package show that methyl substitution has minimal effect on the triplet energy, as shown in Table 1.

TABLE 1

DFT calculations comparing the desired and undesired facial isomers to inventive compound 1.

| | Structure | HOMO (eV) | LUMO (ev) | Gap (ev) | Dipole (Debye) | $S1_{gas}$ (nm) | $T1_{gas}$ (nm) |
|---|---|---|---|---|---|---|---|
| Compound 13 | 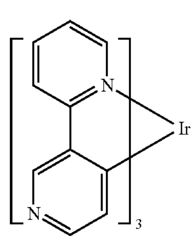 | −5.81 | −1.89 | −3.91 | 16.22 | 395 | 462 |

TABLE 1-continued

DFT calculations comparing the desired and undesired facial isomers to inventive compound 1.

| | Structure | HOMO (eV) | LUMO (ev) | Gap (ev) | Dipole (Debye) | S1$_{gas}$ (nm) | T1$_{gas}$ (nm) |
|---|---|---|---|---|---|---|---|
| Comparative Example 2 | 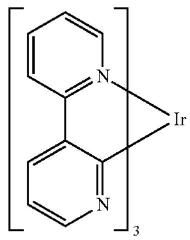 | −5.42 | −1.75 | −3.66 | 12.78 | 423 | 495 |
| Compound 1 | 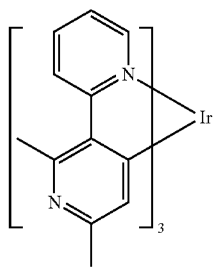 | −5.61 | −1.73 | −3.88 | 13.48 | 399 | 464 |
| Comparative Example 3 | 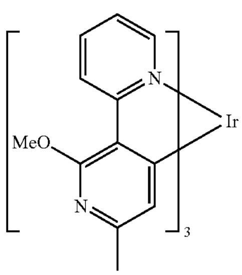 | −5.63 | −1.67 | −3.96 | 7.81 | 389 | 464 |
| Comparative Example 4 | 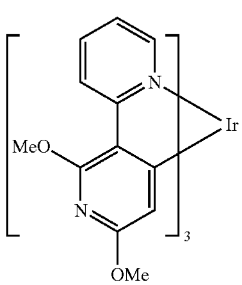 | −5.63 | −1.59 | −4.04 | 7.90 | 377 | 464 |
| Comparative Example 5 | 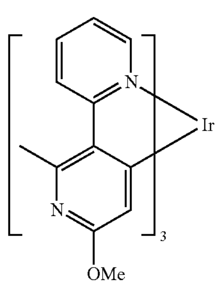 | −5.64 | −1.67 | −3.96 | 13.68 | 387 | 466 |

TABLE 1-continued

DFT calculations comparing the desired and undesired facial isomers to inventive compound 1.

| | Structure | HOMO (eV) | LUMO (ev) | Gap (ev) | Dipole (Debye) | S1$_{gas}$ (nm) | T1$_{gas}$ (nm) |
|---|---|---|---|---|---|---|---|
| Comparative Example 6 | 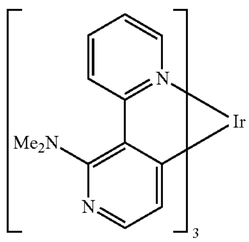 | −5.54 | −1.76 | −3.78 | 12.57 | 407 | 492 |
| Comparative Example 7 | 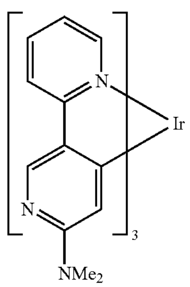 | −5.12 | −1.44 | −3.68 | 5.14 | 401 | 503 |
| Comparative Example 8 | 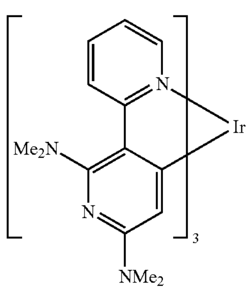 | −4.88 | −1.33 | −3.55 | 2.27 | 410 | 511 |

The compounds described herein are also compared to comparative example 1, difluoro pyridyl pyridine analogue:

Comparative Example 1

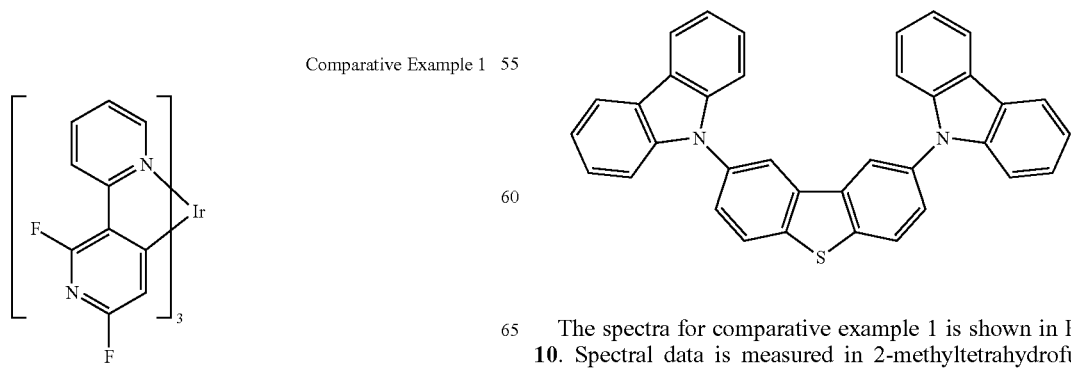

Host 3

Figure 10:
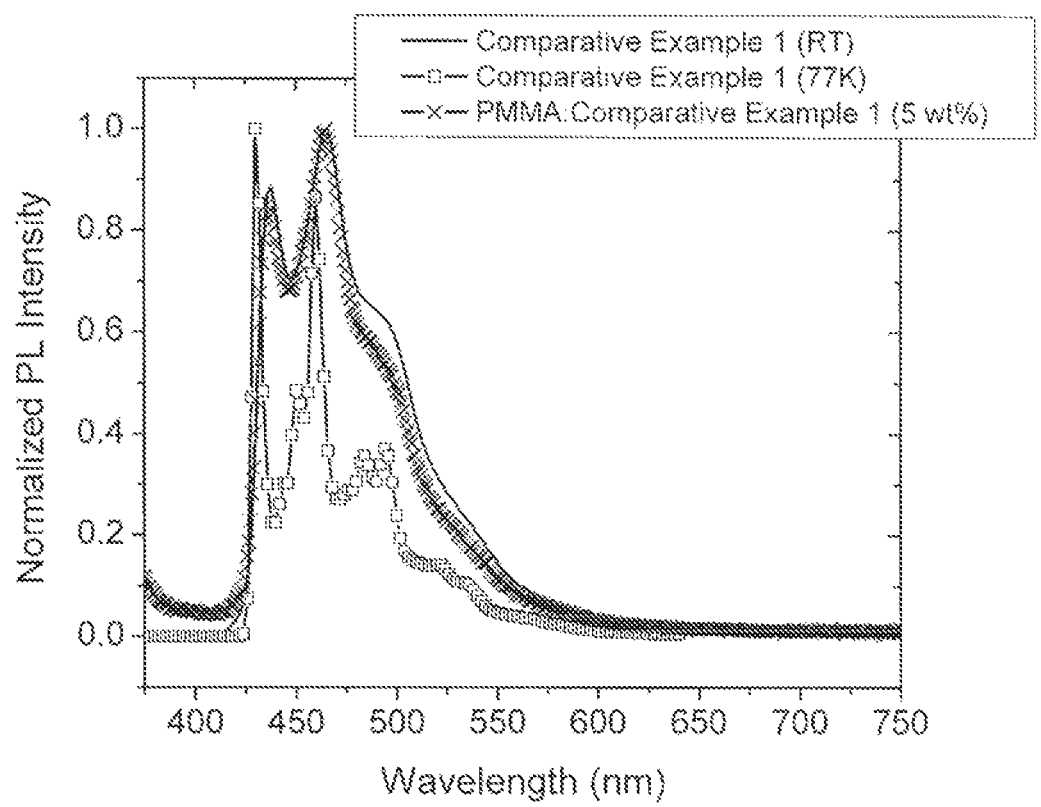
FIG. 10 shows spectral data for comparative example 1 at both room temperature (RT) and 77K in 2-methyltetrahydrofuran solvent, and polymethacrylate (PMMA) matrix at 5 wt % doping.

The spectra for comparative example 1 is shown in FIG. 10. Spectral data is measured in 2-methyltetrahydrofuran solvent at both room temperature (RT) and 77K, as well as in polymethylmethacrylate (PMMA), an optically inert polymer host matrix, at 5 weight %. At 77K, the highest energy peak is at 430 nm, and at RT and in PMMA matrix, the highest energy peak is at 437 nm. The photoluminescent quantum yield (PLQY) of the PMMA:Comparative Example 1 (5 wt %) sample was compared to PMMA:Host 3:Comparative Example 1 (5 wt %), where PMMA and Host 3 are in an approximate 50:50 ratio and Comparative Example 1 comprises 5 weight % of the total. PLQY measurements were carried out on a Hamamatsu C9920 system equipped with a xenon lamp, integrating sphere, and a model C10027 photonic multi-channel analyzer. Host 3 is a representative high triplet host comprised of standard OLED building blocks, such as, carbazole and dibenzofuran. The 77K solution triplet of Host 3 is approximately 420 nm. It is found that the PLQY for PMMA:Comparative Example 1 is very high at 95%. However, in the matrix that includes Host 3, the efficiency drops to only 9%. Therefore, the triplet of Comparative Example 1 is readily quenched by a carbazole containing OLED host material, and therefore cannot be tested and studied in standard OLED devices used with the compounds having a ligand $L_A$ of Formula I described herein.

Table 1 also compares calculated values of Compounds 1 and 13 with Comparative Examples 3 to 5. It is known in the art that compounds with an OMe group, such as those in Comparative Examples 3 to 5, can have a high triplet energy. In this case, OMe has a positive Hammett constant (($\sigma_m$=0.12, C. Hansch, et al. Chem. Rev. 1991, 91, 165-195), which actually provides an electron withdrawing effect to Ir atom. Meanwhile, with a substituent having a negative Hammett constant, i.e., an electron donating group, such as $NMe_2$ ($\sigma_m$=-0.16) in Comparative Examples 6-8, the compounds should show a red shift in the triplet energy. As shown in Table 1, this is true of Comparative Examples 6 to 8. However, Compound 1 and Compound 13 unexpectedly show that with a substituent having a small negative value or zero value of the Hammet constant, such as hydrogen ($\sigma_m$=0), or methyl ($\sigma_m$=-0.07), as well as, other alkyl analogs, the compounds can still have the same or even higher triplet energy than those having substituents with more positive or negative Hammett constants.

Synthesis of Compound 1

Step 1:

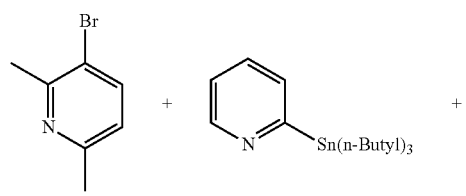

Synthesis of 2',6'-dimethyl-2,3'-bipyridine 2,6-dimethyl-3-bromopyridine (44.54 g, 240 mmol), 2-tributyltin-pyridine (82.83 g, 225 mmol) and tetrakis(triphenylphosphine)palladium(0) (6.516 g, 5.62 mmol) were charged into a reaction flask with 720 mL of m-xylene. This mixture was degassed, then heated to 130° C. for 35 hrs. The reaction mixture was cooled to room temperature. The reaction mixture was extracted with 15% aqueous HCl. The aqueous phase was first washed with ether, then neutralized by 50% NaOH aqueous solution. The aqueous phase was then extracted by chloroform. The organic layer was separated and dried over magnesium sulfate. The organics were then filtered and concentrated under vacuum. The residue was them subjected to kugelrohr distillation and yielded 2',6'-dimethyl-2,3'-bipyridine (34.52 g, 187 mmol, 83% yield).

Step 2:

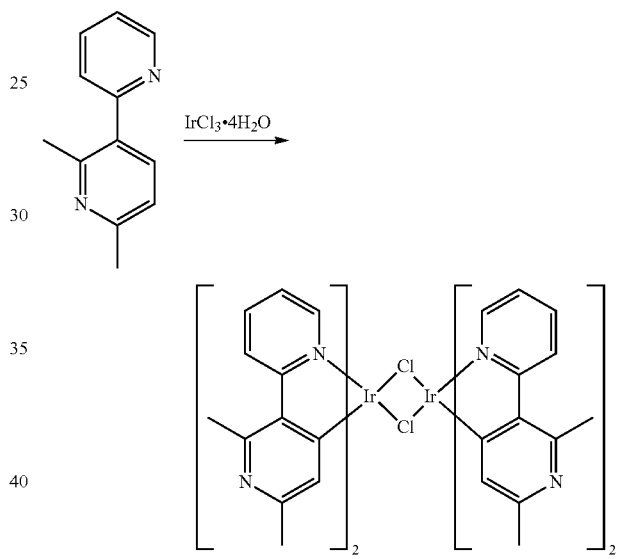

Synthesis of Iridium Chloro Bridge Dimer

A 100 ml round bottom flask was charged with 2',6'-trimethyl-2,3'-bipyridine (5 g, 27.1 mmol), $IrCl_3$ hydrate (5.032 g, 13.5 mmol), and 2-ethoxyethanol (60 ml). The reaction mixture was heated to 70° C. for 64 hrs. The desired product was isolated by filtration and washed with isopropanol. (6.94 g, 86% yield)

Step 3:

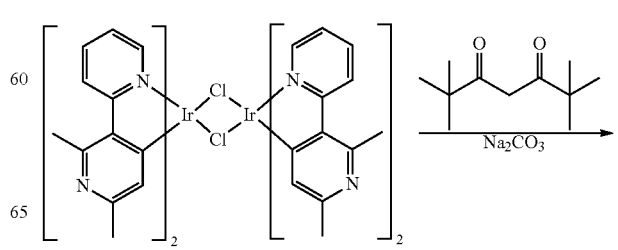

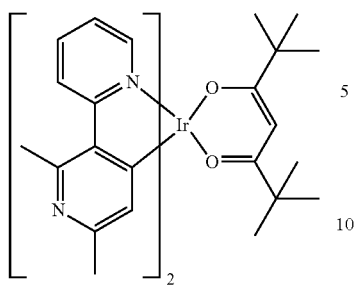

Synthesis of Iridium ACAC Complex

A 500 ml round bottom flask was charged with Iridium chloro bridge dimer from the previous step (2 g, 1.684 mmol), 2,2,6,6-tetramethylheptane-3,5-dione (1.86 g, 10.1 mmol), sodium carbonate (2.14 g, 20.2 mmol), and 2-ethoxyethanol (10 ml). The reaction mixture was stirred at room temperature for 64 hrs. The reaction mixture was diluted with water and extracted with methylene chloride. The organic layer was separated and dried over magnesium sulfate. The organics were then filtered and concentrated under vacuum and yield desired compound. (1.88 g, 2.53 mmol, 75% yield)

Step 4:

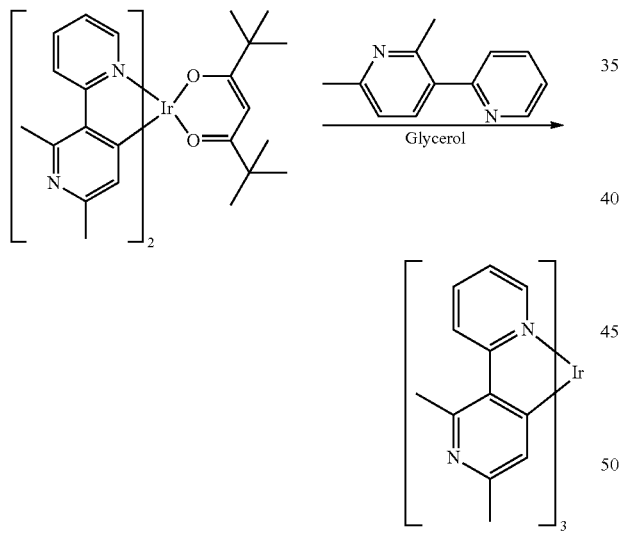

Synthesis of Compound 1

A 100 ml round bottom flask was charged with Iridium ACAC complex from the previous step (11.74 g, 15.8 mmol), 2',6'-trimethyl-2,3'-bipyridine (8.74 g, 47.5 mmol), and glycerol (10 ml). The reaction was heated to 115° C. for 89 hrs. The reaction mixture was poured into a 10% LiCl aqueous solution and extracted with dichloromethane. The organic portion was chromatographed on an Et$_3$N-pretreated silica column with 99/1 DCM/MeOH to 80/20 DCM/MeOH to give 1.0 g of a gold solid. (8.5% yield)

Synthesis of Compound 2

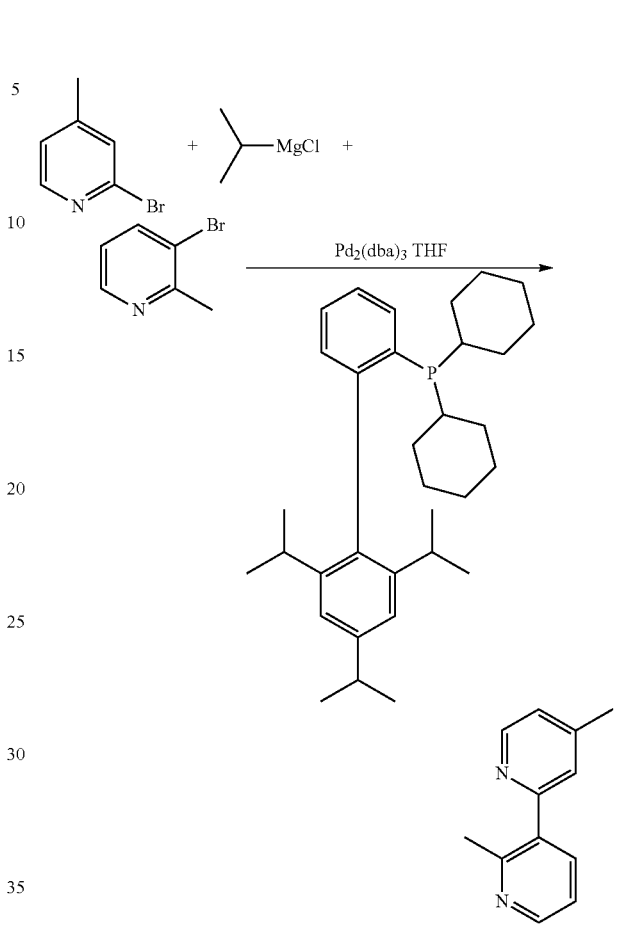

Synthesis of 2',4-dimethyl-2,3'-bipyridine

Isopropylmagnesium chloride (61.5 ml, 123 mmol) was charged into the reaction flask. 2-bromo-4-methylpyridine (16.8 g, 98 mmol) was added dropwise to this reaction mixture over a 30 minute period while maintaining the internal temperature below 30° C. This mixture was stirred at room temperature for 2 hours. Zinc chloride in tetrahydrofuran (THF) (240 ml, 120 mmol) was added dropwise to this reaction mixture over a 30 minute period while maintaining the internal temperature below 30° C. Stirring was continued overnight at room temperature. Tris(dibenzylideneacetone)palladium(0) (1.2 g, 1.311 mmol) and 2-Dicyclohexylphosphino-2',4',6'-triisopropylbiphenyl (2.4 g, 5.03 mmol) were charged into a reaction vessel with 75 mL of THF. This mixture was refluxed for 45 minutes, then was cooled to room temperature. 3-bromo-2-methylpyridine (11.4 g, 66.3 mmol) was added to the reaction mixture. The organozinc solution formed was transferred to an addition funnel and was added dropwise over 15 minutes to the reaction mixture. The mixture was degassed using nitrogen, then was heated at reflux for 18 hours. The resulting reaction mixture was cooled to room temperature, then was quenched with aqueous ammonium chloride. This mixture was extracted 2 times using 300 mL ethyl acetate. These extracts were dried over magnesium sulfate, then were filtered and concentrated under vacuum. The crude residue was passed through a neutral alumina column using 10-20% ethyl acetate/dichloromethane (DCM). 2',4-dimethyl-2,3'-bipyridine (2.2 g, 11.94 mmol, 12% yield) was isolated as an off-white solid.

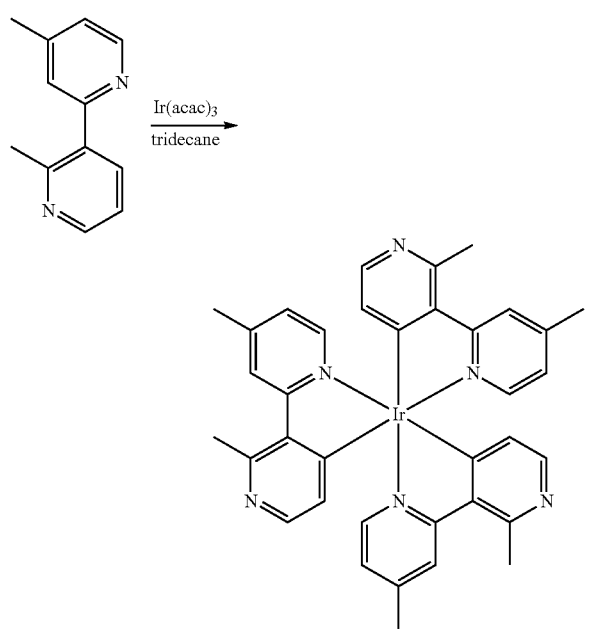

Synthesis of Compound 2

2',4-dimethyl-2,3'-bipyridine (2.7 g, 14.66 mmol) and Ir(acac)₃ (1.4 g, 2.9 mmol) were added to tridecane (0.5 mL) in a Schlenk flask and the contents were evacuated and backfilled with nitrogen five (5) times. The reaction was heated to 235° C. for 60 hours. The reaction was cooled to room temperature and chromatographed on an Et₃N-pretreated silica column with 99/1 DCM/MeOH to 80/20 DCM/MeOH to give 1.0 g of a gold solid. The solid was lixiviated with toluene followed by ether to give 0.93 g of Compound 2 as a yellow solid. The product was confirmed by NMR and LC/MS.

Synthesis of Compound 3

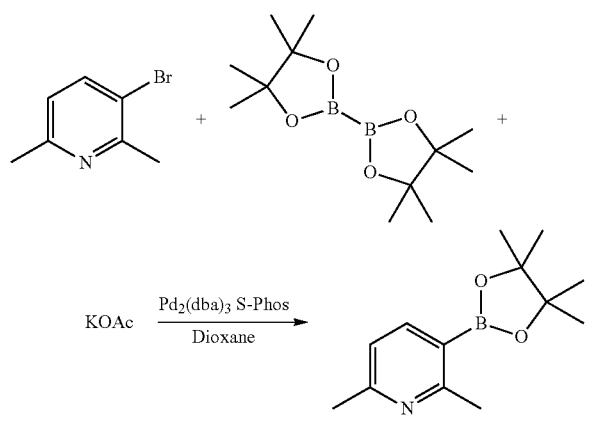

Synthesis of 2,6-dimethyl-3-(4,4,5,5-tetramethyl-1,3,2-dioxaborolan-2-yl)pyridine 3-bromo-2,6-dimethylpyridine (11 g, 59.1 mmol), 4,4,4',4',5,5,5',5'-octamethyl-2,2'-bi(1,3,2-dioxaborolane) (19.52 g, 77 mmol), Potassium acetate (6.95 g, 70.9 mmol), Tris(dibenzylideneacetone)palladium(0) (1.082 g, 1.182 mmol) and 2-dicyclohexylphosphino-2',6'dimethoxybiphenyl (1.939 g, 4.73 mmol) were charged into a reaction flask with 200 mL of dioxane. The mixture was degassed with nitrogen, then was heated at reflux overnight. The reaction mixture was cooled to room temperature, then was diluted with 300 mL of water. This mixture was extracted two times with 300 mL ethyl acetate. The organics were combined and then washed with brine. The organics were combined, were dried over magnesium sulfate, then were filtered and concentrated under vacuum. This crude residue was passed through a silica gel column using 1-20% methanol/DCM as the eluant yielding 2,6-dimethyl-3-(4,4,5,5-tetramethyl-1,3,2-dioxaborolan-2-yl)pyridine (1.2 g, 5.15 mmol, 9% yield).

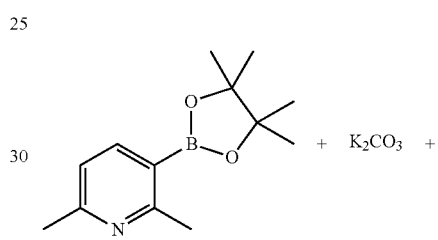

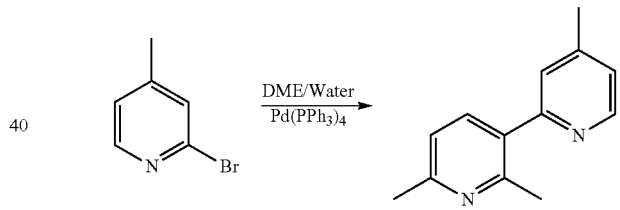

Synthesis of 2',4,6'-trimethyl-2,3'-bipyridine 2,6-dimethyl-3-(4,4,5,5-tetramethyl-1,3,2-dioxaborolan-2-yl)pyridine (1.2 g, 5.15 mmol), 2-bromo-4-methylpyridine (0.974 g, 5.66 mmol) and tetrakis(triphenylphosphine)palladium(0) (0.238 g, 0.206 mmol) were charged into the reaction flask with 50 mL of dimethoxyethane (DME). Potassium carbonate (2.131 g, 15.44 mmol) was dissolved in 10 mL of water and then charged into the reaction flask. This mixture was degassed, then was heated at reflux overnight. The reaction mixture was cooled to room temperature. The reaction mixture was diluted with 100 mL water and 200 mL ethyl acetate. The organic layer was separated and dried over magnesium sulfate. The organics were then filtered and concentrated under vacuum. The crude residue was purified via silica gel chromatography using 1-5% Methanol/DCM yielding 2',4,6'-trimethyl-2,3'-bipyridine (0.55 g, 2.77 mmol, 54% yield).

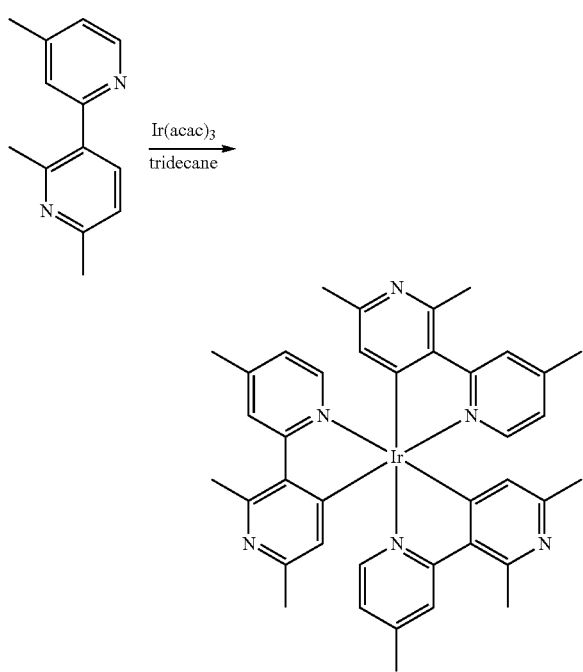

Synthesis of Compound 3

2',4,6'-trimethyl-2,3'-bipyridine (2.8 g, 13.8 mmol) and Ir(acac)₃ (1.4 g, 2.8 mmol) were added to tridecane (1 mL) in a Schlenk flask and the contents were evacuated and backfilled with nitrogen five (5) times. The reaction mixture was heated to 235° C. for 16 hours. The reaction mixture was cooled to room temperature and DCM was added. The insoluble material was filtered and washed with DCM to give 0.70 g (32%) of Compound 3 as a golden solid. The product was confirmed by NMR.

Synthesis of Compound 4

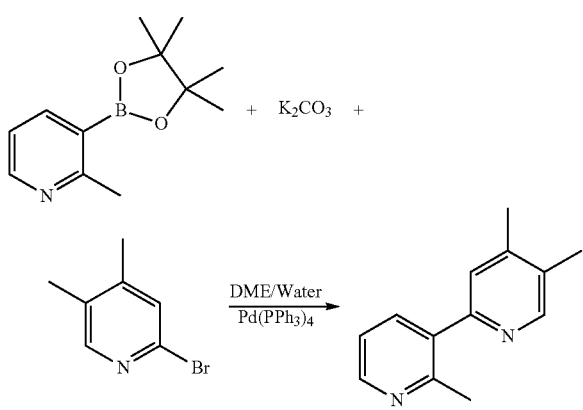

Synthesis of 2',4,5-trimethyl-2,3'-bipyridine

2-Methyl-3-(4,4,5,5-tetramethyl-1,3,2-dioxaborolan-2-yl)pyridine (1.178 g, 5.37 mmol), 2-bromo-4,5-dimethylpyridine (1 g, 5.37 mmol) and tetrakis(triphenylphosphine) palladium(0) (0.249 g, 0.215 mmol) were charged into a reaction vessel with 75 mL of toluene. Potassium carbonate (2.225 g, 16.12 mmol) was dissolved in 15 mL of water and was charged into the reaction vessel. The reaction mixture was degassed with nitrogen then was heated at reflux. The reaction mixture was heated at reflux for 3 days. The reaction mixture was then diluted with 100 mL ethyl acetate and 50 mL of water. The organic layer was separated and dried over magnesium sulfate. The organics were then filtered and concentrated under vacuum. The crude product was purified using silica gel chromatography using 1-5% methanol/DCM as the eluant. 2',4,5-trimethyl-2,3'-bipyridine (0.35 g, 1.765 mmol, 32.8% yield) was isolated as a tan solid.

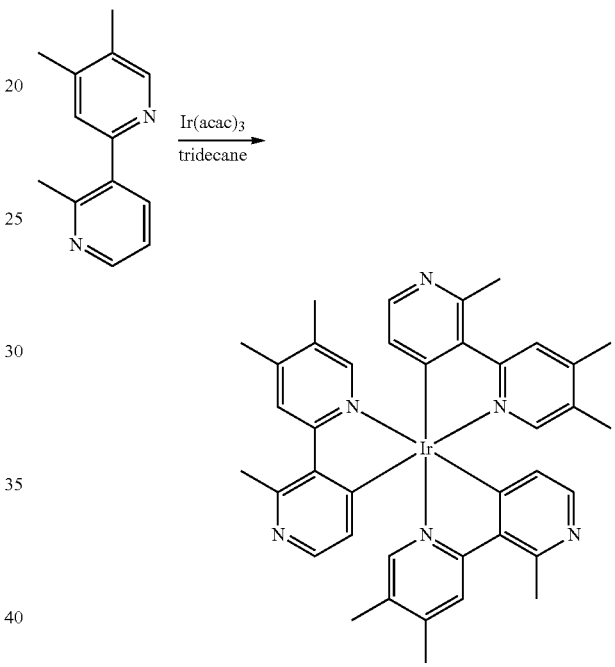

Synthesis of Compound 4

2',4,5-Trimethyl-2,3'-bipyridine (4.0 g, 20.2 mmol) and Ir(acac)₃ (2.0 g, 4.0 mmol) were added to tridecane (1 mL) in a Schlenk flask and the contents were evacuated and backfilled with nitrogen five (5) times. The reaction was heated to 255° C. for 96 hours. The reaction was cooled to room temperature and chromatographed on an Et₃N-pretreated silica column with 99/1 DCM/MeOH to 70/30 DCM/MeOH to give 1.7 g of a golden brown solid. The solid was lixiviated with toluene followed by ether to give 1.5 g of Compound 4 as a light golden solid. The product was confirmed by NMR and LC/MS.

Synthesis of Compound 5

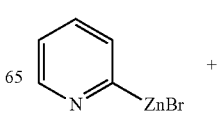

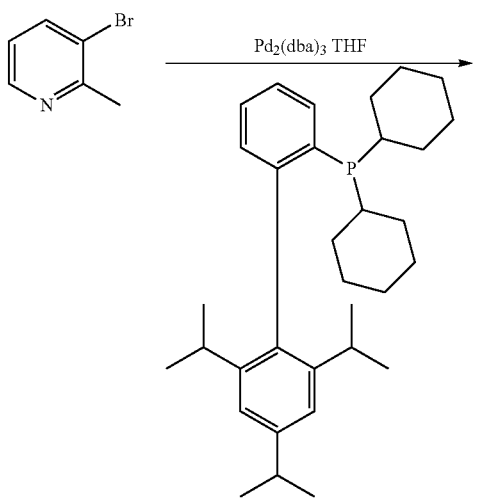

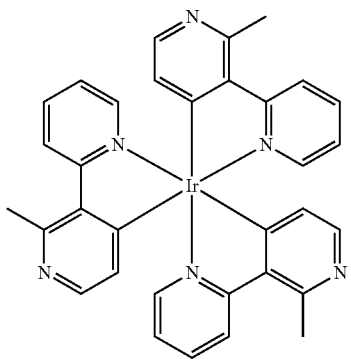

Synthesis of Compound 5

2'-methyl-2,3'-bipyridine (1.5 g, 8.8 mmol) and Ir(acac)$_3$ (0.86 g, 1.8 mmol) were added to tridecane (0.5 mL) in a Schlenk flask and the contents were evacuated and backfilled with nitrogen five (5) times. The reaction was heated to 235° C. for 60 hours. The reaction was cooled to room temperature and chromatographed on an Et$_3$N-pretreated silica column with 99/1 DCM/MeOH to 80/20 DCM/MeOH to give 0.71 g of a gold solid. The solid was lixiviated with ether to give 0.70 g of Compound 5 as a yellow solid. The product was confirmed by NMR and LC/MS.

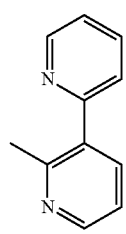

Synthesis of 2'-methyl-2,3'-bipyridine

Tris(dibenzylideneacetone)palladium(0) (0.798 g, 0.872 mmol) and 2-Dicyclohexylphosphino-2',4',6-triisopropylbiphenyl (1.664 g, 3.49 mmol) were charged into the reaction mixture with 50 mL of THF. This reaction mixture was refluxed for 45 minutes. The reaction mixture was cooled to room temperature. 3-bromo-2-methylpyridine (7.5 g, 43.6 mmol) was charged into the reaction mixture followed by the dropwise addition of pyridin-2-ylzinc(II) bromide (100 ml, 50.0 mmol). After the addition was completed, the reaction mixture was heated to reflux overnight. The reaction mixture was poured into aqueous ammonium chloride then was extracted twice using 300 mL ethyl acetate. The extracts were dried over magnesium sulfate then were filtered and concentrated under vacuum. This crude residue was passed through a neutral alumina column using 10-25% ethyl acetate/DCM. The cleaned product fractions were combined and concentrated under vacuum yielding 2'-methyl-2,3'-bipyridine (1.800 g, 10.58 mmol, 14% yield).

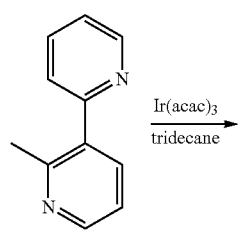

Synthesis of Compound 11

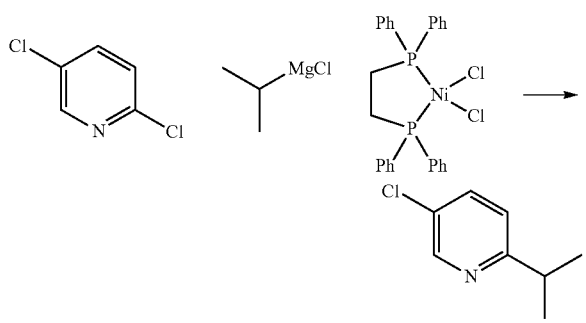

Synthesis of 5-chloro-2-isopropylpyridine 2,5-dichloropyridine (15.0 g, 101 mmol) and (dppe)NiCl2 (0.268 g, 0.507 mmol) were dissolved in dry THF (338 ml) under nitrogen, cooled by ice bath, and isopropylmagnesium chloride solution in THF (2M, 62 ml, 124 mmol) was added dropwise over half an hour, causing the mixture to turn dark brown. The mixture was stirred cold for 1 hour, then overnight at room temperature. The mixture was quenched with aqueous NH$_4$Cl, then brine and water were added. The mixture was extracted twice with ether, then the organics were washed with brine, dried, vacuumed down and coated on celite. The mixture was purified by column chromatography to yield a slightly yellow liquid, 12.61 g (80%).

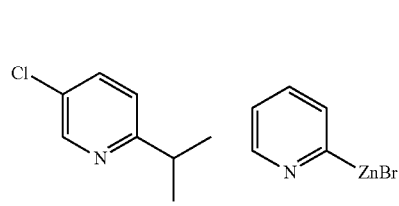
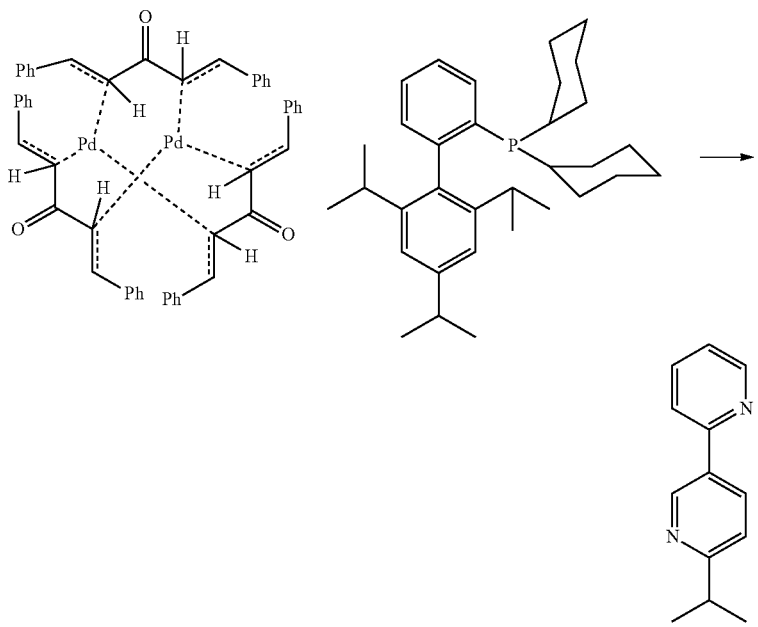

Synthesis of 6'-isopropyl-2,3'-bipyridine

Pd$_2$(dba)$_3$ (0.944 g, 1.031 mmol) and X-Phos (1.965 g, 4.12 mmol) were dissolved in THF (150 ml) under nitrogen, heated to reflux until orange, then added via cannula to a solution of 5-chloro-2-isopropylpyridine (8.02 g, 51.5 mmol) in THF (50 ml). The mixture was warmed to 65° C. for about 5 minutes, then pyridin-2-ylzinc(II) bromide solution in THF (0.5 M, 113 ml, 56.7 mmol) was slowly added via syringe. The brown mixture was heated at very gently refluxed for 4 hours, resulting in the formation of solids. The reaction solution was diluted with 250 mL EtOAc and filtered through celite. The solvent was removed under vacuum. The residue was partitioned between EtOAc and water, and the pH was brought to ~9 using K$_2$CO$_3$. The thick emulsion was filtered through celite, separated, and the aqueous layer was extracted several times more with EtOAc. The organics were washed with brine, dried, vacuumed down and coated on celite. The product was purified by column chromatography, yielding a yellow/brown oil which was distilled via kugelrohr), yielding a colorless oil, 8.06 g (79%).

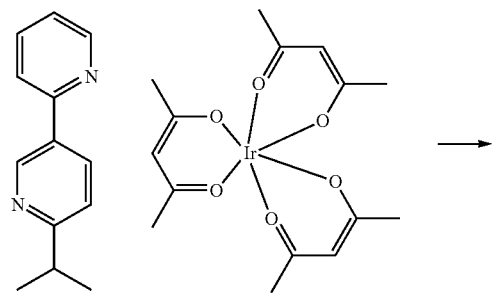
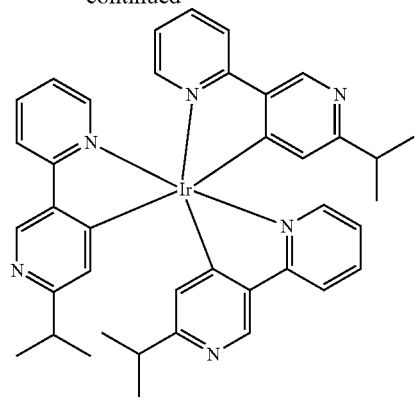

Synthesis of Compound 11

6'-isopropyl-2,3'-bipyridine (8.00 g, 40.3 mmol), Ir(acac)$_3$ (3.95 g, 8.07 mmol), and tridecane (1 ml) were combined in a schlenk tube, and the mixture was degassed by cycling vacuum/nitrogen several times. The mixture was heated at ~260° C. under nitrogen for 4 days, then a gentle vacuum was applied while the solution was still hot to remove tridecane. The residual mixture was heated at 270° C. overnight, resulting in blue luminescence. After cooling to room temperature, the reaction mixture was dissolved in DCM, transferred to a kugelrohr flask and excess ligand was distilled off. The residue was purified by column chromatography and the residue from the cleanest fraction was triturated in ~100 mL hot EtOAc, cooled to RT and filtered, and washed with lots of EtOAc. The product was dried to give 0.936 g of dark yellow powder. This material was boiled in ~100 mL EtOAc, cooled to RT, and insoluble, beige solids were filtered out. The yellow filtrate was condensed, dissolved again in 100 mL hot EtOAc, cooled to RT, then ~100 mL of heptanes were added and the resulting solution was stirred at RT. The resulting material collected was 0.550 g of yellow solid.

Synthesis of Compound 12

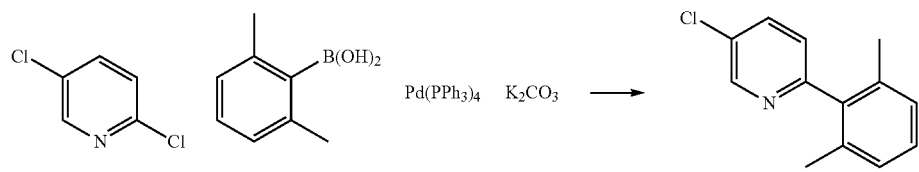

Synthesis of 5-chloro-2-(2,6-dimethylphenyl)pyridine 2,5-dichloropyridine (10 g, 67.6 mmol), (2,6-dimethylphenyl)boronic acid (11.15 g, 74.3 mmol), and potassium carbonate (14.01 g, 101 mmol) were combined in dioxane (113 ml) and water (113 ml), degassed for 30 minutes, then Pd(PPh$_3$)$_4$ (3.90 g, 3.38 mmol) was added. Degassing was continued another 10 minutes, then the mixture was heated to reflux under nitrogen with stirring to produce a homogeneous reaction mixture. The reaction was heated overnight, then partitioned between water and EtOAc. The organics were washed with brine, dried, and coated on celite. Column chromatography yielded a nearly colorless oil, 10.99 g (75%).

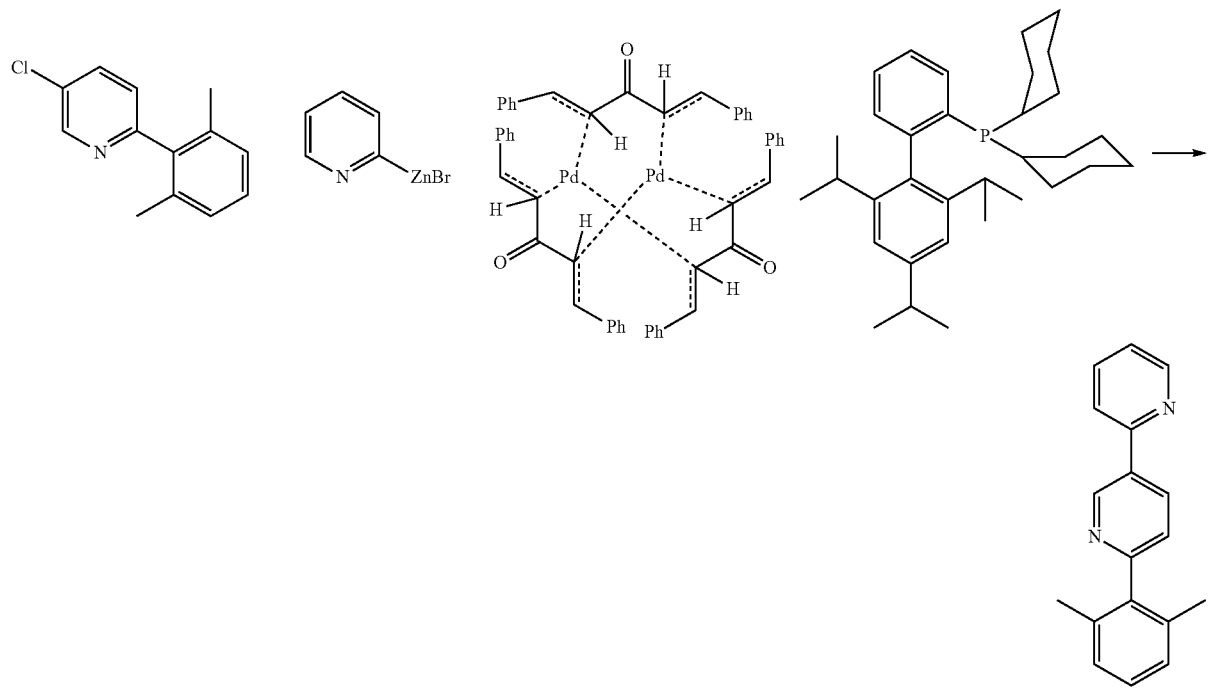

Synthesis of 6'-(2,6-dimethylphenyl)-2,3'-bipyridine

Pd$_2$(dba)$_3$ (0.925 g, 1.010 mmol) and X-Phos (1.925 g, 4.04 mmol) were stirred in THF (150 ml) under nitrogen, heated to reflux until orange (10 min), cooled to room temperature, then added via cannula to a solution of 5-chloro-2-(2,6-dimethylphenyl)pyridine (10.99 g, 50.5 mmol) in THF (50 ml). Pyridin-2-ylzinc(II) bromide solution in THF (0.5 M, 111 ml, 55.5 mmol) was added via syringe, and the resulting brown mixture was heated at gentle reflux for 4 hours then cooled to room temperature. Most of the THF was removed under vacuum and the residue was diluted with EtOAc and filtered through celite. Water was then added, the pH was brought to ~9 with Na$_2$CO$_3$. The suspension was filtered through celite, partitioned and the aqueous layer was extracted with 2×EtOAc. The organics were washed with brine, dried, vacuumed down and coated on celite. Column chromatography yielded a yellow/brown oil that was distilled using a kugelrohr to yield a colorless, tacky oil. Acidification using HCl in dioxane, followed by trituration three times of the HCl salt in hot acetone yielded a more pure solid that was basified using NaOH and extracted into ether, yielding a colorless oil of approximately 99% purity, 6.09 g (46%).

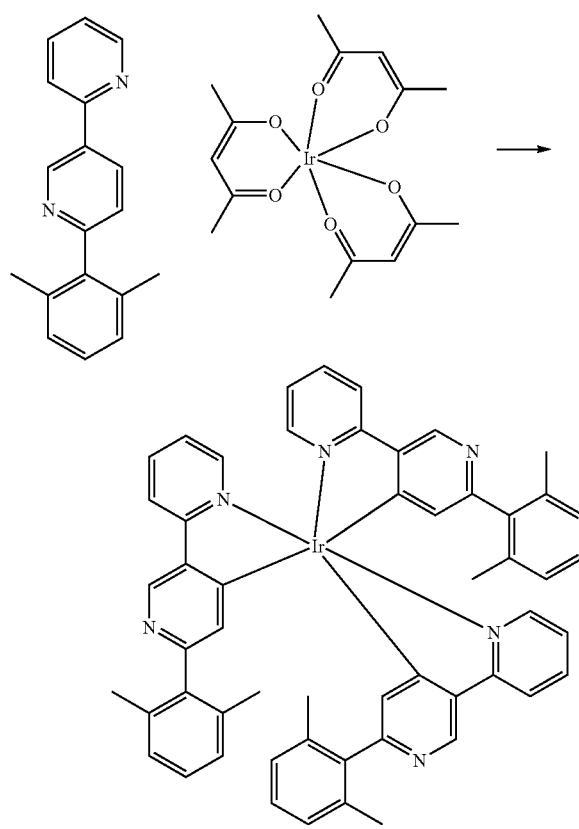

Synthesis of Compound 12

6'-(2,6-dimethylphenyl)-2,3'-bipyridine (6.07 g, 23.32 mmol), Ir(acac)$_3$ (2.24 g, 4.58 mmol), and 10 drops of tridecane were combined in a schlenk tube, which was cycled several times through vacuum/nitrogen backfill, then heated the 270° C. under nitrogen. The reaction solution turned dark brown overnight. In the morning, the mixture was cooled to 160° C. and held under vacuum until most bubbling had subsided. The mixture was heated at 270° C. for five days more, then cooled and coated on celite. Column chromatography followed by trituration in boiling EtOAc yielded a shiny yellow solid, 0.865 g.

Synthesis of Compound 13

Synthesis of 2,3'-bipyridine

Pd$_2$(dba)$_3$ (1.129 g, 1.233 mmol), S-Phos (2.025 g, 4.93 mmol), pyridin-3-ylboronic acid (8.34 g, 67.8 mmol), and potassium phosphate (26.2 g, 123 mmol) were combined in a flask, degassed by vacuum/backfill, then a degassed mixture of dioxane (205 ml) and water (103 ml) was added via cannula, and 2-chloropyridine (5.79 ml, 61.6 mmol) was added via syringe. The mixture was heated at 100° C. for 3 hours and cooled to room temperature. Brine and EtOAc were added and, after separation, the aqueous layer was extracted three times with EtOAc. The combined organic layers were washed with brine, dried, the solvent was removed, and residue was coated on celite. Column chromatography yielded a yellow oil that was distilled under vacuum (bath: 200° C.; vapor: 162° C.), yielding 8.50 g (88%) of colorless oil.

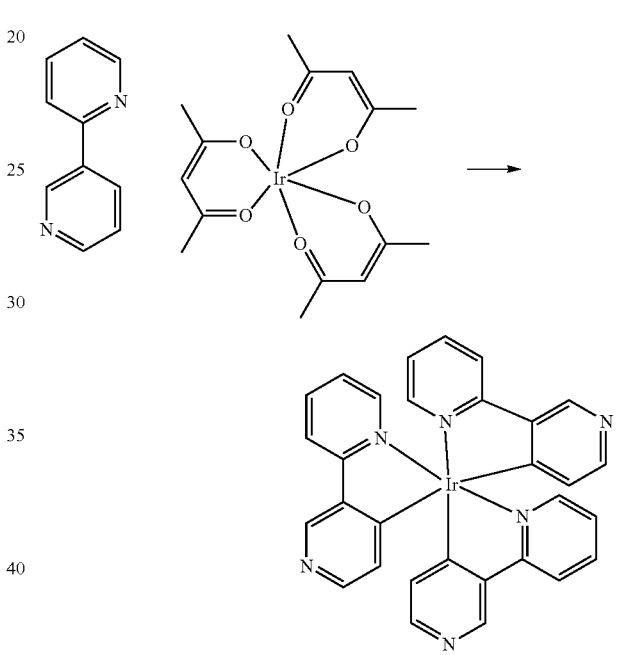

Synthesis of Compound 13

2,3'-bipyridine (6.99 g, 44.7 mmol), Ir(acac)$_3$ (4.38 g, 8.95 mmol), and 10 drops of tridecane were combined in a schlenk tube, cycled with vacuum/nitrogen several times,

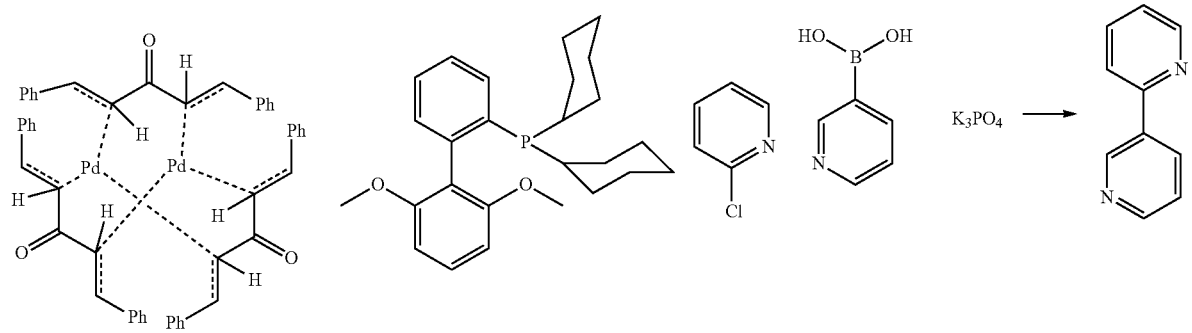

then heated to ~275° C. (active reflux) under nitrogen. The reaction solution turned homogeneous and brown quickly once at temperature. In the morning, the mixture was heated at 160° C. under active vacuum for several hours, then heating was continued at 275° C. over the weekend under nitrogen. After cooling to room temperature, the reaction mixture was dissolved in ~50 mL DCM, diluted with heptanes, and filtered through a celite pad and washed with lots of heptanes. The filtrates were vacuumed down, then dissolved again in a couple mL of DCM, diluted with heptanes and washed again through the same celite pad, washing with heptanes. The celite cake was loaded onto a silica column and subsequent chromatography yielded 0.87 g of material which was triturated in 250 mL hot EtOAc to yield 0.84 g of yellow powder.

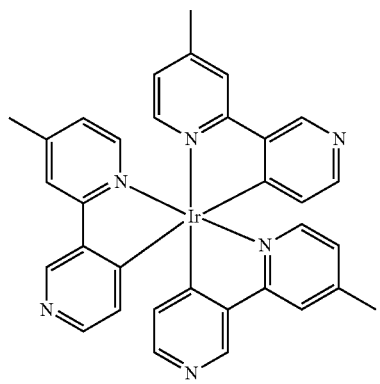

Synthesis of Compound 14

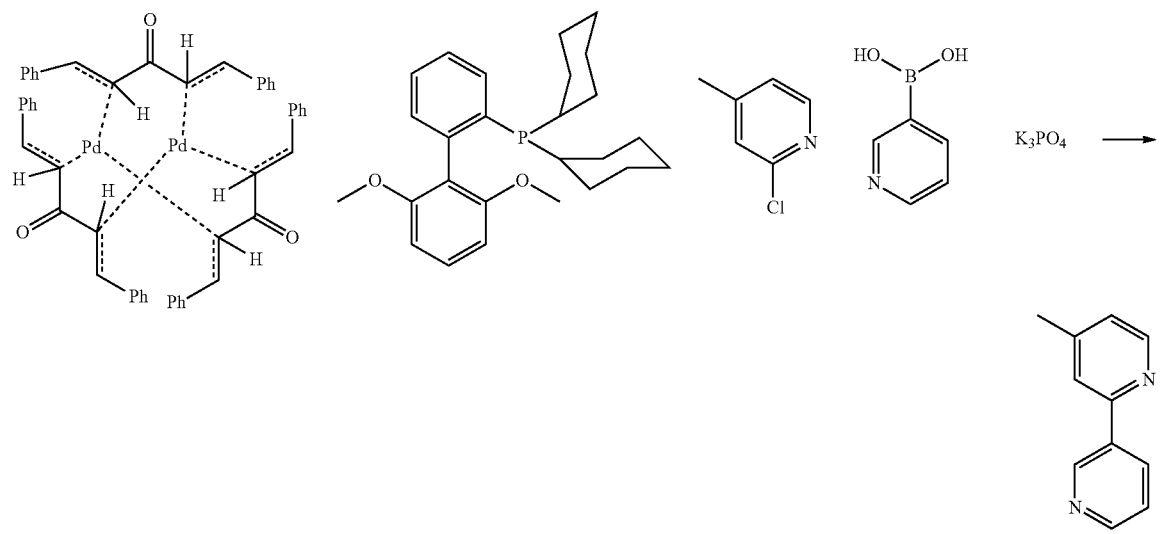

Synthesis of 4-methyl-2,3'-bipyridine

Pd$_2$(dba)$_3$ (1.279 g, 1.396 mmol), S-Phos (2.293 g, 5.59 mmol), pyridin-3-ylboronic acid (9.44 g, 77 mmol), and potassium phosphate (29.6 g, 140 mmol) were combined in a flask, degassed by vacuum/backfill, then a degassed mixture of dioxane (233 ml) and water (116 ml) was added via cannula, and 2-chloro-4-methylpyridine (7.8 ml, 69.8 mmol) was added via syringe. The mixture was heated at 100° C. overnight. After cooling to room temperature, brine and EtOAc were added. After separation, the aqueous layer was extracted three times with EtOAc, the combined organic layers were washed with brine, dried, vacuumed down, and coated on celite. Column chromatography yielded a yellow oil that was distilled under vacuum (sand bath: 270° C.; vapor: ~190° C.), yielding 10.98 g (92%) of a colorless oil.

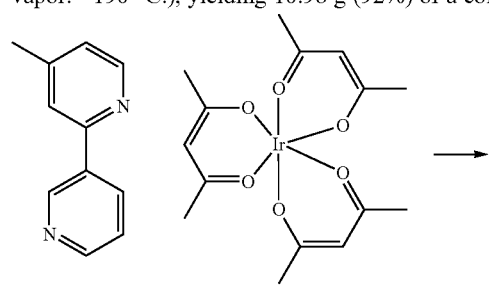

Synthesis of Compound 14

4-methyl-2,3'-bipyridine (8.28 g, 48.6 mmol), Ir(acac)$_3$ (4.76 g, 9.72 mmol), and 10 drops of tridecane were combined in a schlenk tube, degassed with several long vacuum/nitrogen backfill cycles. The mixture was heated to 100° C. while stirring under vacuum for a last degassing, then backfilled with nitrogen, and heated at 270° C. overnight. After one day, the mixture was heated at 160° C. under vacuum for several hours, then heated again at 275° C. for an additional 5 days. The mixture was cooled to room temperature and coated on celite using DCM/MeOH. Column chromatography followed by trituration in EtOAc yielded 0.71 g of yellow solid.

Photoluminescent (PL) Spectra

Figure 4:
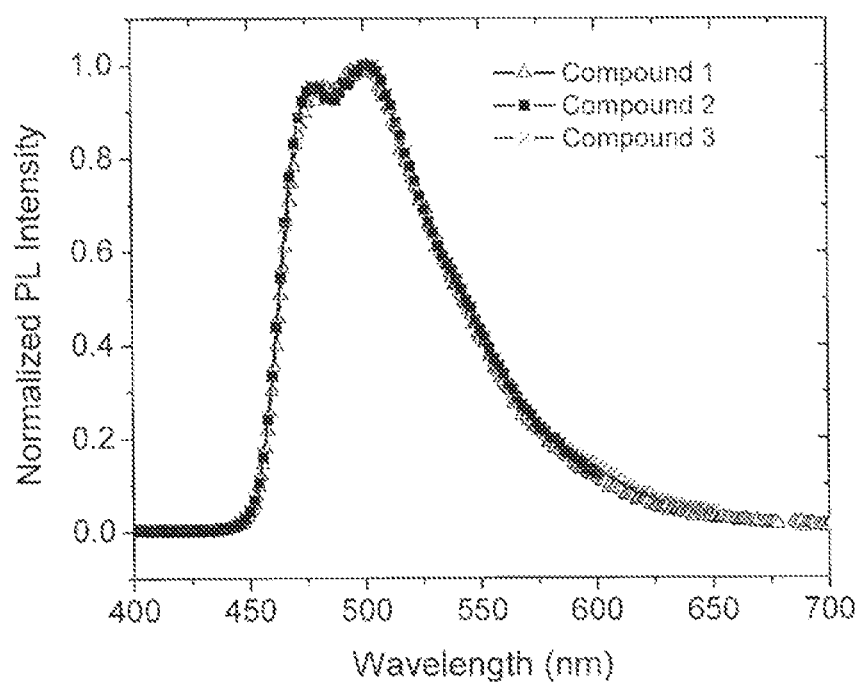
FIG. 4 shows room temperature emission spectra of Compound 1-3 in 2-methyltetrahydrofuran solvent.
Figure 5:
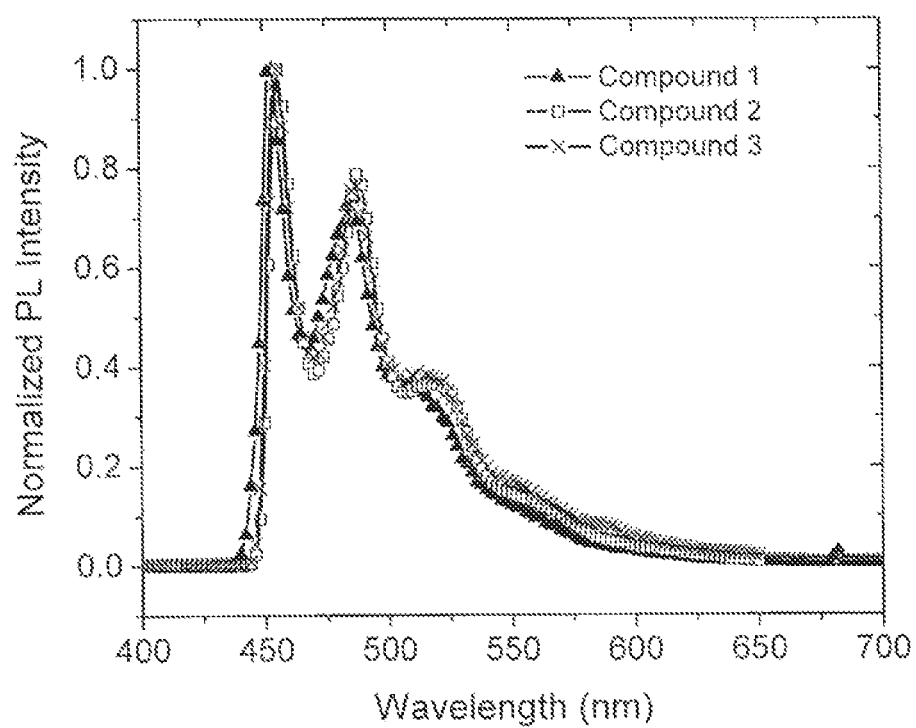
FIG. 5 shows 77K emission spectra of Compound 1-3 in 2-methyltetrahydrofuran solvent.

The emission spectra of Compounds 1-3 are shown in FIGS. 4 and 5. It can be seen in FIG. 4 that the compounds emit at room temperature with blue-green color with a highest energy emission peak around 475 nm. FIG. 5 shows the emission at 77K. Here the intrinsic deep blue triplet energy is demonstrated for this family of compounds with emission maxima between 452-456 nm.

The compounds also emit at 77K with a very short excited state lifetime. For example Compound 1 and 3 have excited state lifetimes of 2.95 and 2.52 microseconds, respectively. For comparison, the tris facial iridium phenylpyridine green emitting compound fac-Ir(ppy)$_3$ was measured to have a lifetime of 4.03 microseconds in 77K 2-methyltetrahydrofuran. The short excited state lifetime may be a desirable feature for improved stability as the compound spends less time in the highly energetic excited state.

Figure 6:
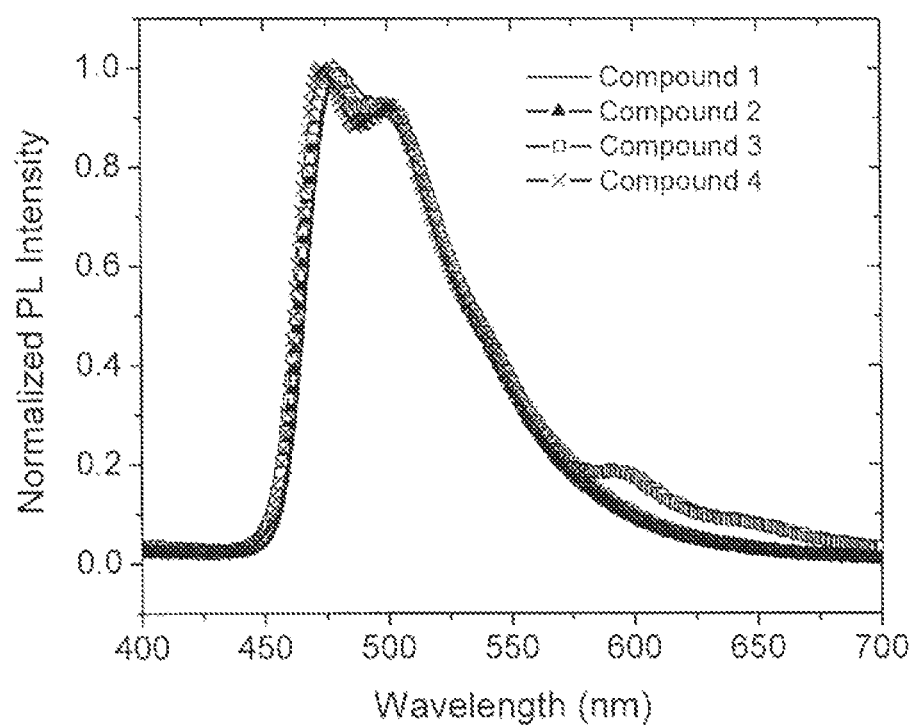
FIG. 6 shows thin film emission spectra for Compounds 1-4 doped into Host 1 at 5 wt % on quartz substrate.
Figure 7:
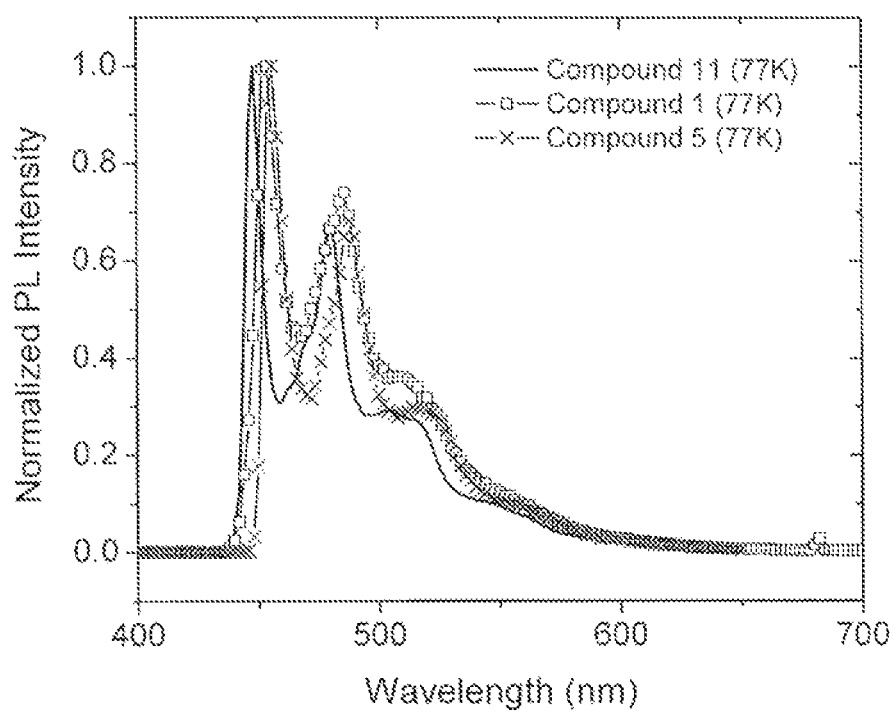
FIG. 7 shows 77K emission spectra of Compound 1, 5 and 11. Emission spectra were measured in 2-methyltetrahydrofuran solvent.
Figure 8:
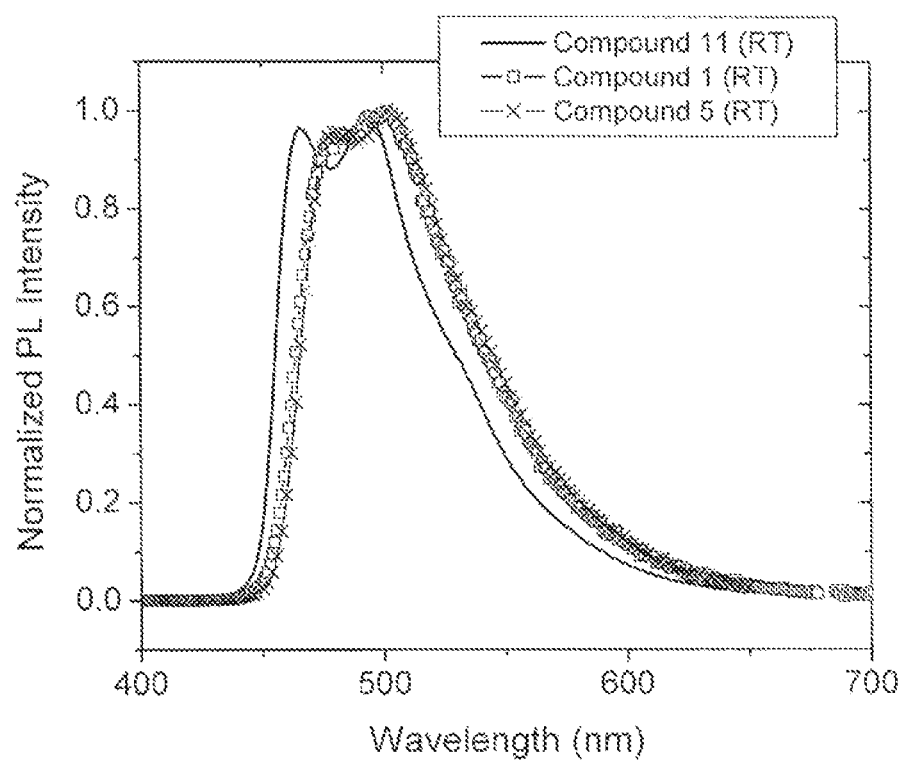
FIG. 8 shows room temperature emission spectra for Compound 1, 5 and 1. Emission spectra were measured in 2-methyltetrahydrofuran solvent.
Figure 9:
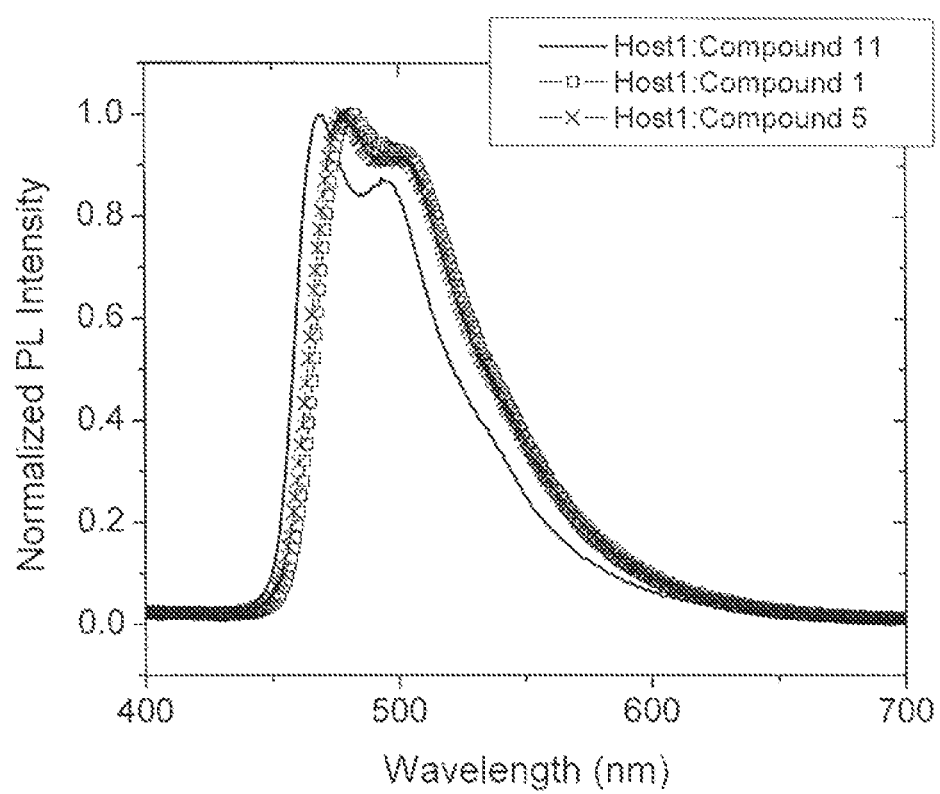
FIG. 9 shows emission spectra for Compound 1, 5 and 11 doped at 5 wt % in Host 1 on quartz substrate.

The compounds are also measured to have a very high photoluminescent quantum yield when doped in a host matrix. Thin film samples of Compounds 1-4 were prepared where Compounds 1-4 were doped into Host 1 at 5 weight % on a quartz substrate. Thin film photoluminescent quantum yields for compounds 1-5 were 92%, 87%, 69%, 90%, and 94% respectively, demonstrating that these compounds are very efficient emitters. Emission spectra for the doped films are shown in FIG. 6. It can be seen that the blue emission properties improve in the doped film compared to room temperature solution spectra shown in FIG. 4. Here the highest energy peak is now the highest intensity peak resulting in a more blue emission color.

Device Examples

-continued

Host 2

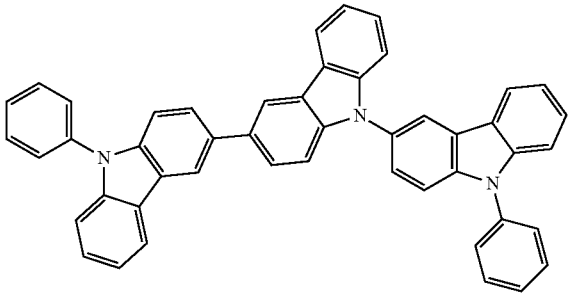

Host 1

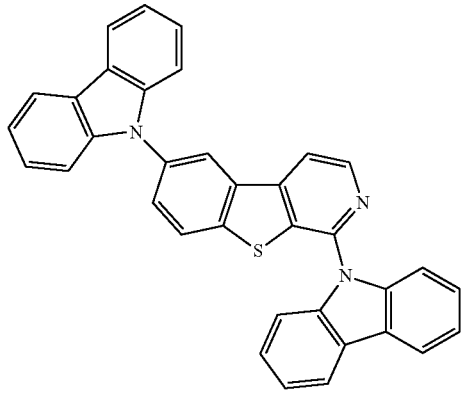

Devices were fabricated by high vacuum (<10$^{-7}$ Torr) thermal evaporation. The anode electrode is 800 Å of indium tin oxide (ITO). The cathode was formed of 10 Å of LiF followed by 1000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package. LG101 was purchased from LG Chemical.

TABLE 2

VTE device architecture.

| | LG101 (Å) | NPD (Å) | Host 2 (Å) | EML | Host 1 (Å) | AlQ$_3$ (Å) |
|---|---|---|---|---|---|---|
| Device 1 | 100 | 300 | 50 | Host1:Host2:Compound 4 (70, 25, 5%), 300 Å | 50 | 400 |
| Device 2 | 100 | 300 | 50 | Host1:Host2:Compound 4 (70, 25, 5%), 300 Å | 50 | 450 |
| Device 3 | 100 | 1400 | 50 | Host1:Host2:Compound 4 (70, 25, 5%), 300 Å | 50 | 400 |
| Device 4 | 100 | 1400 | 50 | Host1:Host2:Compound 4 (70, 25, 5%), 300 Å | 50 | 450 |
| Device 5 | 100 | 300 | 50 | Host1:Host2:Compound 12 (70, 25, 5%), 300 Å | 50 | 400 |
| Device 6 | 100 | 300 | 50 | Host1:Host2:Compound 13 (80, 15, 5%), 300 Å | 50 | 400 |
| Device 7 | 100 | 300 | 50 | Host1:Host2:Compound 14 (80, 15, 5%), 300 Å | 50 | 400 |

TABLE 3

VTE Device Data

| | 1931 CIE | | λ max | FWHM | At 1000 nits | | | | 20 mA/cm$^2$ |
| | | | | | Voltage | LE | EQE | PE | Lo |
| Device# | X | Y | (nm) | (nm) | (V) | (Cd/A) | (%) | lm/W | (nits) |
|---|---|---|---|---|---|---|---|---|---|
| 1 | 0.182 | 0.419 | 502 | 72 | 4.3 | 38.0 | 16.2 | 27.8 | 6910 |
| 2 | 0.190 | 0.437 | 502 | 74 | 5.0 | 38.1 | 15.6 | 24.1 | 6831 |
| 3 | 0.180 | 0.373 | 474 | 58 | 4.7 | 30.3 | 14.2 | 20.4 | 5576 |
| 4 | 0.181 | 0.383 | 474 | 58 | 5.3 | 30.4 | 13.9 | 18.0 | 5563 |
| 5 | 0.169 | 0.378 | 474 | 62 | 5.6 | 17.6 | 8.1 | 9.9 | 3536 |

TABLE 3-continued

| | | | | | At 1000 nits | | | 20 mA/cm² |
| | 1931 CIE | | λ max | FWHM | Voltage | LE | EQE | PE | Lo |
| Device# | X | Y | (nm) | (nm) | (V) | (Cd/A) | (%) | lm/W | (nits) |
| --- | --- | --- | --- | --- | --- | --- | --- | --- | --- |
| 6 | 0.163 | 0.367 | 496 | 68 | 4.9 | 24.5 | 11.3 | 15.7 | 4581 |
| 7 | 0.160 | 0.334 | 468 | 66 | 4.9 | 23.8 | 11.7 | 15.3 | 4350 |

Devices 1-7 were fabricated in order to demonstrate saturated blue emission from pyridyl-pyridine dopants in an OLED device. All devices employ a two host emissive layer comprised of an electron transporting Host 1 and a hole transporting Host 2. Devices 1-4 are doped with Compound 4, which has a methyl blocking substituent on the covalently attached pyridine ring. Device 1 was found to have the highest efficiency, with an external quantum efficiency of 16.2% at 1000 nits and brightness of 6910 cd/m² at 20 mA/cm². Compounds 12-14, used in Devices 5-7, do not have a methyl blocking substituent, and are found to have blue shifted emission color in the device. Of these examples, Device 7 (Compound 14) is found to have the bluest electroluminescent spectrum with CIE coordinates of (0.160, 0.334) and a lambda max of 468 nm.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having the formula $Ir(L_A)_m(L_B)_n$, wherein $L_B$ is a different ligand from $L_A$;

wherein m ranges from 1 to 3, n ranges from 0 to 2, and m+n=3;

wherein the ligand $L_A$ and, when present, $L_B$ are coordinated to the Ir;

wherein the ligand $L_A$ is optionally linked with one or both of the other $L_A$ or $L_B$ ligands to comprise a tetradentate or hexadentate ligand;

wherein $L_A$ is selected from the group consisting of

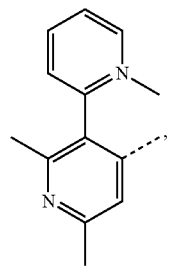

$L_{A1}$

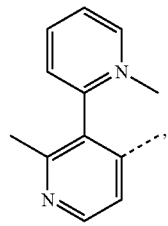

$L_{A2}$

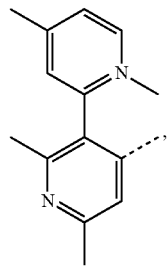

$L_{A3}$

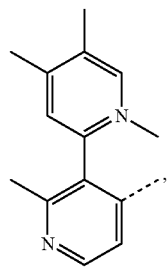

$L_{A4}$

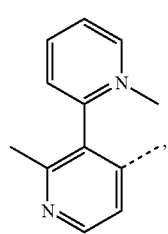

$L_{A5}$

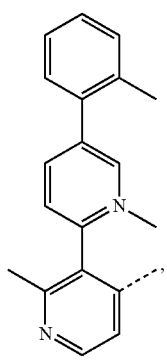
$L_{A6}$
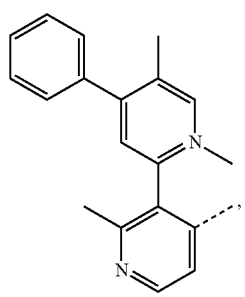
$L_{A7}$
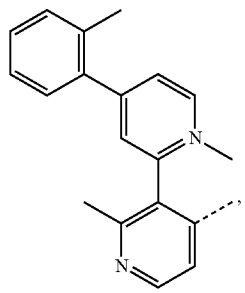
$L_{A8}$
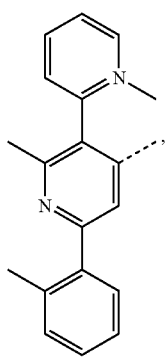
$L_{A9}$
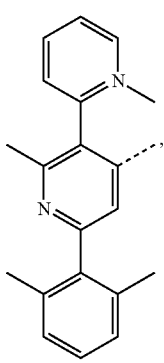
$L_{A10}$
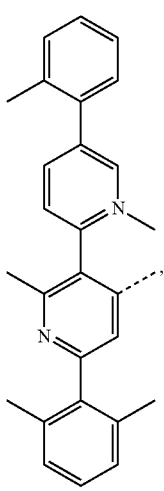
$L_{A19}$
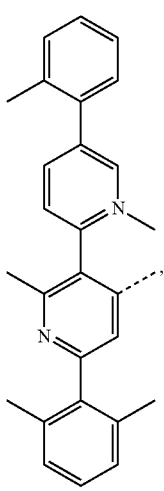
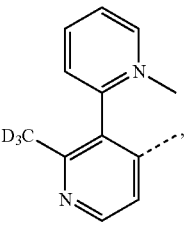
$L_{A21}$
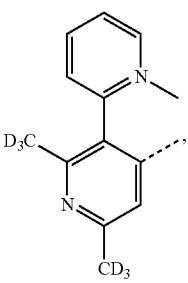
$L_{A22}$
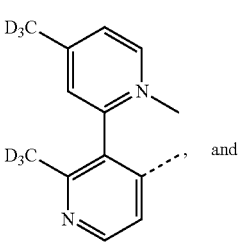
$L_{A23}$
and

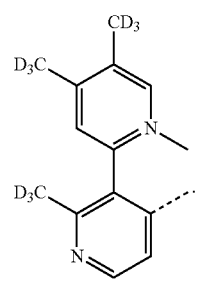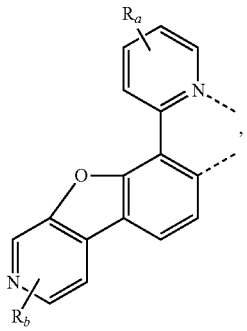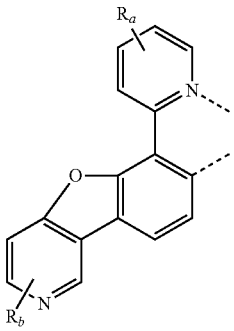
wherein, when m is 1 or 2, $L_B$ is selected from the group consisting of:
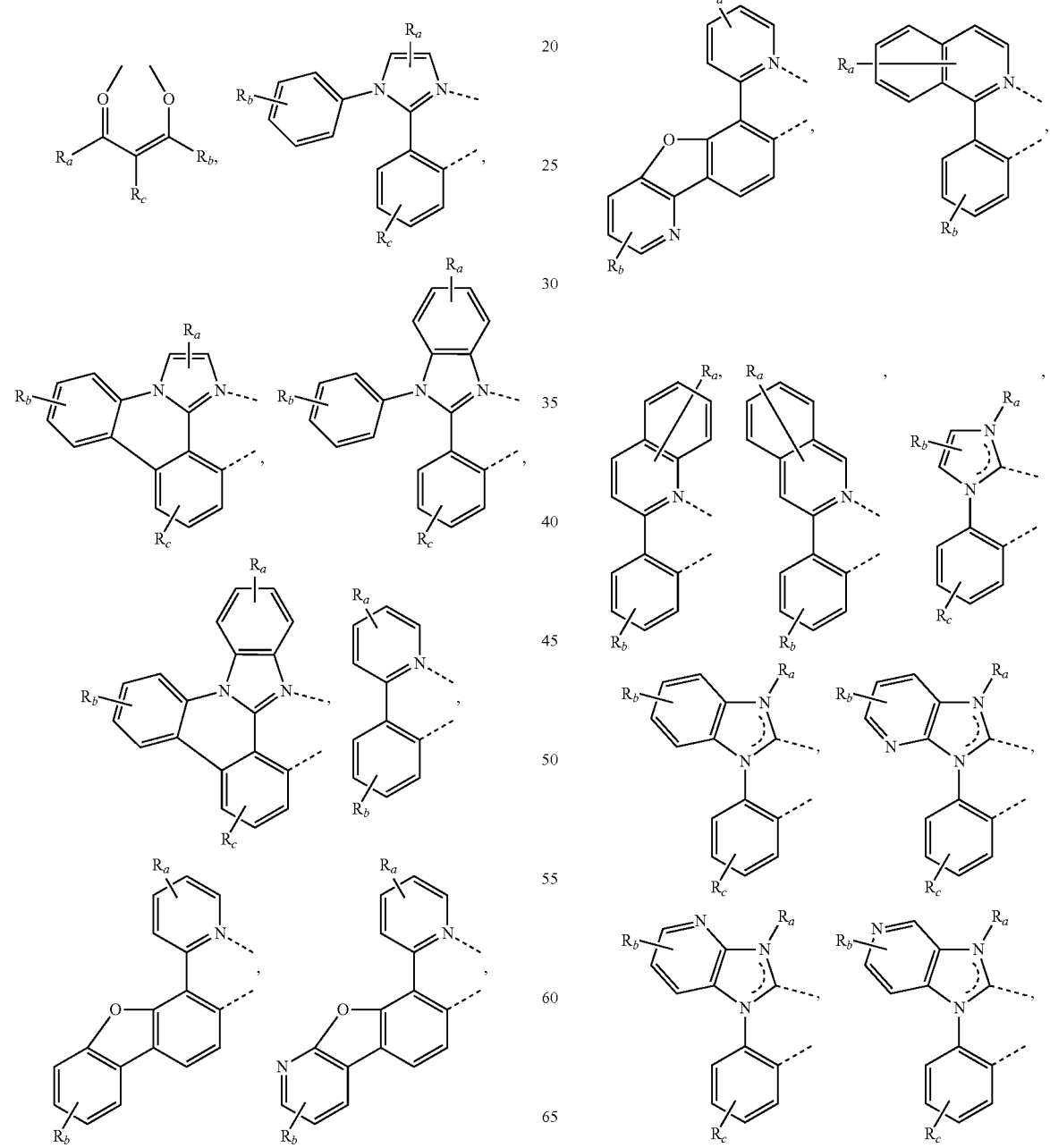

-continued

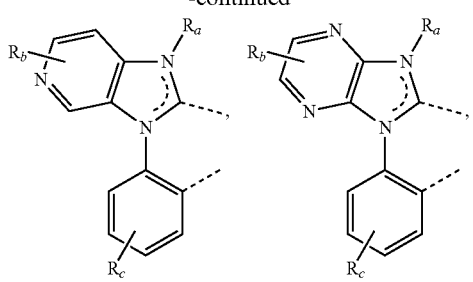

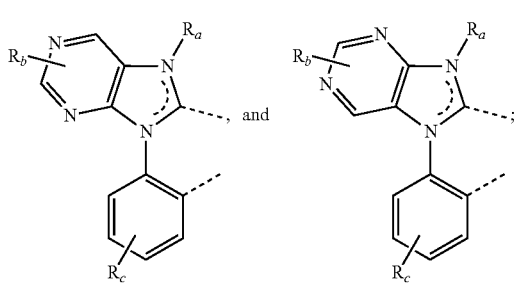

wherein $R_a$, $R_b$, and $R_c$ may represent mono, di, tri, or tetra substitution, or no substitution;

wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and $R_c$ are optionally joined to form a fused ring or form a multidentate ligand.

2. The compound of claim 1, wherein $L_A$ is bidentate and is not linked with other ligands.

3. The compound of claim 1, wherein the compound is heteroleptic.

4. The compound of claim 1, wherein the compound has a fac configuration.

5. The compound of claim 1, wherein the compound is homoleptic.

6. The compound of claim 1, wherein the compound is selected from the group consisting of:

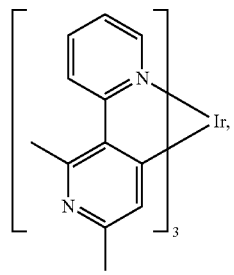

Compound 1

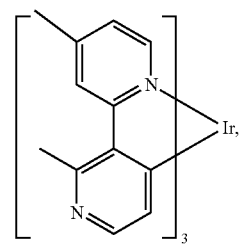

Compound 2

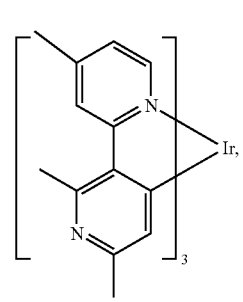

Compound 3

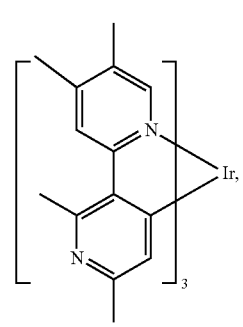

Compound 4

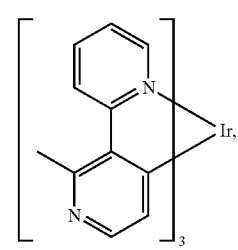

Compound 5

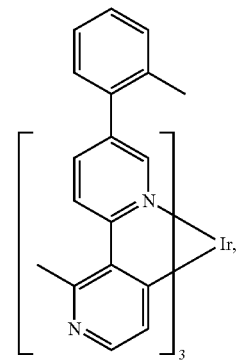

Compound 6

Compound 7
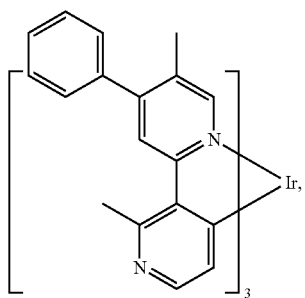
Compound 8
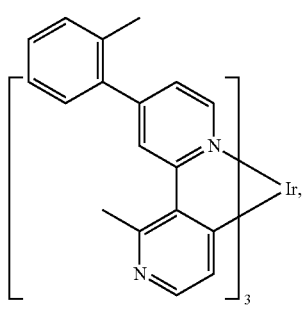
Compound 9
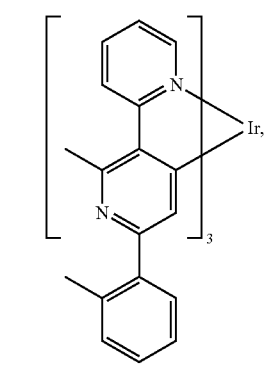
Compound 10
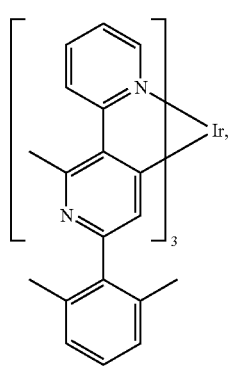
Compound 19
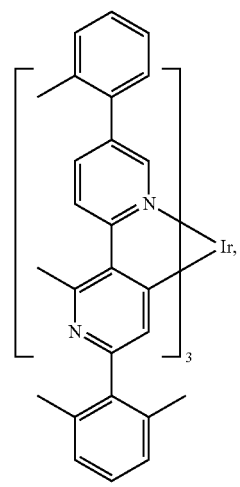
Compound 20
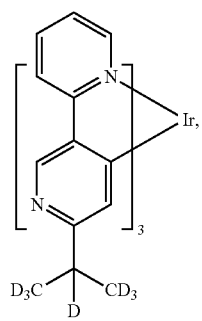
Compound 21
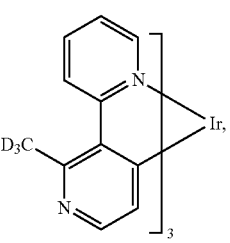
Compound 22
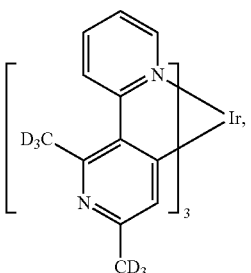
Compound 23
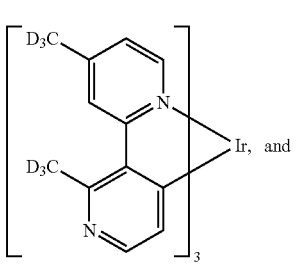

Compound 24

[structure: Ir complex with tris-bidentate ligand, CD3 groups]

7. A first device comprising a first organic light emitting device, the first organic light emitting device comprising:
   an anode;
   a cathode; and
   an organic layer, disposed between the anode and the cathode, comprising a compound having the formula Ir(L$_A$)$_m$(L$_B$)$_n$,
   wherein L$_B$ is a different ligand from L$_A$;
   wherein m ranges from 1 to 3, n ranges from 0 to 2, and m+n=3;
   wherein the ligand L$_A$ and, when present, L$_B$ are coordinated to the Ir;
   wherein the ligand L$_A$ is optionally linked with one or both of the other L$_A$ or L$_B$ ligands to comprise a tetradentate or hexadentate ligand;
   wherein L$_A$ is selected from the group consisting of

L$_{A1}$

L$_{A2}$

L$_{A3}$

L$_{A4}$

L$_{A5}$

L$_{A6}$

L$_{A7}$

L$_{A8}$ $L_{A9}$
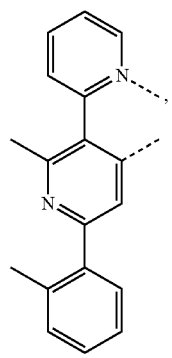
$L_{A10}$
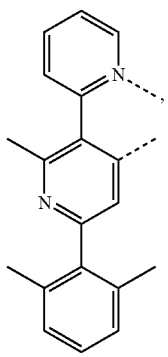
$L_{A19}$
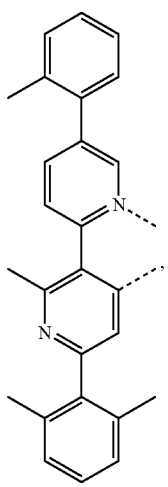
$L_{A21}$
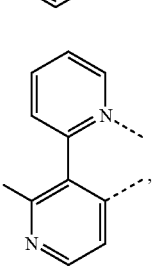
$L_{A22}$
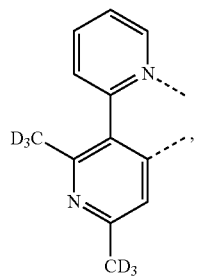
$L_{A23}$
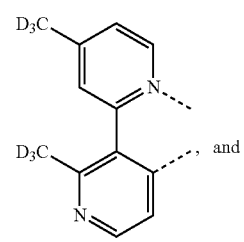
and
$L_{A24}$
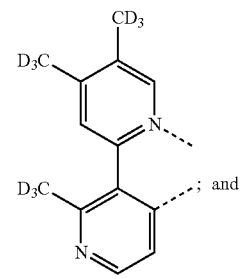
; and
wherein, when m is 1 or 2, $L_B$ is selected from the group consisting of:
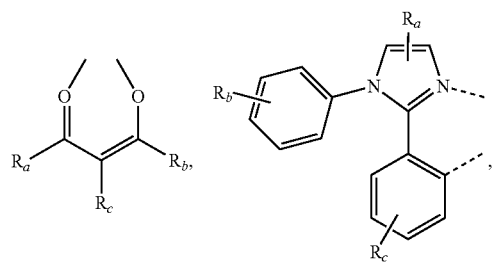
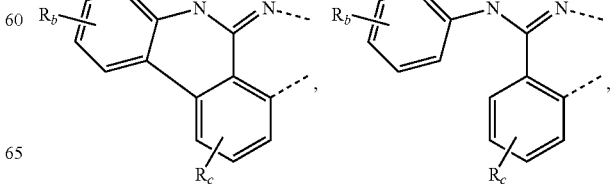

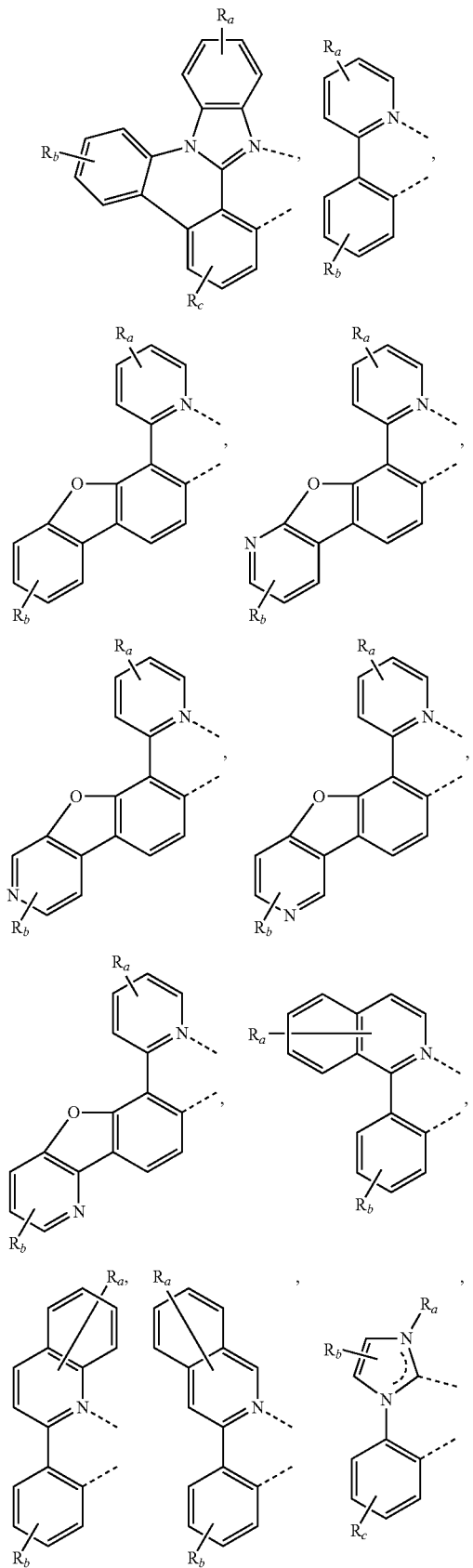

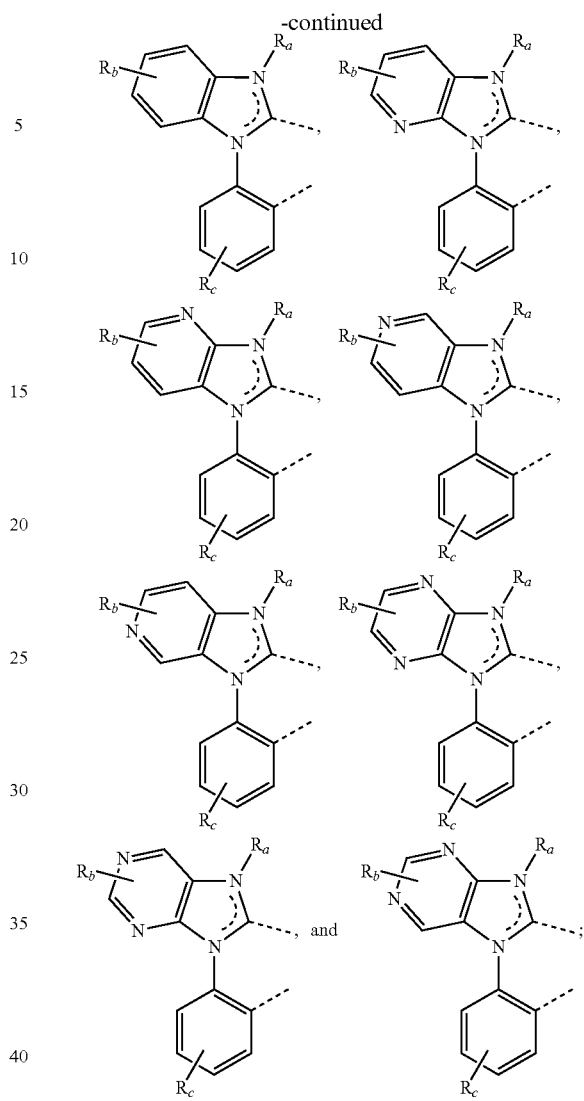

wherein $R_a$, $R_b$, and $R_c$ may represent mono, di, tri, or tetra substitution, or no substitution;

wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and $R_c$ are optionally joined to form a fused ring or form a multidentate ligand.

8. The first device of claim 7, wherein the organic layer is an emissive layer and the compound is an emissive dopant.

9. The first device of claim 7, wherein the organic layer is an emissive layer and the compound is a non-emissive dopant.

10. The first device of claim 7, wherein the organic layer further comprises a host.

11. The first device of claim 10, wherein host comprises at least one chemical group selected from the group consisting of carbazole, dibenzothiophene, dibenzofuran, dibenzoselenophene, azacarbazole, aza-dibenzothiophene, aza-dibenzofuran, and aza-dibenzoselenophene.

12. A formulation having the formula Ir(L$_A$)$_m$(L$_B$)$_n$, wherein L$_B$ is a different ligand from L$_A$;

wherein m ranges from 1 to 3, n ranges from 0 to 2, and m+n=3;

wherein the ligand L$_A$ and, when present, L$_B$ are coordinated to the Ir;

wherein the ligand L$_A$ is optionally linked with one or both of the other L$_A$ or L$_B$ ligands to comprise a tetradentate or hexadentate ligand;

wherein L$_A$ is selected from the group consisting of

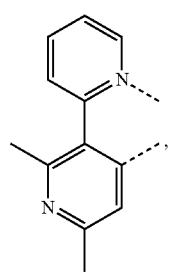
L$_{A1}$

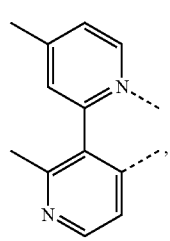
L$_{A2}$

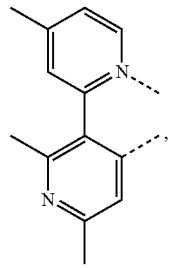
L$_{A3}$

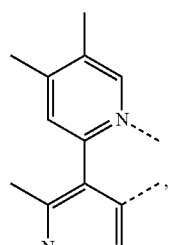
L$_{A4}$

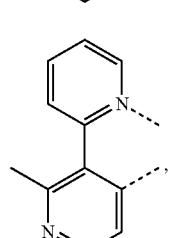
L$_{A5}$

-continued

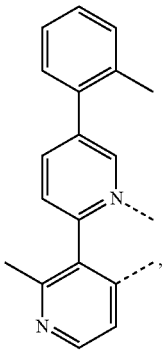
L$_{A6}$

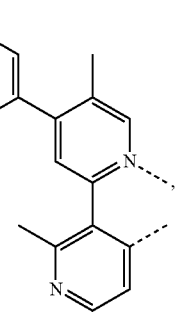
L$_{A7}$

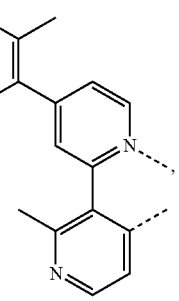
L$_{A8}$

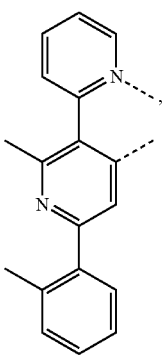
L$_{A9}$

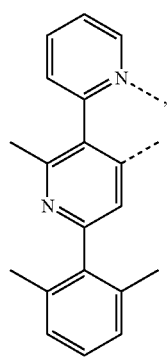
L_{A10}
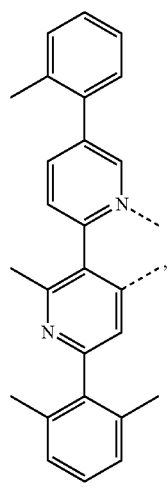
L_{A19}
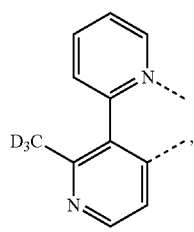
L_{A21}
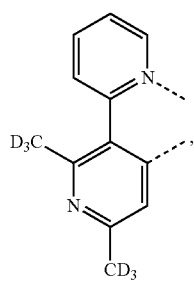
L_{A22}
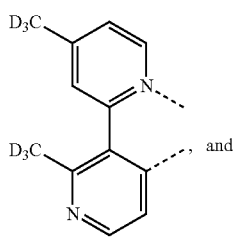
L_{A23}
and
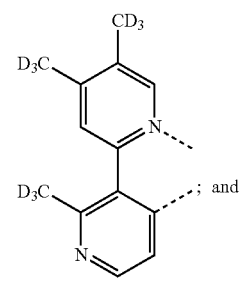
L_{A24}
; and
wherein, when m is 1 or 2, L_B is selected from the group consisting of:
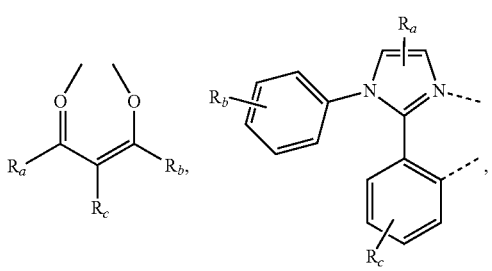
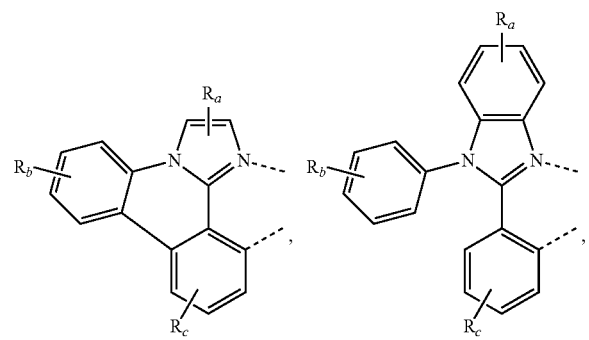
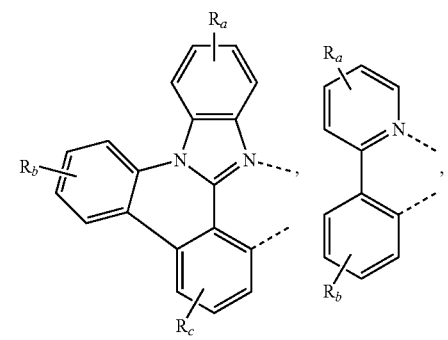

-continued

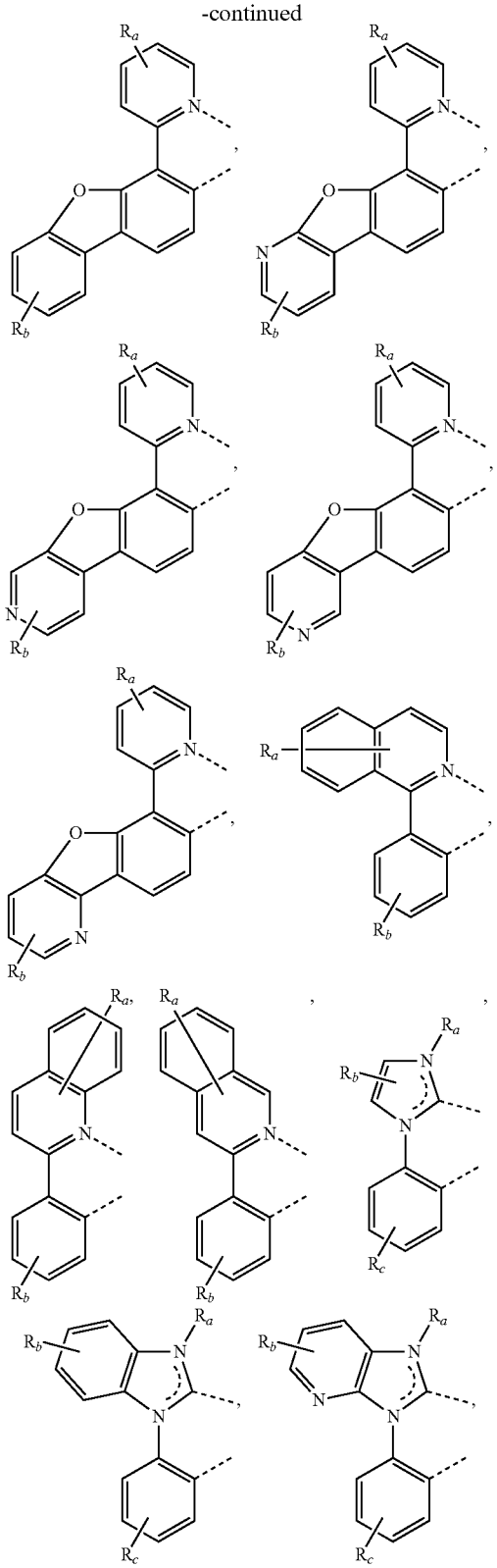

-continued

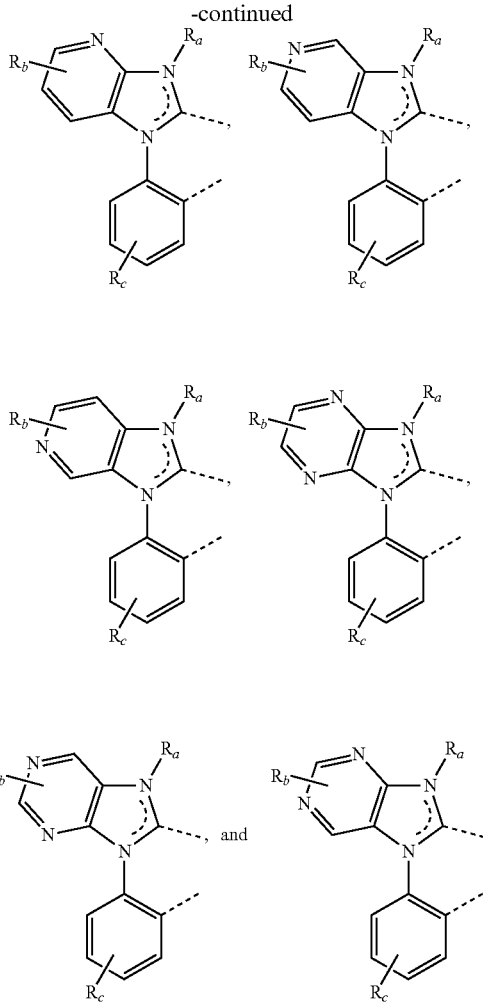

wherein $R_a$, $R_b$, and $R_c$ may represent mono, di, tri, or tetra substitution, or no substitution;

wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and $R_c$ are optionally joined to form a fused ring or form a multidentate ligand.

13. The compound of claim 1, wherein m is 1 or 2, and $L_A$ is linked with one or both of the other ligands $L_A$, $L_B$, or $L_A$ and $L_B$.

14. The compound of claim 1, wherein m is 3 and $L_A$ is linked with one or both of the other $L_A$ ligands to form a tetradentate or hexadentate ligand.

* * * * *

UNITED STATES PATENT AND TRADEMARK OFFICE
CERTIFICATE OF CORRECTION

PATENT NO. : 9,978,961 B2
APPLICATION NO. : 14/310598
DATED : May 22, 2018
INVENTOR(S) : Tsai et al.

Page 1 of 14

It is certified that error appears in the above-identified patent and that said Letters Patent is hereby corrected as shown below:

In the Specification

Column 9, Lines 32-43, please delete the compound

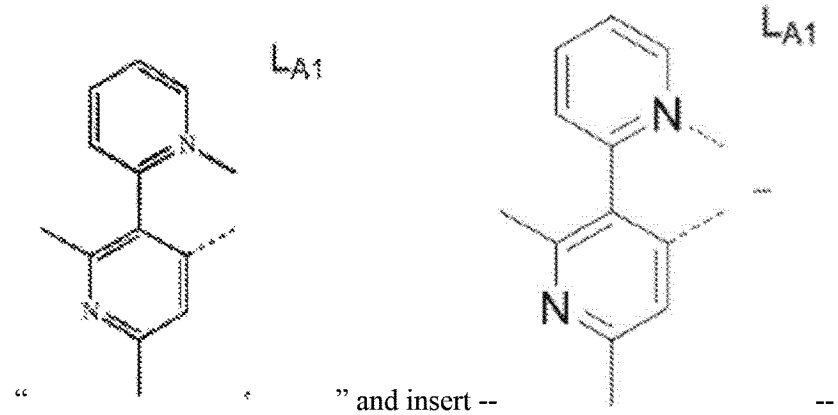

Column 9, Lines 44-55, please delete the compound

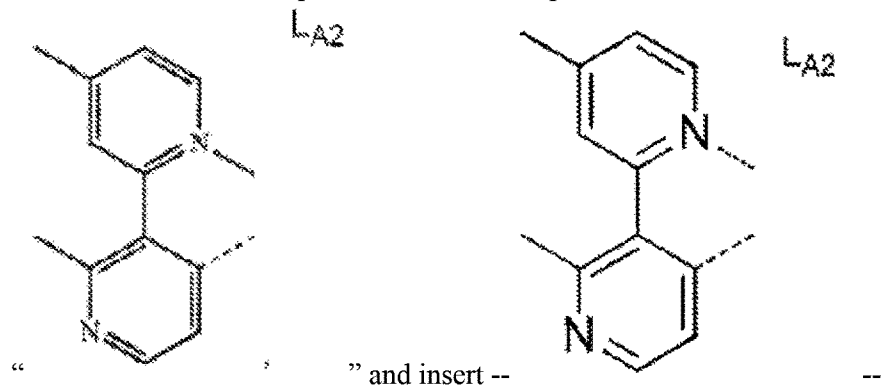

Signed and Sealed this
Thirty-first Day of July, 2018

Andrei Iancu
*Director of the United States Patent and Trademark Office*

Column 9, Lines 56-67, please delete the compound
" 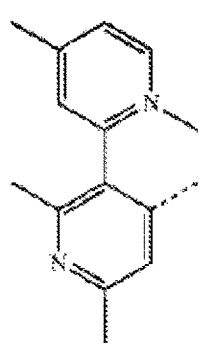 " and insert -- 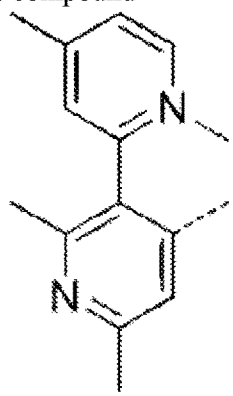 --
Column 10, Lines 3-15, please delete compound
" 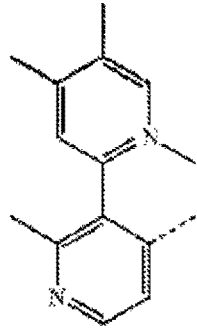 " and insert -- 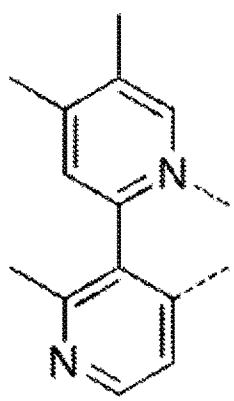 --
Column 10, Lines 16-25, please delete the compound
" 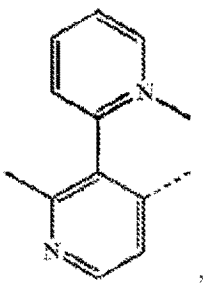 " and insert -- 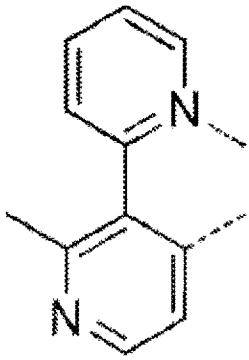 --

CERTIFICATE OF CORRECTION (continued)
U.S. Pat. No. 9,978,961 B2

Column 10, Lines 26-42, please delete the compound

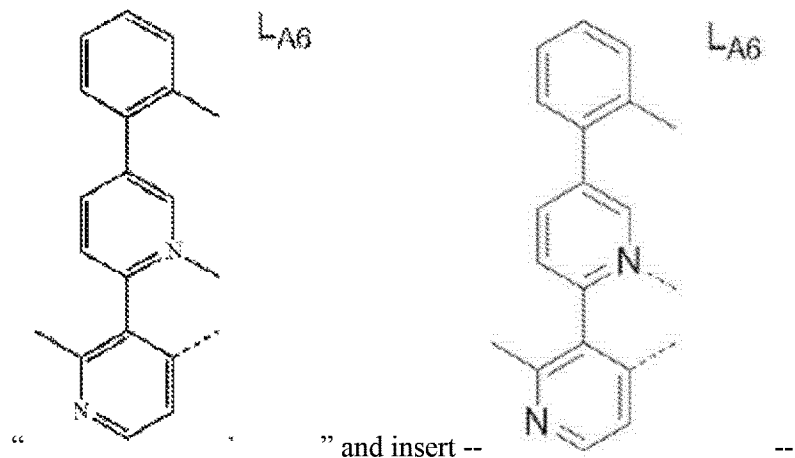

" and insert -- --

Column 10, Lines 43-54, please delete the compound

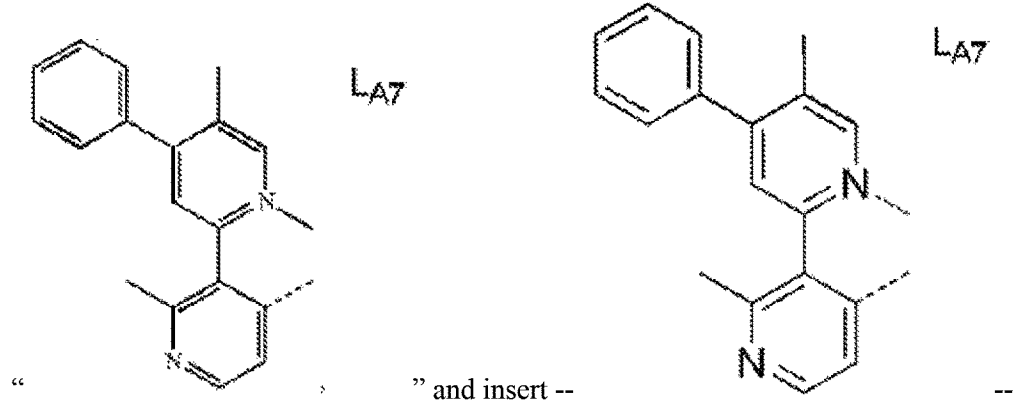

" and insert -- --

Column 10, Lines 55-67, please delete the compound

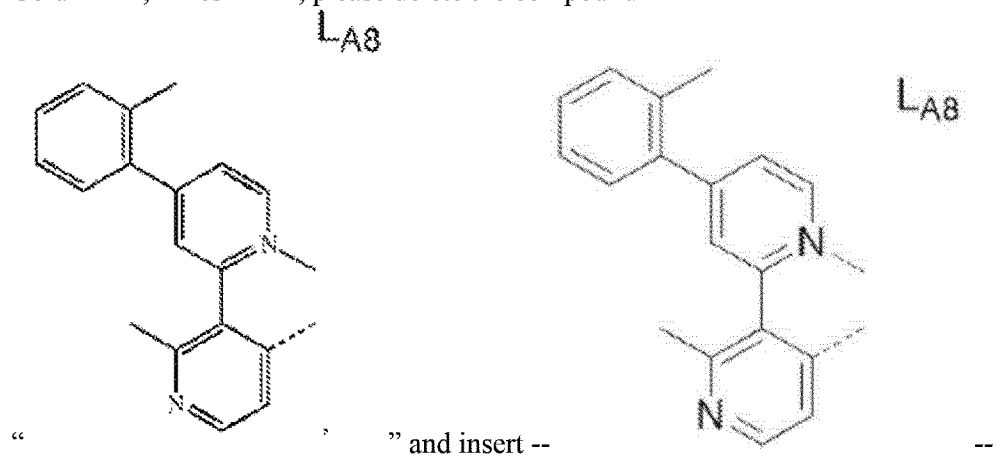

" and insert -- --

CERTIFICATE OF CORRECTION (continued)
U.S. Pat. No. 9,978,961 B2

Column 11, Lines 3-16, please delete the compound

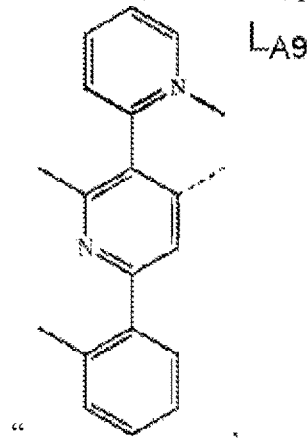 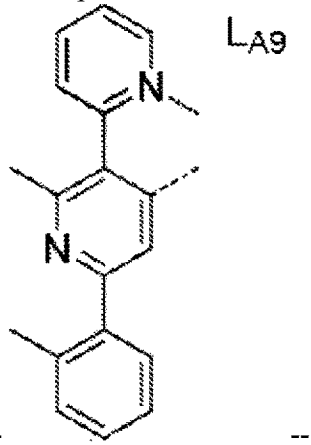

" " and insert -- --

Column 11, Lines 17-30, please delete the compound

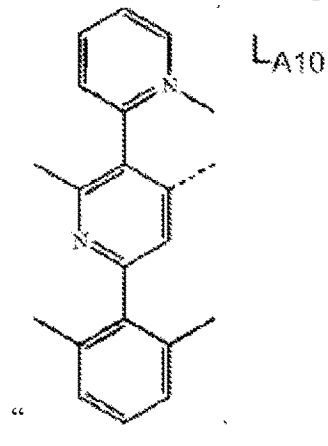 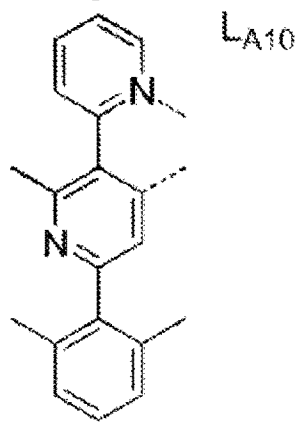

" " and insert -- --

Column 11, Lines 31-42, please delete the compound

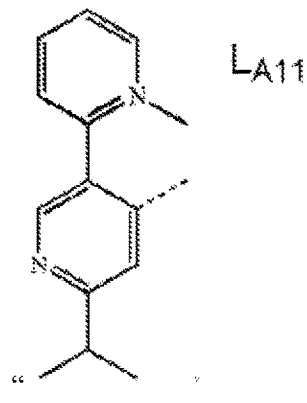 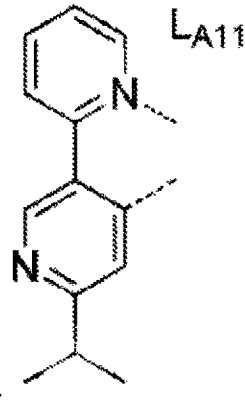

" " and insert -- --

Column 11, Lines 43-57, please delete the compound
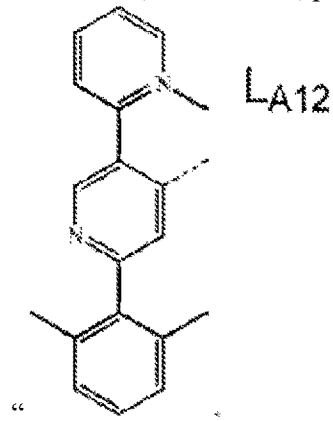
" and insert -- 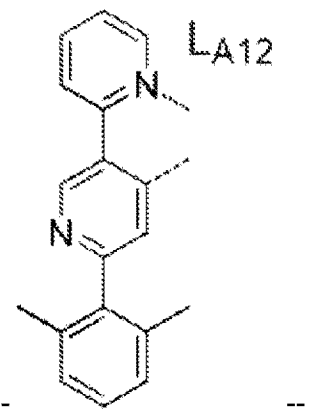 --
Column 11, Lines 58-67, please delete the compound
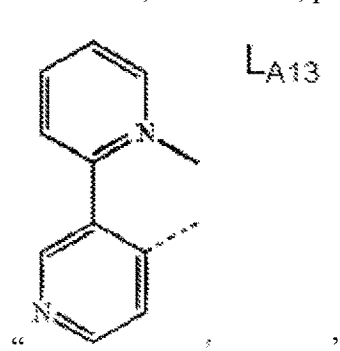
" and insert -- 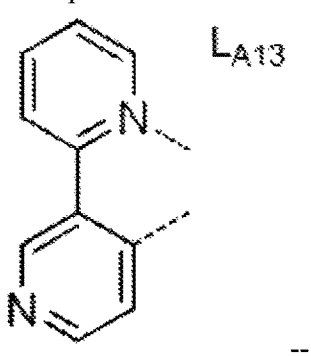 --
Column 12, Lines 3-14, please delete the compound
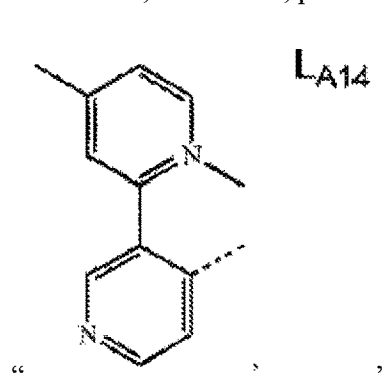
" and insert -- 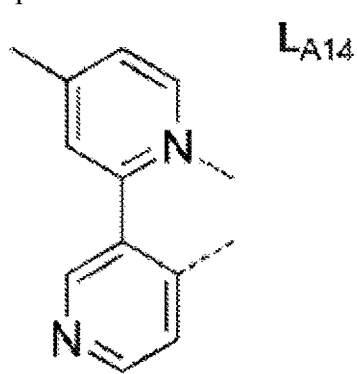 --

CERTIFICATE OF CORRECTION (continued)
U.S. Pat. No. 9,978,961 B2

Page 6 of 14

Column 12, Lines 15-28, please delete the compound

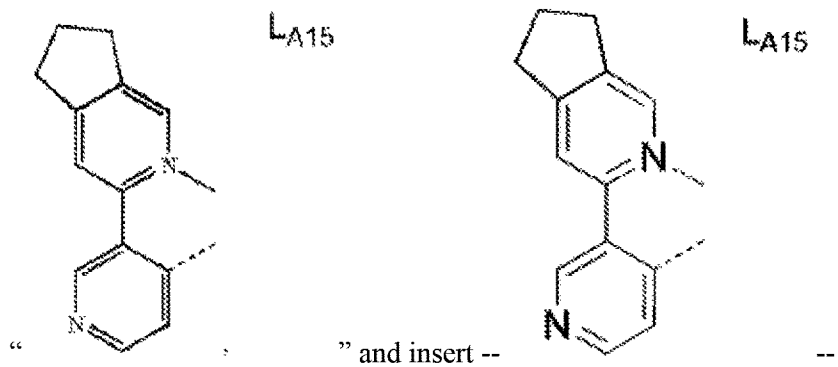

" and insert -- --

Column 12, Lines 29-42, please delete the compound

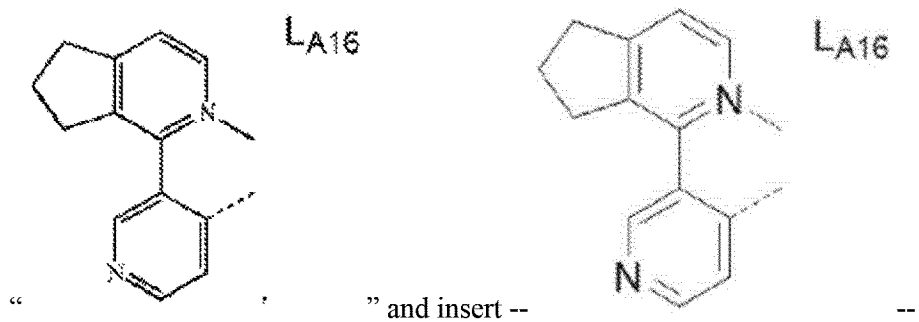

" and insert -- --

Column 12, Lines 43-54, please delete the compound

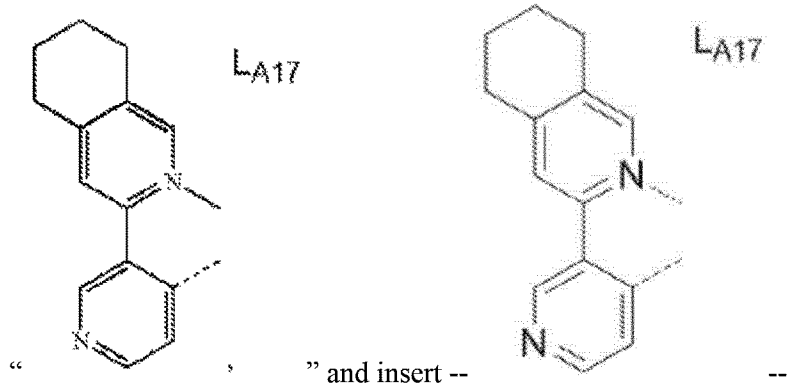

" and insert -- --

Column 12, Lines 55-67, please delete the compound

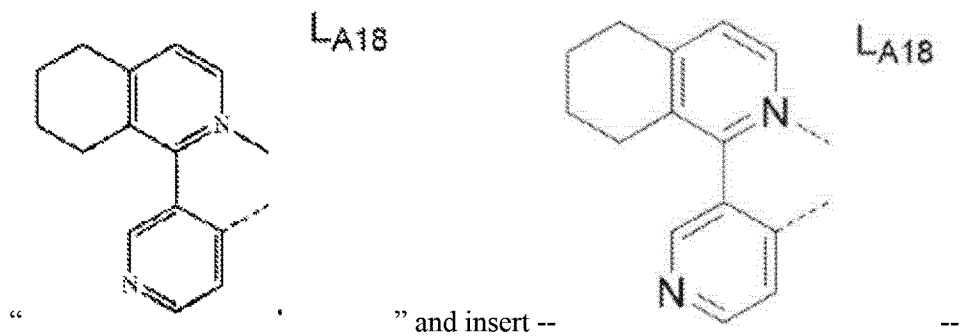

" and insert -- --

CERTIFICATE OF CORRECTION (continued)
U.S. Pat. No. 9,978,961 B2

Column 13, Lines 3-21, please delete the compound

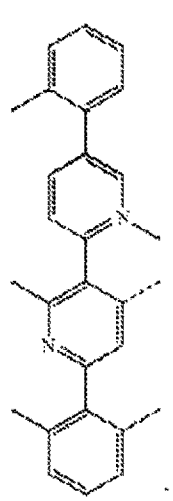
" and insert --
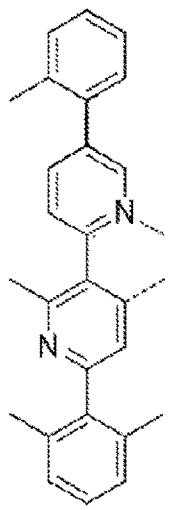
--

Column 13, Lines 22-34, please delete the compound

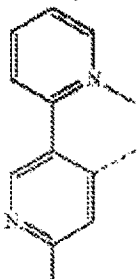
" and insert --
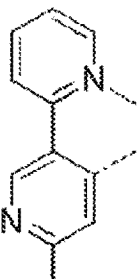
--

Column 13, Lines 35-44, please delete the compound

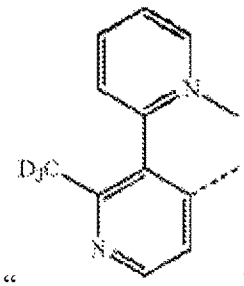
" and insert --
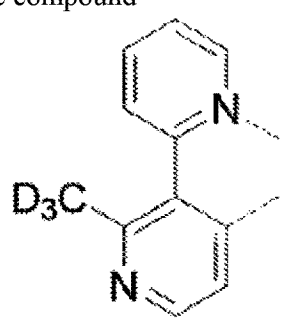
--

CERTIFICATE OF CORRECTION (continued)
U.S. Pat. No. 9,978,961 B2

Column 13, Lines 45-56, please delete the compound

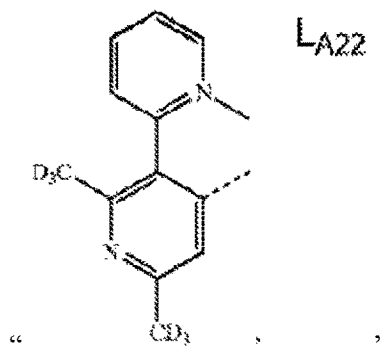 " and insert -- 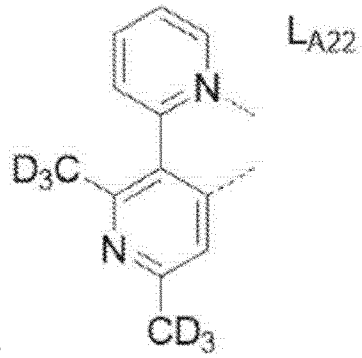 --

Column 13, Lines 57-67, please delete the compound

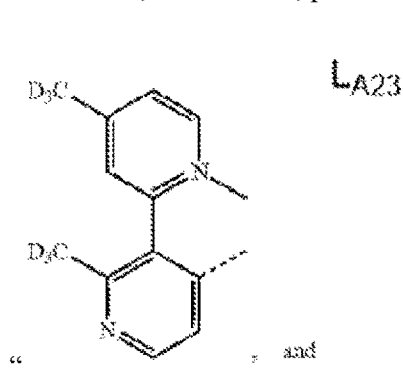 " and insert -- 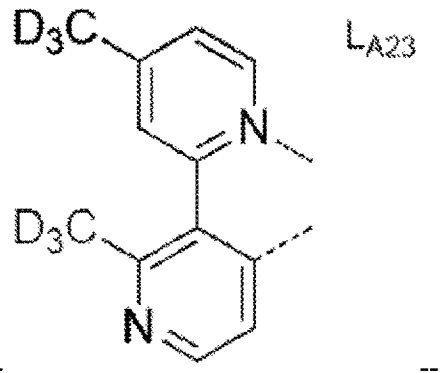 --

Column 14, Lines 3-13, please delete the compound

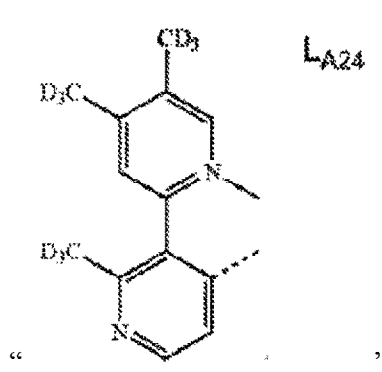 " and insert -- 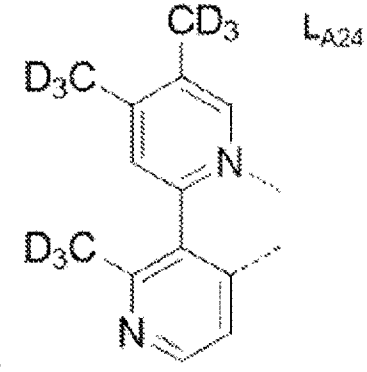 --

CERTIFICATE OF CORRECTION (continued)
U.S. Pat. No. 9,978,961 B2

In the Claims

Column 129, Lines 57-67, please delete the compound

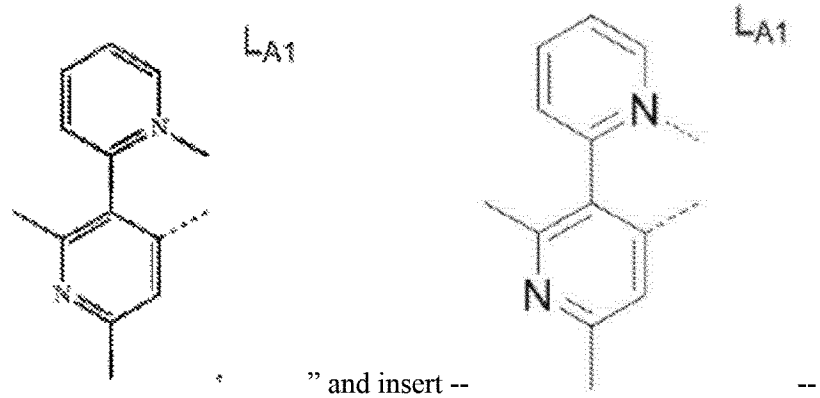

Column 130, Lines 16-26, please delete the compound

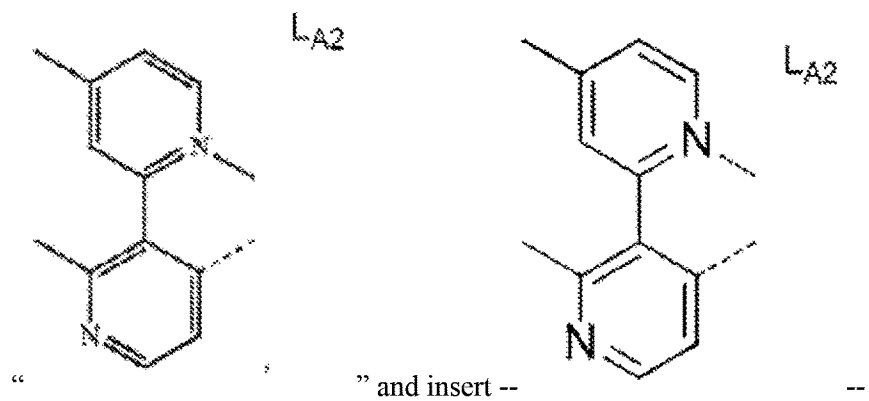

Column 130, Lines 27-43, please delete the compound

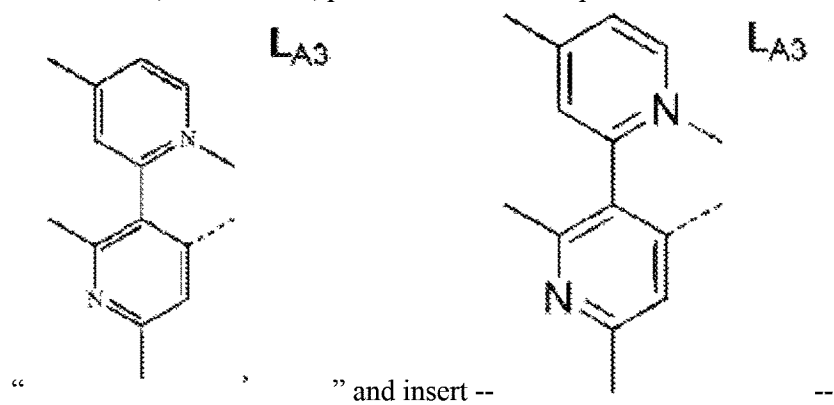

CERTIFICATE OF CORRECTION (continued)
U.S. Pat. No. 9,978,961 B2

Column 130, Lines 44-54, please delete compound

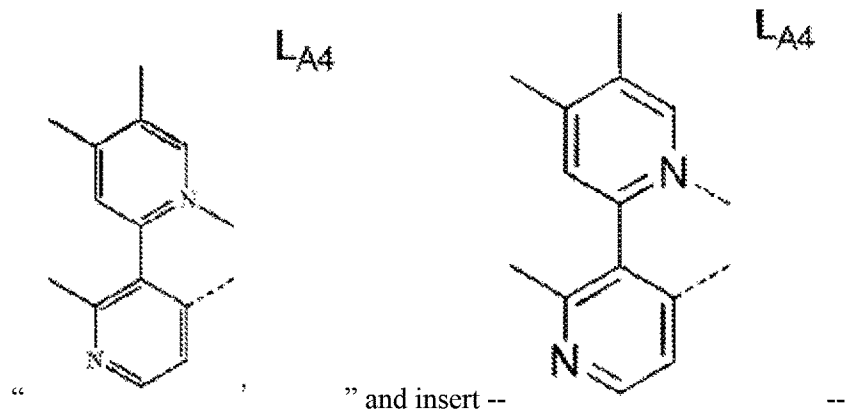

" and insert -- --

Column 130, Lines 55-67, please delete the compound

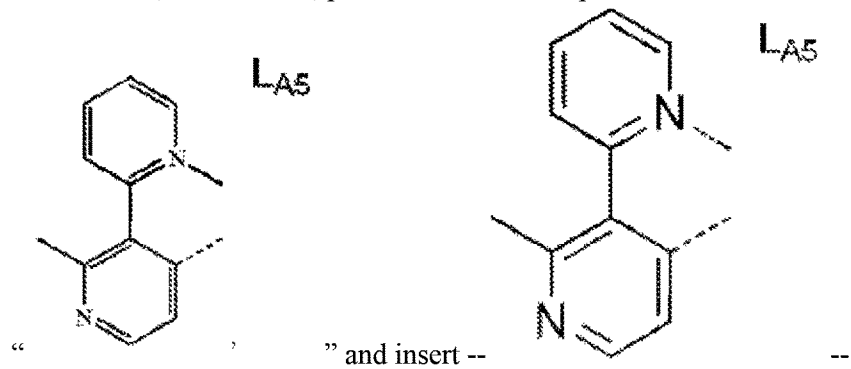

" and insert -- --

Column 131, Lines 3-20, please delete the compound

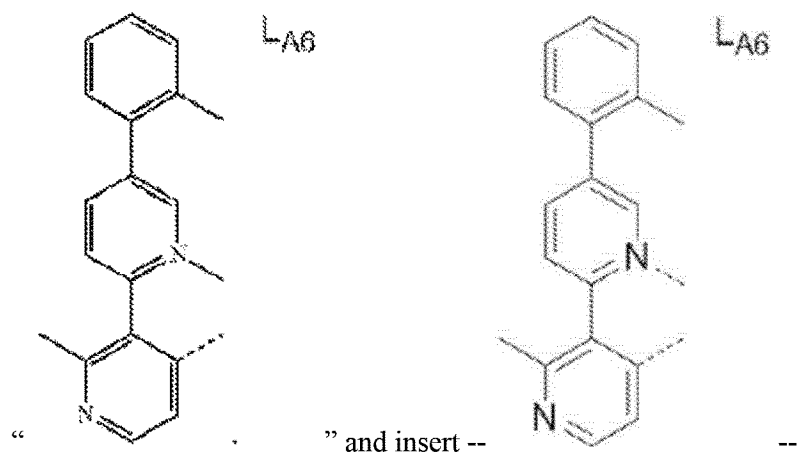

" and insert -- --

Column 131, Lines 21-37, please delete the compound
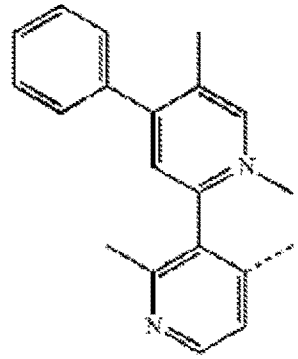 " and insert -- 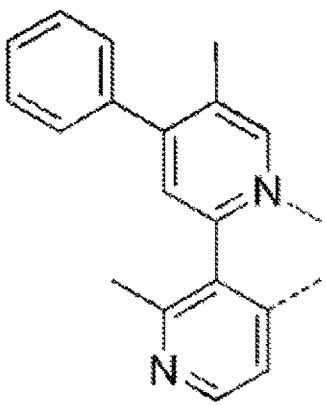 --
Column 131, Lines 38-52, please delete the compound
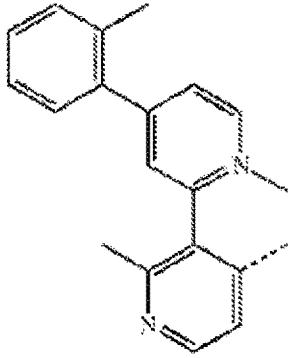 " and insert -- 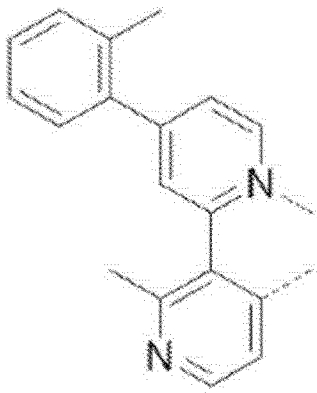 --
Column 131, Lines 53-67, please delete the
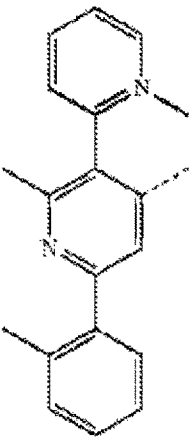 " and insert -- 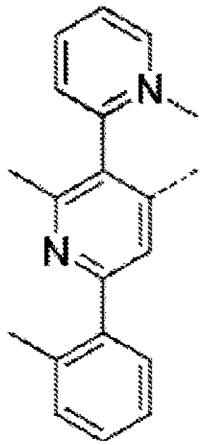 --

CERTIFICATE OF CORRECTION (continued)
U.S. Pat. No. 9,978,961 B2

Column 132, Lines 3-16, please delete the compound

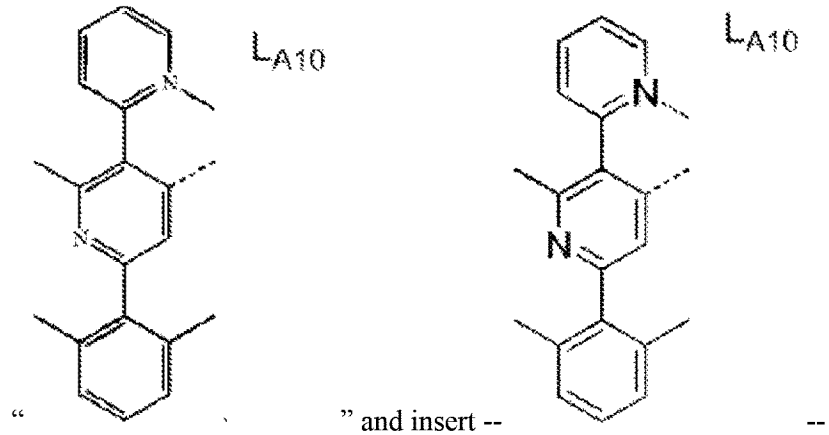

Column 132, Lines 17-35, please delete the compound

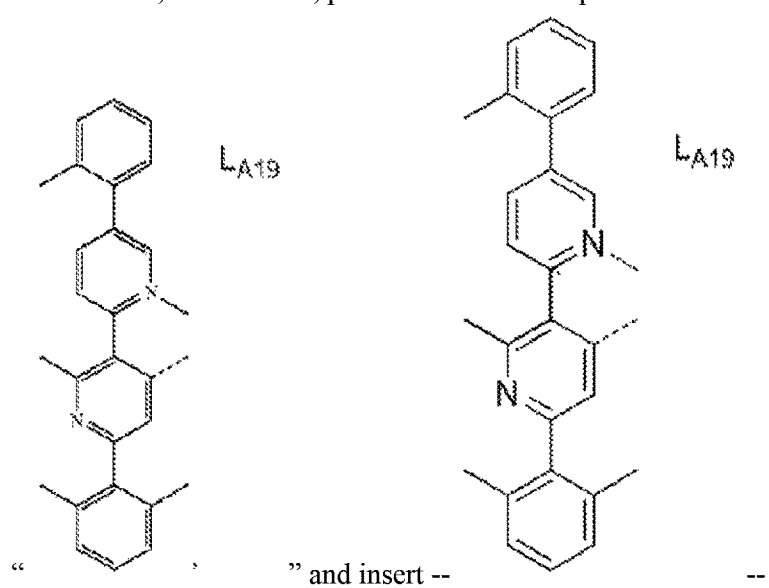

Column 132, Lines 36-44, please delete the compound

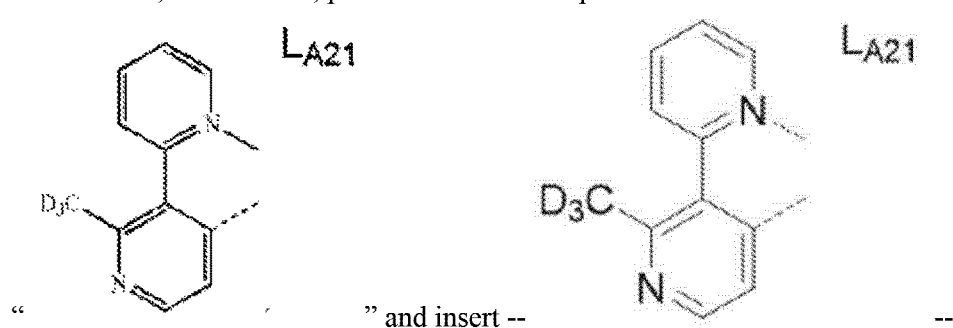

CERTIFICATE OF CORRECTION (continued)
U.S. Pat. No. 9,978,961 B2

Column 132, Lines 45-56, please delete the compound

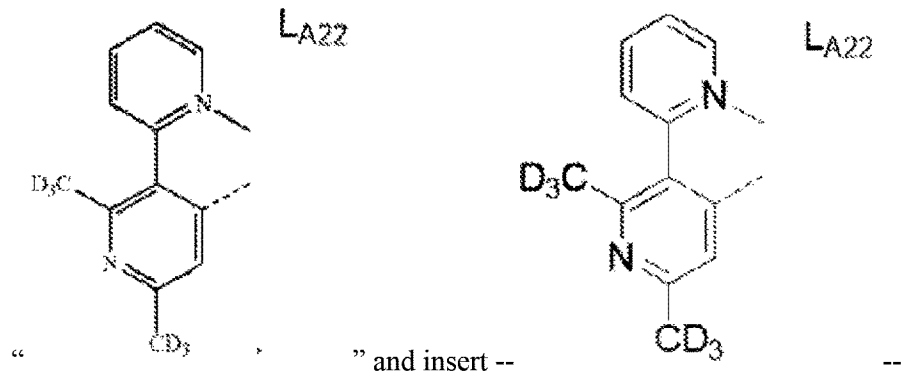

Column 132, Lines 57-67, please delete the compound

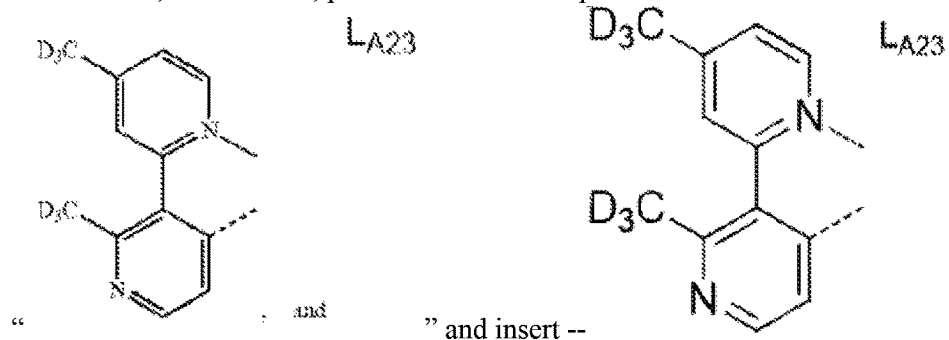

Column 133, Lines 3-12, please delete the compound

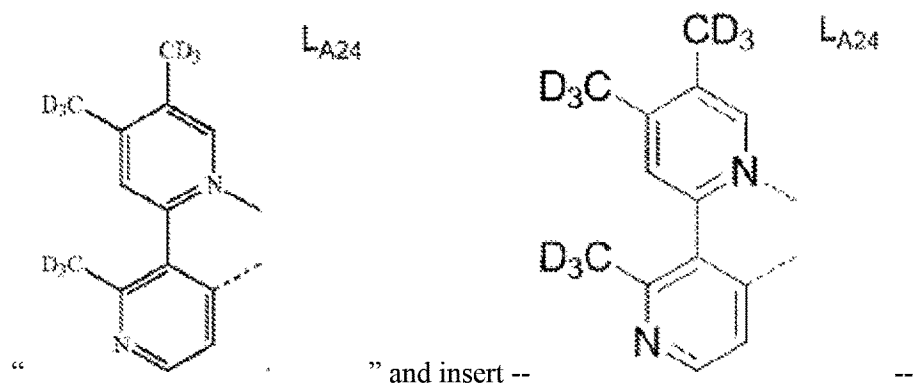

Column 138, Lines 22-34, please delete the compound "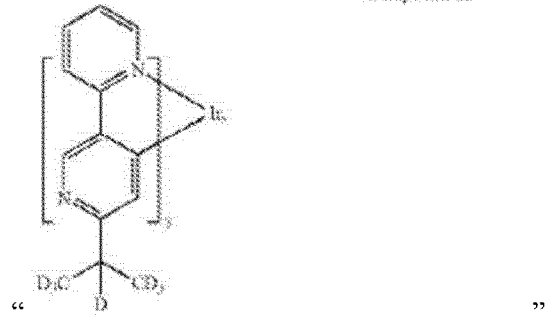"